US008450271B2

(12) United States Patent
Shah et al.

(10) Patent No.: US 8,450,271 B2
(45) Date of Patent: May 28, 2013

(54) PEPTIDE-BASED SCAFFOLDS FOR CARTILAGE REGENERATION AND METHODS FOR THEIR USE

(75) Inventors: Ramille N. Shah, Chicago, IL (US); Nirav A. Shah, Chicago, IL (US); Samuel I. Stupp, Chicago, IL (US)

(73) Assignee: Northwestern University, Evanston, IL (US)

( * ) Notice: Subject to any disclaimer, the term of this patent is extended or adjusted under 35 U.S.C. 154(b) by 281 days.

(21) Appl. No.: 12/759,683

(22) Filed: Apr. 13, 2010

(65) Prior Publication Data

US 2010/0266557 A1  Oct. 21, 2010

Related U.S. Application Data

(60) Provisional application No. 61/168,894, filed on Apr. 13, 2009.

(51) Int. Cl.
- A61K 38/18 (2006.01)
- A61K 38/00 (2006.01)
- A61K 38/04 (2006.01)
- C07K 14/495 (2006.01)
- C07K 5/00 (2006.01)
- A61P 19/00 (2006.01)

(52) U.S. Cl.
USPC ............................ 514/8.9; 514/17.1; 530/326

(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 4,930,077 A | 5/1990 | Fan | |
| 5,110,604 A * | 5/1992 | Chu et al. | 424/484 |
| 5,114,713 A | 5/1992 | Sinigaglia | |
| 5,130,123 A | 7/1992 | Reynolds et al. | |
| 5,208,111 A | 5/1993 | Decher et al. | |
| 5,223,409 A | 6/1993 | Ladner et al. | |
| 5,622,699 A | 4/1997 | Ruoslahti et al. | |
| 5,670,483 A | 9/1997 | Zhang et al. | |
| 5,733,868 A | 3/1998 | Peterson et al. | |
| 5,843,780 A | 12/1998 | Thomson | |
| 5,853,830 A | 12/1998 | McCaulley et al. | |
| 5,871,767 A | 2/1999 | Dionne et al. | |
| 5,955,343 A | 9/1999 | Holmes et al. | |
| 5,993,541 A | 11/1999 | Litvin et al. | |
| 6,051,272 A | 4/2000 | Stupp et al. | |
| 6,085,206 A | 7/2000 | Domini et al. | |
| 6,096,863 A | 8/2000 | Fields et al. | |
| 6,114,038 A | 9/2000 | Castro et al. | |
| 6,156,321 A | 12/2000 | Thorpe et al. | |
| 6,181,909 B1 | 1/2001 | Burstein et al. | |
| 6,201,065 B1 | 3/2001 | Pathak et al. | |
| 6,207,218 B1 | 3/2001 | Layrolle et al. | |
| 6,265,539 B1 | 7/2001 | Arlinghaus | |
| 6,269,368 B1 | 7/2001 | Diamond | |
| 6,270,765 B1 | 8/2001 | Deo et al. | |
| 6,309,862 B1 | 10/2001 | Jarekrans et al. | |
| 6,391,297 B1 | 5/2002 | Halvorsen | |
| 6,444,723 B1 | 9/2002 | Kline | |
| 6,458,924 B2 | 10/2002 | Knudsen et al. | |
| 6,473,730 B1 | 10/2002 | McKeown et al. | |
| 6,548,048 B1 | 4/2003 | Cuthbertson et al. | |
| 6,548,630 B1 | 4/2003 | Zhang et al. | |
| 6,562,619 B1 | 5/2003 | Gearhart et al. | |
| 6,800,481 B1 | 10/2004 | Holmes et al. | |
| 6,855,329 B1 | 2/2005 | Shakesheff et al. | |
| 6,890,654 B2 | 5/2005 | Stupp et al. | |
| 7,371,719 B2 | 5/2008 | Stupp et al. | |
| 7,390,526 B2 | 6/2008 | Stupp et al. | |
| 7,452,679 B2 | 11/2008 | Stupp et al. | |
| 7,491,690 B2 | 2/2009 | Stupp et al. | |
| 7,534,761 B1 | 5/2009 | Stupp et al. | |
| 7,544,661 B2 | 6/2009 | Stupp et al. | |
| 7,554,021 B2 | 6/2009 | Stupp et al. | |
| 7,683,025 B2 | 3/2010 | Stupp et al. | |
| 7,745,708 B2 | 6/2010 | Stupp et al. | |
| 7,838,491 B2 | 11/2010 | Stupp et al. | |
| 7,851,445 B2 | 12/2010 | Stupp et al. | |

(Continued)

FOREIGN PATENT DOCUMENTS

| | | |
|---|---|---|
| CN | 1302211 A | 7/2001 |
| CN | 1761531 A | 4/2006 |

(Continued)

OTHER PUBLICATIONS

Orthopale.com. Arthroscopic-debridement. Last updated Sep. 12, 2007. Accessed online Aug. 16, 2012. 2 pages.*
Temenoff et al. Review: tissue engineering for regeneration of articular cartilage. Biomaterials, 2000, vol. 21, pp. 431-440.*
Copping, Aaron M. and Vanda R. G. Pond. Dec. 9, 1950. "Folic Acid as a Growth-Factor for the Rat." *Nature*. No. 4232, p. 993.
Brown, Walter E. Dec. 15, 1962. "Octacalcium Phosphate and Hydroxyapatite." *Nature*. vol. 196, pp. 1048-1050.
Liang, W. Y. and A. D. Yoffe. Jan. 8, 1968. "Transmission Spectra of ZnO Single Crystals." *Physical Review Letters*. vol. 20, No. 2, pp. 59-62.

(Continued)

*Primary Examiner* — Marcela M Cordero Garcia
(74) *Attorney, Agent, or Firm* — Fanelli Haag & Kilger PLLC

(57) ABSTRACT

Disclosed herein are novel peptide amphiphile molecules and compositions composed of a peptide sequence that non-covalently binds the growth factor TGF-β1. Also disclosed are methods of using these peptide amphiphiles to create a gel scaffold in situ that enhances articular cartilage regeneration when used in combination with microfracture. Significant improvement in tissue quality and overall O'Driscoll histological scores were observed in rabbits with full thickness articular cartilage defects treated with the TGF-binding peptide amphiphile. The gel can further serve as a delivery vehicle for recombinant TGF-β1 protein growth factor. Scaffolds that localize and retain chondrogenic growth factors may synergistically enhance cartilage repair when combined with microfracture, by inducing bone marrow mesenchymal stem cells into chondrogenic differentiation. This invention represents a promising new biomimetic approach to enhance current techniques of articular cartilage regeneration in the clinical setting.

27 Claims, 7 Drawing Sheets

U.S. PATENT DOCUMENTS

| | | | |
|---|---|---|---|
| 8,063,014 | B2 | 11/2011 | Stupp et al. |
| 8,076,295 | B2 | 12/2011 | Hulvat et al. |
| 8,124,583 | B2 | 2/2012 | Stupp et al. |
| 8,138,140 | B2 | 3/2012 | Stupp et al. |
| 2002/0007217 | A1 | 1/2002 | Jacob et al. |
| 2002/0046018 | A1 | 4/2002 | Marcu et al. |
| 2002/0142277 | A1 | 10/2002 | Burstein et al. |
| 2002/0160471 | A1 | 10/2002 | Kisiday et al. |
| 2003/0050231 | A1 | 3/2003 | Rosen et al. |
| 2003/0059906 | A1 | 3/2003 | Hubbell et al. |
| 2003/0092672 | A1 | 5/2003 | Darcy et al. |
| 2003/0176335 | A1 | 9/2003 | Zhang et al. |
| 2003/0187232 | A1 | 10/2003 | Hubbell et al. |
| 2004/0001893 | A1 | 1/2004 | Stupp et al. |
| 2004/0018961 | A1 | 1/2004 | Stupp et al. |
| 2004/0022718 | A1 | 2/2004 | Stupp et al. |
| 2004/0068266 | A1 | 4/2004 | Delmotte |
| 2004/0214272 | A1 | 10/2004 | La Rosa et al. |
| 2004/0258726 | A1 | 12/2004 | Stupp et al. |
| 2005/0208589 | A1 | 9/2005 | Stupp et al. |
| 2005/0209145 | A1 | 9/2005 | Stupp et al. |
| 2005/0214257 | A1 | 9/2005 | Zhao et al. |
| 2005/0272662 | A1 | 12/2005 | Stupp et al. |
| 2006/0008544 | A1 | 1/2006 | Myhill et al. |
| 2006/0123505 | A1 | 6/2006 | Kikuchi et al. |
| 2006/0149036 | A1 | 7/2006 | Stupp et al. |
| 2006/0188555 | A1 | 8/2006 | Cormier et al. |
| 2006/0247165 | A1 | 11/2006 | Stupp et al. |
| 2007/0142282 | A1 | 6/2007 | Alitalo et al. |
| 2007/0277250 | A1 | 11/2007 | Stupp et al. |
| 2008/0175883 | A1 | 7/2008 | Hsu et al. |
| 2008/0177033 | A1 | 7/2008 | Stupp et al. |
| 2008/0248569 | A1 | 10/2008 | Mata et al. |
| 2008/0299657 | A1 | 12/2008 | Stupp et al. |
| 2009/0042804 | A1 | 2/2009 | Hulvat et al. |
| 2009/0098652 | A1 | 4/2009 | Stupp et al. |
| 2009/0269847 | A1 | 10/2009 | Stupp et al. |
| 2010/0221224 | A1 | 9/2010 | Stupp et al. |
| 2010/0266557 | A1 | 10/2010 | Shah et al. |
| 2011/0008890 | A1 | 1/2011 | Stupp et al. |
| 2012/0264912 | A1 | 10/2012 | Stupp et al. |

FOREIGN PATENT DOCUMENTS

| | | |
|---|---|---|
| CN | 2007-483492 | 2/2007 |
| CN | 1915438 | 2/2007 |
| EP | 1073475 B1 | 7/2007 |
| JP | 403099096 A | 4/1991 |
| WO | WO 93/22343 | 11/1993 |
| WO | WO 94/02506 | 2/1994 |
| WO | 96/02260 A1 | 2/1996 |
| WO | WO 97/14713 A1 | 4/1997 |
| WO | WO 97/20639 A1 | 6/1997 |
| WO | WO 98/07752 A1 | 2/1998 |
| WO | 98/43686 A1 | 10/1998 |
| WO | WO 99/36107 A1 | 7/1999 |
| WO | WO 99/55383 A2 | 11/1999 |
| WO | WO 00/13710 A2 | 3/2000 |
| WO | WO 00/44808 A1 | 8/2000 |
| WO | WO 00/45831 A1 | 8/2000 |
| WO | WO 00/52145 A2 | 9/2000 |
| WO | WO 00/64481 A1 | 11/2000 |
| WO | WO 01/00650 A1 | 1/2001 |
| WO | 01/48148 A1 | 7/2001 |
| WO | 01/55302 A2 | 8/2001 |
| WO | 01/56628 A1 | 8/2001 |
| WO | 02/20822 A2 | 3/2002 |
| WO | 02/39118 A1 | 5/2002 |
| WO | 02/062961 A2 | 8/2002 |
| WO | WO 02/062969 A2 | 8/2002 |
| WO | WO 03/040336 A2 | 5/2003 |
| WO | WO 03/054146 A2 | 7/2003 |
| WO | WO 03/070749 A2 | 8/2003 |
| WO | WO 03/084980 A2 | 10/2003 |
| WO | WO 03/090255 A2 | 10/2003 |
| WO | WO 2004/003561 A1 | 1/2004 |
| WO | WO 2004/018628 A2 | 3/2004 |
| WO | WO 2004/024778 A2 | 3/2004 |
| WO | WO 2004/046167 A2 | 6/2004 |
| WO | 2004/071545 A2 | 8/2004 |
| WO | WO 2004/072104 A2 | 8/2004 |
| WO | WO 2004/091370 A2 | 10/2004 |
| WO | WO 2004/106359 A2 | 12/2004 |
| WO | WO 2005/003292 A2 | 1/2005 |
| WO | WO 2005/014619 A2 | 2/2005 |
| WO | WO 2005/056039 A1 | 6/2005 |
| WO | WO 2005/056576 A2 | 6/2005 |
| WO | 2006/079036 A2 | 7/2006 |
| WO | WO 2006/096614 A2 | 9/2006 |
| WO | 2008/131052 A2 | 10/2008 |

OTHER PUBLICATIONS

Greenfield, Norma and Gerald D. Fasman. Oct. 1969. "Computed Circular Dichroism Spectra for the Evaluation of Protein Conformation." *Biochemistry*. vol. 8, No. 10, pp. 4108-4116.

Hantke, Klaus and Volkmar Braun. 1973. "Covalent Binding of Lipid to Protein: Diglyceride and Amide-Linked Fatty Acid at the N-Terminal End of the Murein-Lipoprotein of the *Escherichia coli* Outer Membrane." *Eur. J. Biochem*. vol. 34, No. 2, pp. 284-296.

Balcerski, James S., E. S. Pysh, G. M. Bonora, and C. Toniolo. Jun. 9, 1976. "Vacuum Ultraviolet Circular Dichroism of β-Forming Alkyl Oligopeptides." *Journal of the American Chemical Society*. vol. 98, No. 12, pp. 3470-3473.

Jacobson, Bruce S. and Daniel Branton. Jan. 21, 1977. "Plasma Membrane: Rapid Isolation and Exposure of the Cytoplasmic Surface by Use of Positively Charged Beads." *Science*. vol. 195, No. 4275, pp. 302-304.

Biesecker, G., J. Ieuan Harris, J. C. Thierry, J. E. Walker, and A. J. Wonacott. Mar. 24, 1977. *Nature*. vol. 266, pp. 328-333.

Kelly, Margaret M., E. S. Pysh, G. M. Bonora, and C. Toniolo. May 11, 1977. "Vacuum Ultraviolet Circular Dichroism of Protected Homooligomers Derived from L-Leucine." *Journal of the American Chemical Society*. vol. 99, No. 10, pp. 3264-3266.

Blumenthal, N. C., A. S. Posner, L. D. Silverman, and L. C. Rosenberg. 1979. "Effect of Proteoglycans on in Vitro Hydroxyapatite Formation." *Calcified Tissue International*. vol. 27, No. 1, pp. 75-82.

Richardson, P. M., U. M. McGuinness, and A. J. Aguayo. Mar. 20, 1980. "Axons from CNS Neurones Regenerate into PNS Grafts." *Nature*. vol. 284, pp. 264-265.

Lim, Franklin and Anthony M. Sun. Nov. 21, 1980. "Microencapsulated Islets as Bioartificial Endocrine Pancreas." *Science*. vol. 210, No. 4472, pp. 908-910.

Jain, Rakesh K., Chhitar M. Gupta, and Nitya Anand. 1981. "Synthesis of Peptidylglycophospholipids, Novel Derivatives of Muramyl-Dipeptide." *Tetrahedron Letters*. vol. 22, No. 24, pp. 2317-2320.

Sarin, Virender K., Stephen B. H. Kent, James P. Tam, and R. B. Merrifield. 1981. "Quantitative Monitoring of Solid-Phase Peptide Synthesis by the Ninhydrin Reaction." *Analytical Biochemistry*. vol. 117, pp. 147-157.

Yannas, I. V., J. F. Burke, D. P. Orgill, E. M. Skrabut. Jan. 8, 1982. "Wound Tissue Can Utilize a Polymeric Template to Synthesize a Functional Extension of Skin." *Science*. vol. 215, No. 4529, pp. 174-176.

Montesano, R., L. Orci, and P. Vassalli. Nov. 1983. "In Vitro Rapid Organization of Endothelial Cells into Capillary-like Networks Is Promoted by Collagen Matrices." *The Journal of Cell Biology*. vol. 97, pp. 1648-1652.

Pierschbacher, Michael D. and Erkki Ruoslahti. May 3, 1984. "Cell Attachment Activity of Fibronectin Can Be Duplicated by Small Synthetic Fragments of the Molecule." *Nature*. vol. 309, pp. 30-33.

Landis, W. J. and J. R. Martin. Apr.-Jun. 1984. "X-Ray Photoelectron Spectroscopy Applied to Gold-Decorated Mineral Standards of Biological Interest." *J. Vac. Sci. Technol*. vol. A 2, No. 2, pp. 1108-1111.

Thompson, Nancy L., Adrienne A. Brian, and Harden M. McConnell. 1984. "Covalent Linkage of a Synthetic Peptide to a Fluorescent Phospholipid and Its Incorporation into Supported Phospholipid Monolayers." *Biochimica et Biophysica Acta*. vol. 772, pp. 10-19.

Yamada, Kimiho, Hirotaka Ihara, Toshio Ide, Takanori Fukumoto, and Chuichi Hirayama. 1984. "Formation of Helical Super Structure from Single-Walled Bilayers by Amphiphiles with Oligo-L-Glutamic Acid-Head Group." *Chemistry Letters*. No. 10, pp. 1713-1716.

Addadi, L. and S. Weiner. Jun. 15, 1985. "Interactions Between Acidic Proteins and Crystals: Stereochemical Requirements in Biomineralization." *Proceedings of the National Academy of Sciences of the United States of America*. vol. 82, No. 12, pp. 4110-4114.

"Public Health Service Policy on Humane Care and Use of Laboratory Animals." Sep. 1986. Office for Protection from Research Risks (OPRR), National Institutes of Health.

Weiner, Stephen and Wolfie Traub. Oct. 1986. "Organization of Hydroxyapatite Crystals Within Collagen Fibrils." *FEBS Letters*. vol. 206, No. 2, pp. 262-266.

Maim, Stephen, John P. Hannington, and R. J. P. Williams. Dec. 11, 1986. "Phospholipid Vesicles as a Model System for Biomineralization." *Nature*. vol. 324, pp. 565-567.

Krimm, Samuel and Jagdeesh Bandekar. 1986. "Vibrational Spectroscopy and Conformation of Peptides, Polypeptides, and Proteins." *Advances in Protein Chemistry*. vol. 38, pp. 181-364.

de Groot, K., R. Geesink, C. P. A. T. Klein, and P. Serekian. Dec. 1987. "Plasma Sprayed Coatings of Hydroxylapatite." *Journal of Biomedical Materials Research*. vol. 21, No. 12, pp. 1375-1381.

Bresnahan, J. C., M. S. Beattie, F. D. Todd III, and D. H. Noyes. 1987. "A Behavioral and Anatomical Analysis of Spinal Cord Injury Produced by a Feedback-Controlled Impaction Device." *Experimental Neurology*. vol. 95, pp. 548-570.

Moscatelli, David. 1987. "High and Low Affinity Binding Sites for Basic Fibroblast Growth Factor on Cultured Cells: Absence of a Role for Low Affinity Binding in the Stimulation of Plasminogen Activator Production by Bovine Capillary Endothelial Cells." *Journal of Cellular Physiology*. vol. 131, pp. 123-130.

Lambert, Joseph B., Herbert F. Shurvell, David A. Lightner, and R. Graham Cooks. 1987. "Group Frequencies: Infrared and Raman." *Introduction to Organic Spectroscopy*. New York: Macmillan Publishing Company. pp. 169-182.

Cook, Stephen D., Kevin A. Thomas, John F. Kay, and Michael Jarcho. Jul. 1988. "Hydroxyapatite-Coated Titanium for Orthopedic Implant Applications." *Clinical Orthopaedics and Related Research*. No. 232, pp. 225-243.

Saksela, Olli, David Moscatelli, Andreas Sommer, and Daniel B. Rifkin. Aug. 1988. "Endothelial Cell-Derived Heparan Sulfate Binds Basic Fibroblast Growth Factor and Protects It from Proteolytic Degradation." *The Journal of Cell Biology*. vol. 107, pp. 743-751.

Cardin, Alan D. and H. J. R. Weintraub. Jan./Feb. 1989. "Molecular Modeling of Protein-Glycosaminoglycan Interactions." *Arteriosclerosis*. vol. 9, No. 1, pp. 21-32.

Oonishi, H., M. Yamamoto, H. Ishimaru, E. Tsuji, S. Kuskitani, M. Aono, and Y. Ukon. Mar. 1989. "The Effect of Hydroxyapatite Coating on Bone Growth into Porous Titanium Alloy Implants." *The Journal of Bone and Joint Surgery*. vol. 71-B, No. 2, pp. 213-216.

Friedmann, Theodore. Jun. 16, 1989. "Progress Toward Human Gene Therapy." *Science*. vol. 244, No. 4910, pp. 1275-1281.

Traub, Wolfie, Talmon Arad, and Stephen Weiner. Dec. 15, 1989. "Three-Dimensional Ordered Distribution of Crystals in Turkey Tendon Collagen Fibers." *Proceedings of the National Academy of Sciences of the United States of America*. vol. 86, No. 24, pp. 9822-9826.

Knorr, Reinhard, Arnold Trzeciak, Willi Bannwarth, and Dieter Gillessen. 1989. "New Coupling Reagents in Peptide Chemistry." *Tetrahedron Letters*. vol. 30, No. 15, pp. 1927-1930.

Sambrook, Joseph, Edward F. Fritsch, and Thomas Maniatis. 1989. "Genes Encoding Selectable Markers." *Molecular Cloning: A Laboratory Manual*. 2nd ed. New York: Cold Spring Harbor Laboratory Press. pp. 16.9-16.15.

Veis, A. 1989. "Biochemical Studies of Vertebrate Tooth Mineralization." *Biomineralization*. S. Maim, J. Webb, and R. J. P. Williams, editors. Weinheim, Federal Republic of Germany: VCH Verlagsgesellschaft and New York: VCH Publishers. pp. 189-222.

Schnell, Lisa and Martin E. Schwab. Jan. 18, 1990. "Axonal Regeneration in the Rat Spinal Cord Produced by an Antibody Against Myelin-Associated Neurite Growth Inhibitors." *Nature*. vol. 343, pp. 269-272.

Ahn, Sang Tae and Thomas A. Mustoe. Jan. 1990. "Effects of Ischemia on Ulcer Wound Healing: A New Model in the Rabbit Ear." *Annals of Plastic Surgery*. vol. 24, No. 1, pp. 17-23.

Van de Pol, Frans C. M. Dec. 1990. "Thin-Film ZnO—Properties and Applications." *Ceramic Bulletin*. vol. 69, No. 12, pp. 1959-1965.

Addadi, L., A. Berman, J. Moradian-Oldak, and S. Weiner. Dec. 28, 1990. "Tuning of Crystal Nucleation and Growth by Proteins: Molecular Interactions at Solid-Liquid Interfaces in Biomineralization." *Croatica Chemica Acta*. vol. 63, No. 3, pp. 539-544.

Sukenik, Chaim N., Natarajan Balachander, Lloyd A. Culp, Kristine Lewandowska, and Katherine Merritt. 1990. "Modulation of Cell Adhesion by Modification of Titanium Surfaces with Covalently Attached Self-Assembled Monolayers." *Journal of Biomedical Materials Research*. vol. 24, pp. 1307-1323.

Fields, C. G., D. H. Lloyd, R. L. Macdonald, K. M. Otteson, and R. L. Noble. Mar./Apr. 1991. "HBTU Activation for Automated Fmoc Solid-Phase Peptide Synthesis." *Peptide Research*. vol. 4, No. 2, pp. 95-101.

Murata, Masayuki, Satoshi Kagiwada, Sho Takahashi, and Shun-ichi Ohnishi. Aug. 5, 1991. "Membrane Fusion Induced by Mutual Interaction of the Two Charge-Reversed Amphiphilic Peptides at Neutral pH." *The Journal of Biological Chemistry*. vol. 56, No. 22, pp. 14353-14358.

Harris, Robin, Editor. 1991. *Electron Microscopy in Biology: A Practical Approach*. New York: Oxford University Press.

Jackson, David Y., David S. King, Jean Chmielewski, Sunil Singh, and Peter G. Schultz. 1991. "General Approach to the Synthesis of Short α-Helical Peptides." *Journal of the American Chemical Society*. vol. 113, pp. 9391-9392.

Polverini, Peter J., Noel P. Bouck, and Farzan Rastinejad. 1991. "Assay and Purification of Naturally Occurring Inhibitor of Angiogenesis." *Methods in Enzymology*. vol. 198, pp. 440-450.

Weiner, Stephen and Wolfie Traub. Feb. 1992. "Bone Structure: From Angstroms to Microns." *The FASEB Journal*. vol. 6, pp. 879-885.

Nomizu, Motoyoshi, Atsushi Utani, Norio Shiraishi, Maura C. Kibbey, Yoshihiko Yamada, and Peter P. Roller. Jul. 15, 1992. "The All-D-Configuration Segment Containing the IKVAV Sequence of Laminin A Chain Has Similar Activities to the All-L-Peptide in Vitro and in Vivo." *The Journal of Biological Chemistry*. vol. 267, No. 20, pp. 14118-14121.

Addadi, Lia and Stephen Weiner. 1992. "Control and Design Principles in Biological Mineralization." *Angew. Chem. Int. Ed. Engl.* vol. 31, pp. 153-169.

Beresford, J. N., J. H. Bennett, C. Devlin, P. S. Leboy, and M. E. Owen. 1992. "Evidence for an Inverse Relationship Between the Differentiation of Adipocytic and Osteogenic Cells in Rat Marrow Stromal Cell Cultures." *Journal of Cell Science*. vol. 102, pp. 341-351.

Cook, Stephen D., Kevin A. Thomas, Jeanette E. Dalton, Todd K. Volkman, Thomas S. Whitecloud III, and John F. Kay. 1992. "Hydroxylapatite Coating of Porous Implants Improves Bone Ingrowth and Interface Attachment Strength." *Journal of Biomedical Materials Research*. vol. 26, pp. 989-1001.

Geahlen, Robert L., G. Marc Loudon, Lisa A. Paige, and David Lloyd. 1992. "A General Method for Preparation of Peptides Biotinylated at the Carboxy Terminus." *Analytical Biochemistry*. vol. 202, pp. 68-70.

Ghadiri, M. Reza, Christopher Soares, and Chong Choi. 1992. "Design of an Artificial Four-Helix Bundle Metalloprotein via a Novel Ruthenium(II)-Assisted Self-Assembly Process." *Journal of the American Chemical Society*. vol. 114, No. 10, pp. 4000-4002.

Kunitake, Toyoki. 1992. "Synthetic Bilayer Membranes: Molecular Design, Self-Organization, and Application." *Angew. Chem. Int. Ed. Engl.* vol. 31, pp. 709-726.

Stupp, Samuel I. and Glenn W. Ciegler. 1992. "Organoapatites: Materials for Artificial Bone. I. Synthesis and Microstructure." *Journal of Biomedical Materials Research*. vol. 26, pp. 169-183.

Surewicz, Witold K., Henry H. Mantsch, and Dennis Chapman Jan. 19, 1993. "Determination of Protein Secondary Structure by Fourier Transform Infrared Spectroscopy: A Critical Assessment" *Biochemistry*. vol. 32, No. 2, pp. 389-394.

Zhang, Shuguang, Todd Holmes, Curtis Lockshin, and Alexander Rich. Apr. 15, 1993. "Spontaneous Assembly of a Self-Complementary Oligopeptide to Form a Stable Macroscopic Membrane." *Proceedings of the National Academy of Sciences of the United States of America*. vol. 90, No. 8, pp. 3334-3338.

Langer, Robert and Joseph P. Vacanti. May 14, 1993. "Tissue Engineering." *Science*. vol. 260, No. 5110, pp. 920-926.

Mulligan, Richard C. May 14, 1993. "The Basic Science of Gene Therapy." *Science*. vol. 260, No. 5110, pp. 926-932.

Massas, R., S. Pitaru, and M. M. Weinreb. Jun. 1993. "The Effects of Titanium and Hydroxyapatite on Osteoblastic Expression and Proliferation in Rat Parietal Bone Cultures." *Journal of Dental Research*. vol. 72, No. 6, pp. 1005-1008.

Archibald, Douglas D. and Stephen Mann. Jul. 29, 1993. "Template Mineralization of Self-Assembled Anisotropic Lipid Microstructures." *Nature*. vol. 364, pp. 430-433.

Atala, Anthony, Linda G. Cima, Wooseob Kim, Keith T. Paige, Joseph P. Vacanti, Alan B. Retik, and Charles A. Vacanti. Aug. 1993. "Injectable Alginate Seeded with Chondrocytes as a Potential Treatment for Vesicoureteral Reflux." *The Journal of Urology*. vol. 150, No. 2, pp. 745-747.

Nomizu, Motoyoshi, Keizo Yamamura, Hynda K. Kleinman, and Yoshihiko Yamada. Aug. 1, 1993. "Multimeric Forms of Tyr-Ile-Gly-Ser-Arg (YIGSR) Peptide Enhance the Inhibition of Tumor Growth and Metastasis." *Cancer Research*. vol. 53, pp. 3459-3461.

Ross-Murphy, S. B. and K. P. Shatwell. May-Aug. 1993. "Polysaccharide Strong and Weak Gels." *Biorheology*. vol. 30, Nos. 3 & 4, pp. 217-227.

Margalit, Hanah, Nurit Fischer, and Shmuel A. Ben-Sasson. Sep. 15, 1993. "Comparative Analysis of Structurally Defined Heparin Binding Sequences Reveals a Distinct Spatial Distribution of Basic Residues." *The Journal of Biological Chemistry*. vol. 268, No. 26, pp. 19228-19231.

Kibbey, Maura C., Mathias Jucker, Benjamin S. Weeks, Rachael L. Neve, Wiliam E. Van Nostrand, and Hynda K. Kleinman Nov. 1993. "β-Amyloid Precursor Protein Binds to the Neurite-Promoting IKVAV Site of Laminin." *Proc. Natl. Acad. Sci. U.S.A*. vol. 90, pp. 10150-10153.

Fowler, Bruce O., Milenko Marković, and Walter E. Brown. 1993. "Octacalcium Phosphate. 3. Infrared and Raman Vibrational Spectra." *Chem. Mater*. vol. 5, No. 10, pp. 1417-1423.

Fuhrhop, Jürgen-Hhuich, Dragan Spiroski, and Christoph Boettcher. 1993. "Molecular Monolayer Rods and Tubules Made of α-(L-Lysine),ω-(Amino) Bolaamphiphiles." *Journal of the American Chemical Society*. vol. 115, No. 4, pp. 1600-1601.

Graham, Stephan and Paul W. Brown. 1993. "The Low Temperature Formation of Octacalcium Phosphate." *Journal of Crystal Growth*. vol. 132, pp. 215-225.

Shimizu, Toshimi and Masakatsu Hato. 1993. "Self-Assembling Properties of Synthetic Peptidic Lipids." *Biochimica et Biophysica Acta*. vol. 1147, pp. 50-58.

Stupp, Samuel I., Jacqueline A. Hanson, Jo Ann Eurell, Glenn W. Ciegler, and Ann Johnson. 1993. "Organoapatites: Materials for Artifical Bone. III. Biological Testing." *Journal of Biomedical Materials Research*. vol. 27, pp. 301-311.

Stupp, Samuel I., George C. Mejicano, and Jacqueline A. Hanson. 1993. "Organoapatites: Materials for Artificial Bone. II. Hardening Reactions and Properties." *Journal of Biomedical Materials Research*. vol. 27, pp. 289-299.

Wald, Heidi L., Georgios Sarakinos, Michelle D. Lyman, Antonios G. Mikos, Joseph P. Vacanti, and Robert Langer. 1993. "Cell Seeding in Porous Transplantation Devices." *Biomaterials*. vol. 14, No. 4, pp. 270-278.

Walsh, Dominic, Joanne L. Kingston, Brigid R. Heywood, and Stephen Mann. 1993. "Influence of Monosaccharides and Related Molecules on the Morphology of Hydroxyapatite." *Journal of Crystal Growth*. vol. 133, pp. 1-12.

Wang, B. C., T. M. Lee, E. Chang, and C. Y. Yang. 1993. "The Shear Strength and the Failure Mode of Plasma-Sprayed Hydroxyapatite Coating to Bone: The Effect of Coating Thickness." *Journal of Biomedical Materials Research*. vol. 27, pp. 1315-1327.

San Antonio, James D., Arthur D. Lander, Morris J. Karnovsky, and Henry S. Slayter. Jun. 1994. "Mapping the Heparin-Binding Sites on Type I Collagen Monomers and Fibrils." *The Journal of Cell Biology*. vol. 125, No. 5, pp. 1179-1188.

Ban, S., S. Maruno, H. Iwata, and H. Itoh. 1994. "Calcium Phosphate Precipitation on the Surface of HA-G-Ti Composite Under Physiologic Conditions." *Journal of Biomedical Materials Research*. vol. 28, pp. 65-71.

de Bruijn, J. D., Y. P. Bovell, and C. A. van Blitterswijk. 1994. "Structural Arrangements at the Interface Between Plasma Sprayed Calcium Phosphates and Bone." *Biomaterials*. vol. 15, No. 7, pp. 543-550.

Hunter, Graeme K. and Harvey A. Goldberg. 1994. "Modulation of Crystal Formation by Bone Phosphoproteins: Role of Glutamic Acid-Rich Sequences in the Nucleation of Hydroxyapatite by Bone Sialoprotein." *Biochem. J*. vol. 302, pp. 175-179.

Klein, C. P. A. T., J. G. C. Wolke, J. M. A. de Blieck-Hogervorst, and K. de Groot. 1994. "Calcium Phosphate Plasma-Sprayed Coatings and Their Stability: An in Vivo Study." *Journal of Biomedical Materials Research*. vol. 28, pp. 909-917.

Margomenou-Leonidopoulou, G. 1994. "Thermotropic Mesophases of Ionic Amphiphiles. II. Ionic Amphiphiles in Aqueous Media." *Journal of Thermal Analysis*. vol. 42, pp. 1041-1061.

Mikos, Antonios G., Michelle D. Lyman, Lisa E. Freed, and Robert Langer. 1994. "Wetting of Poly(L-Lactic Acid) and Poly(DL-Lactic-co-glycolic Acid) Foams for Tissue Culture." *Biomaterials*. vol. 15, No. 1, pp. 55-58.

Bond, G. M., R. H. Richman, and W. P. McNaughton. Jun. 1995. "Mimicry of Natural Material Designs and Processes." *Journal of Materials Engineering and Performance*. vol. 4, No. 3, pp. 334-345.

Hubbell, Jeffrey A. Jun. 1995. "Biomaterials in Tissue Engineering." *Bio/technology*. vol. 13, pp. 565-576.

Fromm, J. R., R. E. Hileman, E. E. O. Caldwell, J. M. Weiler, and R. J. Linhardt. Nov. 10, 1995. "Differences in the Interaction of Heparin with Arginine and Lysine and the Importance of these Basic Amino Acids in the Binding of Heparin to Acidic Fibroblast Growth Factor." *Archives of Biochemistry and Biophysics*. vol. 323, No. 2, pp. 279-287.

Wakitani, Shigeyuki, Tomoyuki Saito, and Arnold I. Caplan. Dec. 1995. "Myogenic Cells Derived from Rat Bone Marrow Mesenchymal Stem Cells Exposed to 5-Azacytidine." *Muscle & Nerve*. vol. 18, pp. 1417-1426.

Aletras, Alexios, Kleomenis Barlos, Dimitrios Gatos, Sophia Koutsogianni, and Petros Mamos. 1995. "Preparation of the Very Acid-Sensitive Fmoc-Lys(Mtt)-OH." *International Journal of Peptide & Protein Research*. vol. 45, pp. 488-496.

Berndt, Peter, Gregg B. Fields, and Matthew Tirrell. 1995. "Synthetic Lipidation of Peptides and Amino Acids: Monolayer Structure and Properties." *Journal of the American Chemical Society*. vol. 117, No. 37, pp. 9515-9522.

Gage, Fred H., Jasodhara Ray, and Lisa J. Fisher. 1995. "Isolation, Characterization, and Use of Stem Cells from the CNS." *Annual Review of Neuroscience*. vol. 18, pp. 159-192.

Jackowski, Andre. 1995. "Neural Injury Repair: Hope for the Future as Barriers to Effective CNS Regeneration Become Clearer." *J. Neurosurg*. vol. 9, pp. 303-317.

Nomizu, Motoyoshi, Benjamin S. Weeks, Christi A. Weston, Woo Hoo Kim, Hynda K. Kleinman, and Yoshihiko Yamada. 1995. "Structure-Activity Study of a Laminin α1 Chain Active Peptide Segment Ile-Lys-Val-Ala-Val (IKVAV)." *FEBS Letters*. vol. 365, pp. 227-231.

Saito, Tomoyuki, James E. Dennis, Donald P. Lennon, Randell G. Young, and Arnold I. Caplan. 1995. "Myogenic Expression of Mesenchymal Stem Cells Within Myotubes of mdx Mice in Vitro and in Vivo." *Tissue Engineering*. vol. 1, No. 4, pp. 327-343.

Sasanuma, Michio. 1995. "Optical Processes in ZnO." *J. Phys.: Condens. Matter*. vol. 7, pp. 10029-10036.

Zhang, Shuguang, Todd C. Holmes, C. Michael DiPersio, Richard O. Hynes, Xing Su, and Alexander Rich. 1995. "Self-Complementary Oligopeptide Matrices Support Mammalian Cell Attachment." *Biomaterials*. vol. 16, No. 18, pp. 1385-1393.

Falini, Guiseppe, Shira Albeck, Steve Weiner, and Lia Addadi. Jan. 5, 1996. "Control of Aragonite or Calcite Polymorphism by Mollusk Shell Macromolecules." *Science*. vol. 271, No. 5245, pp. 67-69.

Alivisatos, A. P. Feb. 16, 1996. "Semiconductor Clusters, Nanocrystals, and Quantum Dots." *Science*. vol. 271, No. 5251, pp. 933-937.

Keyt, Bruce A., Lea T. Berleau, Hung V. Nguyen, Helen Chen, Henry Heinsohn, Richard Vandlen, and Napoleone Ferrara. Mar. 29, 1996. "The Carboxyl-terminal Domain (111-165) of Vascular Endothelial Growth Factor Is Critical for Its Mitogenic Potency." *The Journal of Biological Chemistry*. vol. 271, No. 13, pp. 7788-7795.

Oka, Kazunari, Masaaki Yamamoto, Toshiharu Nonaka, and Masamichi Tomonaga. Apr. 1996. "The Significance of Artificial Cerebrospinal Fluid as Perfusate and Endoneurosurgery." *Neurosurgery Online*. vol. 38, No. 4, pp. 733-736.

Belcher, A. M., X. H. Wu, R. J. Christensen, P. K. Hansma, G. D. Stucky, and D. E. Morse. May 2, 1996. "Control of Crystal Phase Switching and Orientation by Soluble Mullusc-Shell Proteins." *Nature*. vol. 381, pp. 56-58.

Hortelano, Gonzalo, Ayman Al-Hendy, Frederick A. Ofosu, and Patricia L. Chang. Jun. 15, 1996. "Delivery of Human Factor IX in Mice by Encapsulated Recombinant Myoblasts: A Novel Approach Towards Allogenic Gene Therapy of Hemophilia B." *Blood*. vol. 87, No. 12, pp. 5095-5103.

Sultzbaugh, K. J. and T. J. Speaker. Jul.-Aug. 1996. "A Method to Attach Lectins to the Surface of Spermine Alginate Microcapsules Based on the Avidin Biotin Interaction." *J. Microencapsulation*. vol. 13, No. 4, pp. 363-375.

Alivisatos, A. Paul, Kai P. Johnsson, Xiaogang Peng, Troy E. Wilson, Colin J. Loweth, Marcel P. Burchez Jr., and Peter G. Schultz. Aug. 15, 1996. "Organization of 'Nanocrystal Molecules' Using DNA." *Nature*. vol. 382, pp. 609-611.

George, Anne, Leslie Bannon, Boris Sabsay, Jerry W. Dillon, James Malone, Arthur Veis, Nancy A. Jenkins, Debra J. Gilbert, and Neal G. Copeland. Dec. 20, 1996. "The Carboxyl-terminal Domain of Phosphophoryn Contains Unique Extended Triplet Amino Acid Repeat Sequences Forming Ordered Carboxyl-Phosphate Interaction Ridges That May Be Essential in the Biomineralization Process." *The Journal of Biological Chemistry*. vol. 271, No. 51, pp. 32869-32873.

Basso, D. Michele, Michael S. Beattie, and Jacqueline C. Bresnahan. 1996. "Graded Histological and Locomotor Outcomes after Spinal Cord Contusion Using the NYU Weight-Drop Device Versus Transection." *Experimental Neurology*. vol. 139, pp. 244-256.

Burkett, Sandra L. and Stephen Maim. 1996. "Spatial Organization and Patterning of Gold Nanoparticles on Self-Assembled Biolipid Tubular Templates." *Chem. Commun*. pp. 321-322.

Hunter, Graeme K., Peter V. Hauschka, A. Robin Poole, Lawrence C. Rosenberg, and Harvey A. Goldberg. 1996. "Nucleation and Inhibition of Hydroxyapatite Formation by Mineralized Tissue Proteins." *Biochem. J*. vol. 317, pp. 59-64.

Karymov, Mikhail A., Karel Prochazka, John M. Mendenhall, Thomas J. Martin, Petr Munk, and Stephen E. Webber. 1996. "Chemical Attachment of Polystyrene-*block*-poly(methacrylic acid) Micelles on a Silicon Nitride Surface." *Langmuir*. vol. 12, No. 20, 4748-4753.

Landis, William J., Karen J. Hodgens, James Arena, Min Ja Song, and Bruce F. McEwen. 1996. "Structural Relations Between Collagen and Mineral in Bone as Determined by High Voltage Electron Microscopic Tomography." *Microscopy Research and Technique*. vol. 33, pp. 192-202.

Matsuzawa, Mieko, Forrest F. Weight, Richard S. Potember, and Päivi Liesi. 1996. "Directional Neurite Outgrowth and Axonal Differentiation of Embryonic Hippocampal Neurons Are Promoted by a Neurite Outgrowth Domain of the B2-Chain of Laminin" *Int. J. Devl. Neuroscience*. vol. 14, No. 3, pp. 283-295.

Mooney, David J., Daniel F. Baldwin, Nam P. Suh, Joseph P. Vacanti, and Robert Langer. 1996. "Novel Approach to Fabricate Porous Sponges of Poly(D,L-Lactic-co-glycolic Acid) Without the Use of Organic Solvents." *Biomaterials*. vol. 17, No. 14, pp. 1417-1422.

Rappolt, Michael and Gert Rapp. 1996. "Structure of the Stable and Metastable Ripple Phase of Dipalmitoylphosphatidylcholine." *Eur. Biophys. J*. vol. 24, pp. 381-386.

Ratner, Buddy D., Allan S. Hoffman, Frederick J. Schoen, and Jack E. Lemons, Editors. 1996. *Biomaterials Science: An Introduction to Materials in Medicine*. San Diego, CA: Academic Press.

Tam, James P. 1996. "Recent Advances in Multiple Antigen Peptides." *Journal of Immunological Methods*. vol. 196, pp. 17-32.

Ulman, Abraham. 1996. "Formation and Structure of Self-Assembled Monolayers." *Chemical Reviews*. vol. 96, No. 4, pp. 1533-1554.

Yu, Ying-Ching, Peter Berndt, Matthew Tirrell, and Gregg B. Fields. 1996. "Self-Assembling Amphiphiles for Construction of Protein Molecular Architecture." *Journal of the American Chemical Society*. vol. 118, No. 50, pp. 12515-12520.

Zarif, Leila, Ange Polidori, Bernard Pucci, Tadek Gulik-Krzywicki, André A. Pavia, and Jean G. Riess. 1996. "Effect of Chirality on the Formation of Tubules from Glycolipidic Amphiphiles." *Chemistry and Physics of Lipids*. vol. 79, pp. 165-170.

Aggeli, A., M. Bell, N. Boden, J. N. Keen, P. F. Knowles, T. C. B. McLeish, M. Pitkeathly, and S. E. Radford. Mar. 20, 1997. "Responsive Gels Formed by the Spontaneous Self-Assembly of Peptides into Polymeric β-Sheet Tapes." *Nature*. vol. 386, pp. 259-262.

Herr, Andrew B., David M. Ornitz, Ram Sasisekharan, Ganesh Venkataraman, and Gabriel Waksman. Jun. 27, 1997. "Heparin-Induced Self-Association of Fibroblast Growth Factor-2." *The Journal of Biological Chemistry*. vol. 272, No. 26, pp. 16382-16389.

Dimmeler, Stefanie and Andreas M. Zeiher. Aug. 1997. "Nitric Oxide and Apoptosis: Another Paradigm for the Double-Edged Role of Nitric Oxide." *Nitric Oxide: Biology and Chemistry*. vol. 1, No. 4, pp. 275-281.

Stupp, Samuel I. and Paul V. Braun. Aug. 29, 1997. "Molecular Manipulation of Microstructures: Biomaterials, Ceramics, and Semiconductors." *Science*. vol. 277, No. 5330, pp. 1242-1248.

Kaufmann, P. M., S. Heimrath, B. S. Kim, and D. J. Mooney. Sep./Oct. 1997. "Highly Porous Polymer Matrices as a Three-Dimensional Culture System for Hepatocytes." *Cell Transplantation*. vol. 6, No. 5, pp. 463-468.

Aggeli, Amalia, Mark Bell, Neville Boden, Jeff N. Keen, Tom C. B. McLeish, Irina Nyrkova, Sheena E. Radford, and Alexander Semenov. 1997. "Engineering of Peptide β-Sheet Nanotapes." *J. Mater. Chem*. vol. 7, No. 7, pp. 1135-1145.

Anderson, James M. and Matthew S. Shive. 1997. "Biodegradation and Biocompatibility of PLA and PLGA Microspheres." *Advanced Drug Delivery Reviews*. vol. 28, pp. 5-24.

Draget, Kurt Ingar, Gudmund Skjåk-Bræk, Olav Smidsrød. 1997. "Alginate Based New Materials." *International Journal of Biological Macromolecules*. vol. 21, pp. 47-55.

El-Ghannam, Ahmed, Paul Ducheyne, and Irving M. Shapiro. 1997. "Porous Bioactive Glass and Hydroxyapatite Ceramic Affect Bone Cell Function in Vitro Along Different Time Lines." *Journal of Biomedical Materials Research*. vol. 36, pp. 167-180.

Goveas, J. L. and S. T. Milner. 1997. "Dynamics of the Lamellar—Cylindrical Transition in Weakly Segregated Diblock Copolymer Melts." Macromolecules. vol. 30, No. 9, pp. 2605-2612.

Jaiswal, Neelam, Stephen E. Haynesworth, Arnold I. Caplan, and Scott P. Bruder. 1997. "Osteogenic Differentiation of Purified, Culture-Expanded Human Mesenchymal Stem Cells in Vitro." *Journal of Cellular Biochemistry*. vol. 64, pp. 295-312.

Munson, John B. and Stephen B. McMahon. 1997. "Effects of GDNF on Axotomized Sensory and Motor Neurons in Adult Rats." European Journal of Neuroscience. vol. 9, pp. 1126-1129.

Nehrer, Stefan, Howard A. Breinan, Arun Ramappa, Sonya Shortkroff, Gretchen Young, Tom Minas, Clement B. Sledge, Ioannis V. Yannas, and Myron Spector. 1997. "Canine Chondrocytes Seeded in Type I and Type II Collagen Implants Investigated in Vitro." *Journal of Biomedical Materials Research (Appl. Biomater.)*. vol. 38, pp. 95-104.

Maim, Stephen. 1997. "Biomineralization: The Form(id)able Part of Bioinorganic Chemistry!" *J. Chem. Soc., Dalton Trans*. pp. 3953-3961.

Norrby, Klas. 1997. "Angiogenesis: New Aspects Relating to Its Initiation and Control." *APMIS*. vol. 105, pp. 417-437.

Shimizu, Toshimi, Masaki Kogiso, and Mitsutoshi Masuda. 1997. "Noncovalent Formation of Polyglycine II-Type Structure by Hexagonal Self-Assembly of Linear Polymolecular Chains." *Journal of the Americal Chemical Society*. vol. 119, No. 26, pp. 6209-6210, S2-S17.

Smith, George P. and Valery A. Petrenko. 1997. "Phage Display." *Chemical Reviews*. vol. 97, No. 2, pp. 391-410.

Toyotama, Akiko, Shin-ichi Kugimiya, Masakatsu Yonese, Takatoshi Kinoshita, and Yoshiharu Tsujita. 1997. "Controllable Orientation of the Peptide-Based Surfactant at Air-Water Interface." *Chemistry Letters*. pp. 443-444.

Weiner, Stephen and Lia Addadi. 1997. "Design Strategies in Mineralized Biological Materials." *J. Mater. Chem.* vol. 7, No. 5, pp. 689-702.

Wellings, Donald A. and Eric Atherton. 1997. "Standard Fmoc Protocols." *Methods in Enzymology*. vol. 289, pp. 44-67.

Wen, H. B., J. G. C. Wolke, J. R. de Wijn, Q. Liu, F. Z. Cui, and K. de Groot. 1997. "Fast Precipitation of Calcium Phosphate Layers on Titanium Induced by Simple Chemical Treatments." *Biomaterials*. vol. 18, No. 22, pp. 1471-1478.

Yu, Ying-Ching, Teika Pakalns, Yoav DoH, James B. McCarthy, Matthew Tirrell, and Gregg B. Fields. 1997. "Construction of Biologically Active Protein Molecular Architecture Using Self-Assembling Peptide-Amphiphiles." *Methods in Enzymology*. vol. 289, pp. 571-587.

Zhitomirsky, I. and L. Gal-Or. 1997. "Electrophoretic Deposition of Hydroxyapatite." *Journal of Materials Science: Materials in Medicine*. pp. 213-219.

Veis, Arthur, Kuiru Wei, Charles Sfeir, Anne George, and James Malone. Jan. 1998. "Properties of the (DSS)$_n$ Triplet Repeat Domain of Rat Dentin Phosphophoryn." *European Journal of Oral Sciences*. vol. 106 (suppl. 1), pp. 234-238.

Pincus, David W., Robert R. Goodman, Richard A. R. Fraser, Maiken Nedergaard, and Steven A. Goldman. Apr. 1998. "Neural Stem and Progenitor Cells: A Strategy for Gene Therapy and Brain Repair." *Neurosurgery*. vol. 42, No. 4, pp. 858-867.

Ogiso, M., Y. Yamashita, and T. Matsumoto. Jun. 1998. "The Process of Physical Weakening and Dissolution of the HA-Coated Implant in Bone and Soft Tissue." *Journal of Dental Research*. vol. 77, No. 6, pp. 1426-1434.

Petka, Wendy A., James L. Harden, Kevin P. McGrath, Denis Wirtz, and David A. Tirrell. Jul. 17, 1998. "Reversible Hydrogels from Self-Assembling Artificial Proteins." *Science*. vol. 281, No. 5375, pp. 389-392.

Orgill, Dennis P., Charles Butler, John F. Regan, Mark S. Barlow, I. V. Yannas, and Carolyn C. Compton. Aug. 1998. "Vascularized Collagen-Glycosaminoglycan Matrix Provides a Dermal Substrate and Improves Take of Cultured Epithelial Autografts." *Plastic and Reconstructive Surgery*. vol. 102, No. 2, pp. 423-429.

Yu, Ying-Ching, Matthew Tirrell, and Gregg B. Fields. Oct. 7, 1998. "Minimal Lipidation Stabilizes Protein-Like Molecular Architecture." *Journal of the American Chemical Society*. vol. 120, No. 39, pp. 9979-9987.

Borkenhagen, M., J.-F. Clémence, H. Sigrist, and P. Aebischer. 1998. "Three-Dimensional Extracellular Matrix Engineering in the Nervous System." *Journal of Biomedical Materials Research*. vol. 40, pp. 392-400.

Brekke, John H. and Jeffrey M. Toth. 1998. "Principles of Tissue Engineering Applied to Programmable Osteogenesis." *Journal of Biomedical Materials Research (Appl. Biomater.)*. vol. 43, pp. 380-398.

Clemetson, K. J., and J. M. Clemetson. 1998. "Integrins and Cardiovascular Disease." CMLS Cellular and Molecular Life Sciences. vol. 54, pp. 502-513.

Fernandez, A., M. A. Alsina, I. Haro, R. Galantai, and F. Reig. 1998. "Synthesis and Physicochemical Characterization of Cyclic Laminin Related Peptides." Langmuir. vol. 14, No. 13, pp. 3625-3630.

Fields, Gregg B., Janelle L. Lauer, Yoav Dori, Pilar Foms, Ying-Ching Yu, and Matthew Tirrell. 1998. "Proteinlike Molecular Architecture: Biomaterial Applications for Inducing Cellular Receptor Binding and Signal Transduction." *Biopolymers (Peptide Science)*. vol. 47, pp. 143-151.

Gu, Keni, Syweren R. Chang, Matt S. Slaven, Brian H. Clarkson, R. Bruce Rutherford, and Helena H. Ritchie. 1998. "Human Dentin Phosphophoryn Nucleotide and Amino Acid Sequence." *European Journal of Oral Sciences*. vol. 106, pp. 1043-1047.

Hartgerink, Jeffrey D., Thomas D. Clark, and M. Reza Ghadiri. 1998. "Peptide Nanotubes and Beyond." *Chem. Eur. J.* vol. 4, No. 8, pp. 1367-1372.

Johnstone, Brian, Thomas M. Hering, Arnold I. Caplan, Victor M. Goldberg, and Jung U. Yoo. 1998. "In Vitro Chondrogenesis of Bone Marrow-Derived Mesenchymal Progenitor Cells." *Experimental Cell Research*. vol. 238, pp. 265-272.

Kawasaki, M., A. Ohtomo, I. Ohkubo, H. Koinuma, Z. K. Tang, P. Yu, G. K. L. Wong, B. P. Zhang, and Y. Segawa. 1998. "Excitonic Ultraviolet Laser Emission at Room Temperature from Naturally Made Cavity in ZnO Nanocrytal Thin Films." *Materials Science and Engineering*. vol. B56, pp. 239-245.

Kogiso, Masaki, Satomi Ohnishi, Kiyoshi Yase, Mitsutoshi Masuda, and Toshimi Shimizu 1998. "Dicarboxylic Oligopeptide Bolaamphiphiles: Proton-Triggered Self-Assembly of Microtubes with Loose Solid Surfaces." *Langmuir*. vol. 14, No. 18, pp. 4978-4986, S1-S7.

Kogiso, Masaki, Takeshi Hanada, Kiyoshi Yase, and Toshimi Shimizu 1998. "Intralayer Hydrogen-Bond-Directed Self-Assembly of Nano-Fibers from Dicarboxylic Valylvaline Bolaamphiphiles." *Chem. Comm.* pp. 1791-1792.

Li, Panjian and Paul Ducheyne. 1998. "Quasi-Biological Apatite Film Induced by Titanium in a Simulated Body Fluid." *Journal of Biomedical Materials Research*. vol. 41, pp. 341-348.

Nanci, A., J. D. Wuest, L. Peru, P. Brunet, V. Sharma, S. Zalzal, and M. D. McKee. 1998. "Chemical Modification of Titanium Surfaces for Covalent Attachment of Biological Molecules." *Journal of Biomedical Materials Research*. vol. 40, pp. 324-335.

Tsui, Y. C., C. Doyle, and T. W. Clyne. 1998. "Plasma Sprayed Hydroxyapatite Coatings on Titanium Substrates Part 2: Optimisation of Coating Properties." *Biomaterials*. vol. 19, pp. 2031-2043.

Weiner, S. and H. D. Wagner. 1998. "The Material Bone: Structure-Mechanical Function Relations." *Annu. Rev. Mater. Sci.* vol. 28, pp. 271-298.

Wen, H. B., J. R. de Wijn, F. Z. Cui, and K. de Groot. 1998. "Preparation of Calcium Phosphate Coatings on Titanium Implant Materials by Simple Chemistry." *Journal of Biomedical Materials Research*. vol. 41, pp. 227-236.

Wheeler, Donna L., David L. Chamberland, John M. Schmitt, David C. Buck, John H. Brekke, Jeffrey O. Hollinger, S.-P. Joh, and K.-W. Suh. 1998. "Radiomorphometry and Biomechanical Assessment of Recombinant Human Bone Morphogenetic Protein 2 and Polymer in Rabbit Radius Ostectomy Model." *Journal of Biomedical Materials Research (Appl. Biomater.)*. vol. 43, pp. 365-373.

Wolke, J. G. C., K. de Groot, and J. A. Jansen. 1998. "In Vivo Dissolution Behavior of Various RF Magnetron Sputtered Ca-P Coatings." Journal of Biomedical Materials Research. vol. 39, pp. 524-530.

Xiao, Shou-Jun, Marcus Textor, and Nicholas D. Spencer. 1998. "Covalent Attachment of Cell-Adhesive, (Arg-Gly-Asp)-Containing Peptides to Titanium Surfaces." *Langmuir*. vol. 14, No. 19, pp. 5507-5516.

Xu, Guofeng, Nan Yao, Ilhan A. Aksay, and John T. Groves. 1998. "Biomimetic Synthesis of Macroscopic-Scale Calcium Carbonate Thin Films. Evidence for a Multistep Assembly Process." *Journal of the American Chemical Society*. vol. 120, No. 46, pp. 11977-11985.

Yamada, Norihiro, Katsuhiko Ariga, Masanobu Naito, Kazuhiro Matsubara, and Emiko Koyama. 1998. "Regulation of β-Sheet Structures Within Amyloid-Like β-Sheet Assemblage from Tripeptide Derivatives." *Journal of the American Chemical Society*. vol. 120, No. 47, pp. 12192-12199.

Chusuei, Charles C., D. Wayne Goodman, Michael J. Van Stipdonk, Dina R. Justes, and Emile A. Schweikert. Jan. 1, 1999. "Calcium Phosphate Phase Identification Using XPS and Time-of-Flight Cluster SIMS." *Analytical Chemistry*. vol. 71, No. 1, pp. 149-153.

Zubarev, Eugene R., Martin U. Pratte, Leiming Li, and Samuel I. Shipp. Jan. 22, 1999. "Conversion of Supramolecular Clusters to Macromolecular Objects." *Science*. vol. 283, pp. 523-526.

Won, You-Yeon, H. Ted Davis, and Frank S. Bates. Feb. 12, 1999. "Giant Wormlike Rubber Micelles." *Science*. vol. 283, No. 5404, pp. 960-963.

Corral, Claudio J., Aamir Siddiqui, Liancun Wu, Catherine L. Farrell, David Lyons, and Thomas A. Mustoe. Feb. 1999. "Vascular Endothelial Growth Factor Is More Important Than Basic Fibroblastic Growth Factor During Ischemic Wound Healing." *Arch. Surg.* vol. 134, pp. 200-205.

Wheeler, B. C., J. M. Corey, G. J. Brewer, and D. W. Branch. Feb. 1999. "Microcontact Printing for Precise Control of Nerve Cell Growth in Culture." *Journal of Biomechanical Engineering*. vol. 121, pp. 73-78.

Cao, H., Y. G. Zhao, S. T. Ho, E. W. Seelig, Q. H. Wang, and R. P. H. Chang. Mar. 15, 1999. "Random Laser Action in Semiconductor Powder." *Physical Review Letters*. vol. 82, No. 11, pp. 2278-2281.

Aizenberg, Joanna, Andrew J. Black, and George M. Whitesides. Apr. 8, 1999. "Control of Crystal Nucleation by Patterned Self-Assembled Monolayers." *Nature*. vol. 398, pp. 495-498.

Niklason, L. E., J. Gao, W. M. Abbott, K. K. Hirschi, S. Houser, R. Marini, and R. Langer. Apr. 16, 1999. "Functional Arteries Grown in Vitro." *Science*. vol. 284, pp. 489-493.

Hahn, Jungseok and Stephen E. Webber. Apr. 1999. "Modification of Surfaces by Covalent Attachment of Polymer Micelles." *Macromolecular Symposia*. vol. 139, pp. 39-47.

Liu, Yi, Duckhyun Kim, B. Timothy Himes, Stella Y. Chow, Timothy Schallert, Marion Murray, Alan Tessler, and Itzhak Fischer. Jun. 1, 1999. "Transplants of Fibroblasts Genetically Modified to Express BDNF Promote Regeneration of Adult Rat Rubrospinal Axons and Recovery of Forelimb Function." *The Journal of Neuroscience*. vol. 19, No. 11, pp. 4370-4387.

Mehler, Mark F. and John A. Kessler. Jul. 1999. "Progenitor Cell Biology: Implications for Neural Regeneration." *Arch. Neurol*. vol. 56, pp. 780-784.

Tirrell, M. Oct. 27, 1999. "Biofunctionalization of Surfaces with Peptide Amphiphiles." *AVS: Science & Technology*. Invited Paper BI-WeM7.

McDonald, John W., Xiao-Zhong Liu, Yun Qu, Su Liu, Shannon K. Mickey, Dorothy Turetsky, David I. Gottlieb, and Dennis W. Choi. Dec. 1999. "Transplanted Embryonic Stem Cells Survive, Differentiate and Promote Recovery in Injured Rat Spinal Cord." *Nature Medicine*. vol. 5, No. 12, pp. 1410-1412.

Bradt, Jens-Hilmar, Michael Mertig, Angelika Teresiak, and Wolfgang Pompe. 1999. "Biomimetic Mineralization of Collagen by Combined Fibril Assembly and Calcium Phosphate Formation." *Chem. Mater*. vol. 11, No. 10, pp. 2694-2701.

Braun, Paul V. and Samuel I. Stupp. 1999. "CdS Mineralization of Hexagonal, Lamellar, and Cubic Lyotropic Liquid Crystals." *Materials Research Bulletin*. vol. 34, No. 3, pp. 463-469.

Butler, C. E., I. V. Yannas, C. C. Compton, C. A. Correia, and D. P. Orgill. 1999. "Comparison of Cultured and Uncultured Keratinocytes Seeded into a Collagen-GAG Matrix for Skin Replacements." *British Journal of Plastic Surgery*. vol. 52, pp. 127-132.

Chai, C. S. and B. Ben-Nissan. 1999. "Bioactive Nanocrystalline Sol-Gel Hydroxyapatite Coatings." *Journal of Materials Science: Materials in Medicine*. vol. 10, pp. 465-469.

Clark, Thomas D., Kenji Kobayashi, and M. Reza Ghadiri. 1999. "Covalent Capture and Stabilization of Cylindrical β-Sheet Peptide Assemblies." *Chem. Eur. J*. vol. 5, No. 2, pp. 782-792.

Cornish, J., K. E. Callon, C. Q.-X. Lin, C. L. Xiao, T. B. Mulvey, G. J. S. Cooper, and I. R. Reid. 1999. "Trifluoroacetate, a Contaminant in Purified Proteins, Inhibits Proliferation of Osteoblasts and Chondrocytes." *Am. J. Physiol. Endocrinol. Metab*. vol. 277, pp. 779-783.

Emoto, Kazunori, Yukio Nagasaki, and Kazunori Kataoka. 1999. "Coating of Surfaces with Stabilized Reactive Micelles from Poly-(ethylene glycol)—Poly(DL-Lactic Acid) Block Copolymer." *Langmuir*. vol. 15, No. 16, pp. 5212-5218.

Fields, Gregg B. 1999. "Induction of Protein-like Molecular Architecture by Self-Assembly Processes." *Bioorganic & Medicinal Chemistry*. vol. 7, pp. 75-81.

Haynes, Andrew J., Wei-Qun Huang, Jamie Mallah, Dajun Yang, Marc E. Lippman, and Lu-Yuan Li. 1999. "Angiopoietin-1 and Its Receptor Tie-2 Participate in the Regulation of Capillary-like Tubule Formation and Survival of Endothelial Cells." *Microvascular Research*. vol. 58, pp. 224-237.

Hwang, Julia J., Kevin Jaeger, James Hancock, and Samuel I. Stupp. 1999. "Organoapatite Growth on an Orthopedic Alloy Surface." *Journal of Biomedical Materials Research*. vol. 47, pp. 504-515.

Ignjatović, Nenad, Simonida Tomić, Momčilo Dakić, Miroslav Miljković, Milenko Plavšić, and Dragan Uskoković. 1999. "Synthesis and Properties of Hydroxyapatite/Poly-L-Lactide Composite Biomaterials." *Biomaterials*. vol. 20, pp. 809-816.

Lee, Kevin J. and Thomas M. Jessell. 1999. "The Specification of Dorsal Cell Fates in the Vertebrate Central Nervous System." *Annual Review of Neuroscience*. vol. 22, pp. 261-294.

Lee, Kyujin C., Paul A. Carlson, Alex S. Goldstein, Paul Yager, and Michael H. Gelb. 1999. "Protection of a Decapeptide from Proteolytic Cleavage by Lipidation and Self-Assembly into High-Axial-Ratio Microstructures: A Kinetic and Structural Study." *Langmuir*. vol. 15, No. 17, pp. 5500-5508.

Mao, Chuanbin, Hengde Li, Fuzhai Cui, Chunlai Ma, and Qinglin Feng. 1999. "Oriented Growth of Phosphates on Polycrystalline Titanium in a Process Mimicking Biomineralization." *Journal of Crystal Growth*. vol. 206, pp. 308-321.

Miyaji, Fumiaki, Hyun-Min Kim, Shinichi Banda, Tadashi Kokubo, and Takashi Nakamura 1999. "Bonelike Apatite Coating on Organic Polymers: Novel Nucleation Process Using Sodium Silicate Solution." *Biomaterials*. vol. 20, pp. 913-919.

Pakalns, Teika, Kraig L. Haverstick, Gregg B. Fields, James B. McCarthy, Daniel L. Mooradian, and Matthew Tirrell. 1999. "Cellular Recognition of Synthetic Peptide Amphiphiles in Self-Assembled Monolayer Films." *Biomaterials*. vol. 20, pp. 2265-2279.

Pittenger, Mark F., Alastair M. Mackay, Stephen C. Beck, Rama K. Jaiswal, Robin Douglas, Joseph D. Mosca, Mark A. Moorman, Donald W. Simonetti, Stewart Craig, and Daniel R. Marshak. Apr. 2, 1999. "Multilineage Potential of Adult Human Mesenchymal Stem Cells." *Science*. vol. 284, pp. 143-147.

Rezania, Alireza, Robert Johnson, Anthony R. Lefkow, and Kevin E. Healy. 1999. "Bioactivation of Metal Oxide Surfaces. 1. Surface Characterization and Cell Response." *Langmuir*. vol. 15, No. 20, pp. 6931-6939.

Rowley, Jon A., Gerard Madlambayan, and David J. Mooney. 1999. "Alginate Hydrogels as Synthetic Extracellular Matrix Materials." *Biomaterials*. vol. 20, pp. 45-53.

Schense, Jason C. and Jeffrey A. Hubbell. 1999. "Cross-Linking Exogenous Bifunctional Peptides into Fibrin Gels with Factor XIIIa." *Bioconjugate Chem*. vol. 10, No. 1, pp. 75-81.

Varma, H. K., Y. Yokogawa, F. F. Espinosa, Y. Kawamoto, K. Nishizawa, F. Nagata, and T. Kameyama. 1999. "In-Vitro Calcium Phosphate Growth over Functionalized Cotton Fibers." *Journal of Materials Science: Materials in Medicine*. vol. 10, pp. 395-400.

Vernon, Robert B. and E. Helene Sage. 1999. "A Novel, Quantitative Model for Study of Endothelial Cell Migration and Sprout Formation Within Three-Dimensional Collagen Matrices." *Microvascular Research*. vol. 57, pp. 188-133.

Wei, M., A. J. Ruys, M. V. Swain, S. H. Kim, B. K. Milthorpe, and C. C. Sorrell. 1999. "Interfacial Bond Strength of Electrophoretically Deposited Hydroxyapatite Coatings on Metals." *Journal of Materials Science: Materials in Medicine*. vol. 10, pp. 401-409.

Yagi, Nobuhiro, Yoshikatsu Ogawa, Masato Kodaka, Tomoko Okada, Takenori Tomohiro, Takeo Konakahara, and Hiroaki Okuno. 1999. "A Surface-Modified Functional Liposome Capable of Binding to Cell Membranes." *Chem. Commun*. pp. 1687-1688.

Yu, Ying-Ching, Vikram Roontga, Vladimir A. Daragan, Kevin H. Mayo, Matthew Tirrell, and Gregg B. Fields. 1999. "Structure and Dynamics of Peptide—Amphiphiles Incorporating Triple-Helical Proteinlike Molecular Architecture." *Biochemistry*. vol. 38, No. 5, pp. 1659-1668.

Huq, N. Laila, Keith J. Cross, and Eric C. Reynolds. Feb. 4, 2000. "Molecular Modelling of a Multiphosphorylated Sequence Motif Bound to Hydroxyapatite Surfaces." *Journal of Molecular Modeling*. vol. 6, pp. 35-47.

Martinez, J. S., G. P. Zhang, P. D. Holt, H.-T. Jung, C. J. Carrano, M. G. Haygood, and Alison Butler. Feb. 18, 2000. "Self-Assembling Amphiphilic Siderophores from Marine Bacteria." *Science*. vol. 287, No. 5456, pp. 1245-1247.

Verrecchio, Angela, Markus W. Germania, Barbara P. Schick, Brian Kung, Thomas Twardowski, and James D. San Antonio. Mar. 17, 2000. "Design of Peptides with High Affinities for Heparin and Endothelial Cell Proteoglycans." *The Journal of Biological Chemistry*. vol. 275, No. 11, pp. 7701-7707.

Cao, H., J. Y. Xu, E. W. Seelig, and R. P. H. Chang. May 22, 2000. "Microlaser Made of Disordered Media." *Applied Physics Letters*. vol. 76, No. 21, pp. 2997-2999.

Marler, Jennifer J., Amrita Guha, Jonathan Rowley, Rahul Koka, David Mooney, Joseph Upton, and Joseph Vacanti. May 2000. "Soft- Tissue Augmentation with Injectable Alginate and Syngeneic Fibroblasts." *Plastic and Reconstructive Surgery*. vol. 105, No. 6, pp. 2049-2058.

Holmes, Todd C., Sonsoles de Lacalle, Xing Su, Guosong Liu, Alexander Rich, and Shuguang Zhang. Jun. 6, 2000. "Extensive Neurite Outgrowth and Active Synapse Formation on Self-Assembling Peptide Scaffolds." *Proceedings of the National Academy of Sciences of the United States of America*. vol. 97, No. 12, pp. 6728-6733.

Whaley, Sandra R., D. S. English, Evelyn L. Hu, Paul F. Barbara, and Angela M. Belcher. Jun. 8, 2000. "Selection of Peptides with Semiconductor Binding Specificity for Directed Nanocrystal Assembly." *Nature*. vol. 405, pp. 665-668.

Sun, Xiu-xia and Chi-chen Wang. Jul. 28, 2000. "The N-Terminal Sequence (Residues 1-65) Is Essential for Dimerization, Activities, and Peptide Binding of *Escherichia coli* DsbC." *The Journal of Biological Chemistry*. vol. 275, No. 30, pp. 22743-22749.

Hsu, Wei-Cherng, Mark H. Spilker, Ioannis V. Yannas, and Peter A. D. Rubin. Aug. 2000. "Inhibition of Conjunctival Scarring and Contraction by a Porous Collagen-Glycosaminoglycan Implant." *Investigative Ophthalmology & Visual Science*. vol. 41, No. 9, pp. 2404-2411.

Schlessinger, Joseph, Alexander N. Plotnikov, Omar A. Ibrahimi, Anna V. Eliseenkova, Brian K. Yeh, Avner Yayon, Robert J. Linhardt, and Moosa Mohammadi Sep. 2000. "Crystal Structure of a Ternary FGF-FGFR-Heparin Complex Reveals a Dual Role for Heparin in FGFR Binding and Dimerization." *Molecular Cell*. vol. 6, pp. 743-750.

Sun, Y., J. B. Ketterson, and G. K. L. Wong. Oct. 9, 2000. "Excitonic Gain and Stimulated Ultraviolet Emission in Nanocrystalline Zinc-Oxide Powder." *Applied Physics Letters*. vol. 77, No. 15, pp. 2322-2324.

Schuldiner, Maya, Ofra Yanuka, Joseph Itskovitz-Eldor, Douglas A. Melton, and Nissim Benvenisty. Oct. 10, 2000. "Effects of Eight Growth Factors on the Differentiation of Cells Derived from Human Embryonic Stem Cells." *Proceedings of the National Academy of Sciences of the United States of America*. vol. 97, No. 21, pp. 11307-11312.

Altman, Michael, Peter Lee, Alexander Rich, and Shuguang Zhang. 2000. "Conformational Behavior of Ionic Self-Complementary Peptides." *Protein Science*. vol. 9, pp. 1095-1105.

Archer, Eric A., Noah T. Goldberg, Vincent Lynch, and Michael J. Krische. 2000. "Nanostructured Polymer Duplexes via the Covalent Casting of 1-Dimensional H-Bonding Motifs: A New Strategy for the Self-Assembly of Macromolecular Precursors." *Journal of the American Chemical Society*. vol. 122, No. 20, pp. 5006-5007.

Ariga, Katsuhiko, Jun-ichi Kikuchi, Masanobu Naito, Emiko Koyama, and Norihiro Yamada. 2000. "Modulated Supramolecular Assemblies Composed of Tripeptide Derivatives: Formation of Micrometer-Scale Rods, Nanometer-Size Needles, and Regular Patterns with Molecular-Level Flatness from the Same Compound." *Langmuir*. vol. 16, No. 11, pp. 4929-4939.

Beniash, E., W. Traub, A. Veis, and S. Weiner. 2000. "A Transmission Electron Microscope Study Using Vitrified Ice Sections of Predentin: Structural Changes in the Dentin Collagenous Matrix Prior to Mineralization." *Journal of Structural Biology*. vol. 132, pp. 212-225.

Bigi, Adriana, Elisa Boanini, Silvia Panzavolta, and Norberto Roveri. 2000. "Biomimetic Growth of Hydroxyapatite on Gelatin Films Doped with Sodium Polyacrylate." *Biomacromolecules*. vol. 1, No. 4, pp. 752-756.

Bourel, Line, Olivier CaHon, Hélène Gras-Masse, and Oleg Melnyk. 2000. "The Deprotection of Lys(Mtt) Revisited." *Journal of Peptide Science*. vol. 6, pp. 264-270.

Caplan, Michael R., Peter N. Moore, Shuguang Zhang, Roger D. Kamm, and Douglas A. Lauffenburger. 2000. "Self-Assembly of a β-Sheet Protein Governed by Relief of Electrostatic Repulsion Relative to van der Waals Attraction." *Biomacromolecules*. vol. 1, No. 4, pp. 627-631.

Cardullo, F., M. Crego Calama, B. H. M. Snellink-Ruël, J.-L. Weidmann, A. Bielejewska, R. Fokkens, N. M. M. Nibbering, P. Timmerman, and D. N. Reinhoudt. 2000. "Covalent Capture of Dynamic Hydrogen-Bonded Assemblies." *Chem. Commun*. pp. 367-368.

Chamberlain, L. J., I. V. Yannas, H-P. Hsu, G. R. Strichartz, and M. Spector. 2000. "Near-Terminus Axonal Structure and Function Following Rat Sciatic Nerve Regeneration Through a Collagen-GAG Matrix in a Ten-Millimeter Gap." *Journal of Neuroscience Research*. vol. 60, pp. 666-677.

David, Sunil A., Satish K. Awasthi, and P. Balaram. 2000. "The Role of Polar and Facial Amphipathic Character in Determining Lipopolysaccharide-Binding Properties in Synthetic Cationic Peptides." *Journal of Endotoxin Research*. vol. 6, No. 3, pp. 249-256.

Dori, Yoav, Havazelet Bianco-Peled, Sushil K. Satija, Gregg B. Fields, James B. McCarthy, and Matthew Tirrell. 2000. "Ligand Accessibility as Means to Control Cell Response to Bioactive Bilayer Membranes." *Journal of Biomedical Materials Research*. vol. 50, pp. 75-81.

Forns, Pilar, Janette L. Lauer-Fields, Su Gao, and Gregg B. Fields. 2000. "Induction of Protein-Like Molecular Architecture by Monoalkyl Hydrocarbon Chains." *Biopolymers*. vol. 54, pp. 531-546.

Hisaeda, Yoshio, Eiji Ohshima, and Makiko Arimura. 2000. "Aggregation Behavior of Synthetic Peptide Lipids with Arginine in Aqueous Solution and Construction of a Vitamin $B_{12}$ Artifical Enzyme." *Colloids and Surfaces A: Physicochemical and Engineering Aspects*. vol. 169, pp. 143-153.

Kogiso, Masaki, Yuji Okada, Takeshi Hanada, Kiyoshi Yase, and Toshimi Shimizu 2000. "Self-Assembled Peptide Fibers from Valylvaline Bola-Amphiphiles by a Parallel β-Sheet Network." *Biochimica et Biophysica Acta*. vol. 1475, pp. 346-352.

Langer, Robert. 2000. "Biomaterials in Drug Delivery and Tissue Engineering: One Laboratory's Experience." *Accounts of Chemical Research*. vol. 33, No. 2, pp. 94-101.

Liu, X. D., M. Skold, T. Umino, Y. K. Zhu, D. J. Romberger, J. R. Spurzem, and S. I. Rennard. 2000. "Endothelial Cell-Mediated Type I Collagen Gel Contraction Is Regulated by Hemin." *J. Lab. Clin. Med*. vol. 136, No. 2, pp. 100-109.

Lu, Lichun, Susan J. Peter, Michelle D. Lyman, Hui-Lin Lai, Susan M. Leite, Janet A. Tamada, Shiro Uyama, Joseph P. Vacanti, Robert Langer, and Antonios G. Mikos. 2000. "In Vitro and in Vivo Degradation of Porous Poly(DL-Lactic-*co*-Glycolic Acid) Foams." *Biomaterials*. vol. 21, pp. 1837-1845.

Matsuura, T., R. Hosokawa, K. Okamoto, T. Kimoto, and Y. Akagawa. 2000. "Diverse Mechanisms of Osteoblast Spreading on Hydroxyapatite and Titanium." *Biomaterials*. vol. 21, pp. 1121-1127.

Mulloy, Barbara and Mark J. Forster. 2000. "Conformation and Dynamics of Heparin and Heparan Sulfate." *Glycobiology*. vol. 10, No. 11, pp. 1147-1156.

Ponticiello, Michael S., Robert M. Schinagl, Sudha Kadiyala, and Frank P. Barry. 2000. "Gelatin-Based Resorbable Sponge as a Carrier Matrix for Human Mesenchymal Stem Cells in Cartilage Regeneration Therapy." *Journal of Biomedical Materials Research*. vol. 52, pp. 246-255.

Powell, Sharon K., Jayashree Rao, Eva Roque, Motoyoshi Nomizu, Yuichiro Kuratomi, Yoshihiko Yamada, and Hynda K. Kleinman 2000. "Neural Cell Response to Multiple Novel Sites on Laminin-1." *Journal of Neuroscience Research*. vol. 61, pp. 302-312.

Rapaport, Hanna, Kristian Kjaer, Torben R. Jensen, Leslie Leiserowitz, and David A. Tirrell. 2000. "Two-Dimensional Order in β-Sheet Peptide Monolayers." *Journal of the American Chemical Society*. vol. 122, No. 50, pp. 12523-12529.

Sakiyama-Elbert, Shelly E. and Jeffrey A. Hubbell. 2000. "Controlled Release of Nerve Growth Factor from a Heparin-Containing Fibrin-Based Cell Ingrowth Matrix." *Journal of Controlled Release*. vol. 69, pp. 149-158.

Sakiyama-Elbert, Shelly E. and Jeffrey A. Hubbell. 2000. "Development of Fibrin Derivatives for Controlled Release of Heparin-Binding Growth Factors." *Journal of Controlled Release*. vol. 65, pp. 389-402.

Thareja, R. K. and A. Mitra. 2000. "Random Laser Action in ZnO." *Appl. Phys*. vol. B 71, pp. 181-184.

Tunggal, Patrick, Neil Smyth, Mats Paulsson, and Mark-Christoph Ott. 2000. "Laminins: Structure and Genetic Regulation." *Microscopy Research and Technique*. vol. 51, pp. 214-227.

do Serro, Ana Paula Valagão Amadeu, Anabela Catarino Fernandes, and Benilde de Jesus Vieira Saramago. 2000. "Calcium Phosphate Deposition on Titanium Surfaces in the Presence of Fibronectin." *Journal of Biomedical Materials Research*. vol. 49, pp. 345-352.

Yamada, Norihiro and Katsuhiko Ariga. 2000. "Formation of β-Sheet Assemblage with a View to Developing an Amyloid Model." *Synlett*. vol. 5, pp. 575-586.

Yang, Lin and Paschalis Alexandridis. 2000. "Physicochemical Aspects of Drug Delivery and Release from Polymer-Based Colloids." *Current Opinion in Colloid & Interface Science*. vol. 5, pp. 132-143.

Yu, Huanran, Hiroshi Narusawa, Kisae Itoh, Akihiro Oshi, Narutoshi Yoshino, Kazuo Ohbu, Toshiaki Shirakawa, Kazuhiro Fukada, Masatoshi Fujii, Tadashi Kato, and Tsutomu Seimiya. 2000. "Hydrophilicity of Polar and Apolar Domains of Amphiphiles." *Journal of Colloid and Interface Science*. vol. 229, pp. 375-390.

Zhu, G., M. F. Mehler, P. C. Mabie, and J. A. Kessler. 2000. "Developmental Changes in Neural Progenitor Cell Lineage Commitment Do Not Depend on Epidermal Growth Factor Receptor Signaling " *Journal of Neuroscience Research*. vol. 59, pp. 312-320.

Jin, Young-Gu and K. J. Chang. Feb. 26, 2001. "Mechanism for the Enhanced Diffusion of Charged Oxygen Ions in $SiO_2$." *Physical Review Letters*. vol. 86, No. 9, pp. 1793-1796.

Orlic, Donald, Jan Kajstura, Stefano Chimenti, Igor Jakonuk, Stacie M. Anderson, Baosheng Li, James Picket, Ronald McKay, Bernardo Nadal-Ginard, David M. Bodine, Annarosa Leri, and Piero Anversa. Apr. 5, 2001. "Bone Marrow Cells Regenerate Infarcted Myocardium." *Nature*. vol. 410, pp. 701-705.

Vailhé, Bruno, Daniel Vittet, and Jean-Jacques Feige. Apr. 2001. "In Vitro Models of Vasculogenesis and Angiogenesis." *Laboratory Investigation*. vol. 81, No. 4, pp. 439-452.

Merkler, Doron, Gerlinde A. S. Metz, Olivier Raineteau, Volker Dietz, Martin E. Schwab, and Karim Fouad. May 15, 2001. "Locomotor Recovery in Spinal Cord-Injured Rats Treated with an Antibody Neutralizing the Myelin-Associated Neurite Growth Inhibitor Nogo-A." *The Journal of Neuroscience*. vol. 21, No. 10, pp. 3665-3673.

Davis, N. G., J. Teisen, C. Schuh, and D. C. Dunand. May 2001. "Solid-State Foaming of Titanium by Superplastic Expansion of Argon-Filled Pores." *J. Mater. Res*. vol. 16, No. 5, pp. 1508-1519.

Rabchevsky, Alexander G. and George M. Smith. May 2001. "Therapeutic Interventions Following Mammalian Spinal Cord Injury." *Arch. Neurol*. vol. 58, pp. 721-726.

Huang, Michael H., Samuel Mao, Henning Feick, Haoquan Yan, Yiying Wu, Hannes Kind, Eicke Weber, Richard Russo, and Peidong Yang. Jun. 8, 2001. "Room-Temperature Ultraviolet Nanowire Nanolasers." *Science*. vol. 292, pp. 1897-1899.

Lee, Kuen Yong and David J. Mooney. Jul. 2001. "Hydrogels for Tissue Engineering." *Chemical Reviews*. vol. 101, No. 7, pp. 1869-1879.

Aggeli, A., I. A. Nyrkova, M. Bell, R. Harding, L. Carrick, T. C. B. McLeish, A. N. Semenov, and N. Boden. Oct. 9, 2001. "Hierarchical Self-Assembly of Chiral Rod-Like Molecules as a Model for Peptide β-Sheet Tapes, Ribbons, Fibrils, and Fibers." *Proceedings of the National Academy of Sciences of the United States of America*. vol. 98, No. 21, pp. 11857-11862.

Hartgerink, Jeffrey D., Elia Beniash, and Samuel I. Stupp. Nov. 23, 2001. "Self-Assembly and Mineralization of Peptide-Amphiphile Nanofibers." *Science*. vol. 294, pp. 1684-1688.

Richardson, Thomas P., Martin C. Peters, Alessandra B. Ennett, and David J. Mooney. Nov. 2001. "Polymeric System for Dual Growth Factor Delivery." *Nature Biotechnology*. vol. 19, pp. 1029-1034.

Matsui, Hiroshi and Robert MacCuspie. Dec. 2001. "Metalloporphyrin Nanotube Fabrication Using Peptide Nanotubes as Templates." *Nano Letters*. vol. 1, No. 12, pp. 671-675.

Mathew, Mathai and Shozo Takagi. Nov.-Dec. 2001. "Structures of Biological Minerals in Dental Research." *Journal of Research of the National Institute of Standards and Technology*. vol. 106, No. 6, pp. 1035-1044.

Woo, Byung Ho, Betsy F. Fink, Richard Page, Jay A. Schrier, Yeong Woo Jo, Ge Jiang, Michelle DeLuca, Henry C. Vasconez, and Patrick P. DeLuca. Dec. 2001. "Enhancement of Bone Growth by Sustained Delivery of Recombinant Human Bone Morphogenetic Protein-2 in a Polymeric Matrix." *Pharmaceutical Research*. vol. 18, No. 12, pp. 1747-1753.

Barrère, F., P. Layrolle, C. A. Van Blitterswijk, and K. de Groot. 2001. "Biomimetic Coatings on Titanium: A Crystal Growth Study of Octacalcium Phosphate." *Journal of Materials Science: Materials in Medicine*. vol. 12, pp. 529-534.

Bianco-Peled, Havazelet, Yoav Dori, James Schneider, Li-Piin Sung, Sushil Satija, and Matthew Tirrell. 2001. "Structural Study of Langmuir Monolayers Containing Lipidated Poly(ethylene glycol) and Peptides." *Langmuir*. vol. 17, No. 22, pp. 6931-6937.

Bonnet, Dominique, Kader Thiam, Estelle Loing, Oleg Melnyk, and Helene Gras-Masse. 2001. Synthesis by Chemoselective Ligation and Biological Evaluation of Novel Cell-Permeable PKC-ζ Pseudosubstrate Lipopeptides. *J. Med. Chem*. vol. 44, No. 3, pp. 468-471.

Cavalli, M., G. Gnappi, A. Montenero, D. Bersani, P. P. Lottici, S. Kaciulis, G. Mattogno, and M. Fini. 2001. "Hydroxy- and Fluorapatite Films on Ti Alloy Substrates: Sol-gel Preparation and Characterization." *Journal of Materials Science*. vol. 36, pp. 3253-3260.

Chang, John C., Gregory J. Brewer, and Bruce C. Wheeler. 2001. "Modulation of Neural Network Activity by Patterning." *Biosensors & Bioelectronics*. vol. 16, pp. 527-533.

Chang, Sophia C. N., Jon A. Rowley, Geoffrey Tobias, Nicholas G. Genes, Amit K. Roy, David J. Mooney, Charles A. Vacanti, and Lawrence J. Bonassar. 2001. "Injection Molding of Chondrocyte/Alginate Constructs in the Shape of Facial Implants." *Journal of Biomedical Materials Research*. vol. 55, pp. 503-511.

Doi, Tomokiyo, Takatoshi Kinoshita, Hiroki Kamiya, Shintaro Washizu, Yoshiharu Tsujita, and Hiraoki Yoshimizu. 2001. "Aggregation of Polypeptide-Based Amphiphiles in Water." *Polymer Journal*. vol. 33, No. 2, pp. 160-164.

Gore, Tushar, Yoav Dori, Yeshayahu Talmon, Matthew Tirrell, and Havazelet Bianco-Peled. 2001. "Self-Assembly of Model Collagen Peptide Amphiphiles." *Langmuir*. vol. 17, No. 17, pp. 5352-5360.

Grothe, Claudia and Guido Nikkhah 2001. "The role of Basic Fibroblast Growth Factor in Peripheral Nerve Regeneration." *Anat. Embryol*. vol. 204, pp. 171-177.

Hoess, Ronald H. 2001. "Protein Design and Phage Display." *Chemical Reviews*. vol. 101, No. 10, pp. 3205-3218.

Huang, Eric J. and Louis F. Reichardt. 2001. "Neurotrophins: Roles in Neuronal Development and Function." *Annual Review of Neuroscience*. vol. 24, pp. 677-736.

Irvine, Darrell J. and Anne M. Mayes. 2001. "Nanoscale Clustering of RGD Peptides at Surfaces Using Comb Polymers. 1. Synthesis and Characterization of Comb Thin Films." *Biomacromolecules*. vol. 2, No. 1, pp. 85-94.

Kam, L., W. Shain, J. N. Turner, and R. Bizios. 2001. "Axonal Outgrowth of Hippocampal Neurons on Micro-Scale Networks of Polylysine-Conjugated Laminin." *Biomaterials*. vol. 22, pp. 1049-1054.

Kikuchi, Masanori, Soichiro Itoh, Shizuko Ichinose, Kenichi Shinomiya, and Junzo Tanaka 2001. "Self-Organization Mechanism in a Bone-Like Hydroxyapatite/Collagen Nancomposite Synthesized in Vitro and Its Biological Reaction in Vivo." *Biomaterials*. vol. 22, pp. 1705-1711.

Liu, Yuelian, Pierre Layrolle, Joost de Bruijn, Clemens van Blitterswijk, and Klaas de Groot. 2001. "Biomimetic Coprecipitation of Calcium Phosphate and Bovine Serum Albumin on Titanium Alloy." *Journal of Biomedical Materials Research*. vol. 57, pp. 327-335.

Look, D. C. 2001. "Recent Advances in ZnO Materials and Devices." *Materials Science and Engineering*. vol. B80, pp. 383-387.

Luo, Yi and Glenn D. Prestwich. 2001. "Novel Biomaterials for Drug Delivery." Expert Opin. Ther. Patents. vol. 11, No. 9, pp. 1395-1410.

Marchi-Artzner, Valerie, Barbara Lorz, Ulrike Hellerer, Martin Kantlehner, Horst Kessler, and Erich Sackmann 2001. "Selective Adhesion of Endothelial Cells to Artificial Membranes with a Synthetic RGD-Lipopeptide." *Chem. Eur. J*. vol. 7, No. 5, pp. 1095-1101.

Matsui, Hiroshi, and Gary E. Douberly, Jr. 2001. "Organization of Peptide Nanotubes into Macroscopic Bundles." *Langmuir*. vol. 17, No. 25, pp. 7918-7922.

Matsui, Hiroshi, Precila Porrata, and Gary E. Douberly, Jr. 2001. "Protein Tubule Immobilization on Self-Assembled Monolayers on Au Substrates." *Nano Letters*. vol. 1, No. 9, pp. 461-464.

Neet, K. E. and R. B. Campenot. 2001. "Receptor Binding, Internalization, and Retrograde Transport of Neurotrophic Factors." *CMLS, Cell Mol. Life Sci*. vol. 58, pp. 1021-1035.

Otsuka, Hidenori, Yukio Nagasaki, and Kazunori Kataoka. 2001. "Self-Assembly of Poly(ethylene glycol)—based Block Copolymers for Biomedical Applications." *Current Opinion in Colloid & Interface Science*. vol. 6, pp. 3-10.

Shimizu, Toshimi, Rika Iwaura, Mitsutoshi Masuda, Takeshi Hanada, and Kiyoshi Yase. 2001. "Internucleobase-Interaction-Directed Self-Assembly of Nanofibers from Homo- and Heteroditopic 1,ω-Nucleobase Bolaamphiphiles." *Journal of the American Chemical Society*. vol. 123, No. 25, pp. 5947-5955, S1-S16.

Socrates, George. 2001. *Infrared and Raman Characteristic Group Frequencies: Tables and Charts*. Third Edition. Chichester, England: John Wiley & Sons Ltd.

Spanos, Nikos and Petros G. Koutsoukos. 2001. "Model Studies of the Effect of Orthophospho-L-Serine on Biological Mineralization." *Langmuir*. vol. 17, No. 3, pp. 866-872.

Takadama, Hiroaki, Hyun-Min Kim, Tadashi Kokubo, and Takashi Nakamura. 2001. "TEM-EDX Study of Mechanism of Bonelike Apatite Formation on Bioactive Titanium Metal in Simulated Body Fluid." *Journal of Biomedical Materials Research*. vol. 57, pp. 441-448.

Tanihara, Masao, Yasuo Suzuki, Eriko Yamamoto, Atsushi Noguchi, and Yutaka Mizushima. 2001. "Sustained Release of Basic Fibroblast Growth Factor and Angiogenesis in a Novel Covalently Crosslinked Gel of Heparin and Alginate." *Journal of Biomedical Materials Research*. vol. 56, pp. 216-221.

Torchilin, Vladimir P. 2001. "Structure and Design of Polymeric Surfactant-Based Drug Delivery Systems." *Journal of Controlled Release*. vol. 73, pp. 137-172.

Yeung, C. K., L. Lauer, A. Offenhausser, and W. Knoll. 2001. "Modulation of the Growth and Guidance of Rat Brain Stem Neurons Using Patterned Extracellular Matrix Proteins." *Neuroscience Letters*. vol. 301, pp. 147-150.

Zubarev, Eugene R., Martin U. Pralle, Eli D. Sone, and Samuel I. Stupp. 2001. "Self-Assembly of Dendron Rodcoil Molecules into Nanoribbons." *Journal of the American Chemical Society*. vol. 123, No. 17, pp. 4105-4106.

Hirschi, Karen K., Lihua Lai, Narasimhaswamy S. Belaguli, David A. Dean, Robert J. Schwartz, and Warren E. Zimmer Feb. 22, 2002. "Transforming Growth Factor-β Induction of Smooth Muscle Cell Phenotype Requires Transcriptional and Post-transcriptional Control of Serum Response Factor." *The Journal of Biological Chemistry*. vol. 277, No. 8, pp. 6287-6295.

Xu, Weiming, Lizhi Liu, and Ian G. Charles. Feb. 2002. "Microencapsulated iNOS-expressing Cells Cause Tumor Suppression in Mice." *The FASEB Journal*. vol. 16, pp. 213-215.

Zubarev, Eugene R., Martin U. Pralle, Eli D. Sone, and Samuel I. Shipp. Feb. 2002. "Scaffolding of Polymers by Supramolecular Nanoribbons." *Advanced Materials*. vol. 14, No. 3, pp. 198-203.

Slocik, Joseph M., Joshua T. Moore, and David W. Wright. Mar. 2002. Monoclonal Antibody Recognition of Histidine-Rich Peptide Encapsulated Nanoclusters. *Nano Letters*. vol. 2, No. 3, pp. 169-173.

Teng, Yang D., Erin B. Lavik, Xianlu Qu, Kook I. Park, Jitka Ourednik, David Zurakowski, Robert Langer, and Evan Y. Snyder. Mar. 5, 2002. "Functional Recovery Following Traumatic Spinal Cord Injury Mediated by a Unique Polymer Scaffold Seeded with Neural Stem Cells." *Proceedings of the National Academy of Sciences of the United States of America*. vol. 99, No. 5, pp. 3024-3029.

Bradbury, Elizabeth J., Lawrence D. F. Moon, Reena J. Popat, Von R. King, Gavin S. Bennett, Preena N. Patel, James W. Fawcett, and Stephen B. McMahon. Apr. 11, 2002. "Chondroitinase ABC Promotes Functional Recovery After Spinal Cord Injury." *Nature*. vol. 416, pp. 636-640.

Hartgerink, Jeffrey D., Elia Beniash, and Samuel I. Stupp. Apr. 16, 2002. "Supramolecular Chemistry and Self-Assembly Special Feature: Peptide-Amphiphile Nanofibers: A Versatile Scaffold for the Preparation of Self-Assembling Materials." *Proceedings of the National Academy of Sciences of the United States of America*. vol. 99, No. 8, pp. 5133-5138.

Vauthey, Sylvain, Steve Santoso, Haiyan Gong, Nicki Watson, and Shuguang Zhang. Apr. 16, 2002. "Molecular Self-Assembly of Surfactant-like Peptides to Form Nanotubes and Nanovesicles." *Proceedings of the National Academy of Sciences of the United States of America*. vol. 99, No. 8, pp. 5355-5360.

Nowak, Andrew P., Victor Breedveld, Lisa Pakstis, Bulent Ozbas, David J. Pine, Darrin Pochan, and Timothy J. Deming. May 23, 2002. "Rapidly Recovering Hydrogel Scaffolds from Self-Assembling Diblock Copolypeptide Amphiphiles." *Nature*. vol. 417, pp. 424-428.

GrandPré, Tadzia, Shuxin Li, and Stephen M. Strittmatter. May 30, 2002. "Nogo-66 Receptor Antagonist Peptide Promotes Axonal Regeneration." *Nature*. vol. 417, pp. 547-551.

Storch, Alexander and Johannes Schwarz. May 2002. "Neural Stem Cells and Neurodegeneration." *Current Opinion in Investigational Drugs*. vol. 3, No. 5, pp. 774-781.

Lendlein, Andreas and Robert Langer. May 31, 2002. "Biodegradable, Elastic Shape-Memory Polymers for Potential Biomedical Applications." *Science*. vol. 296, pp. 1673-1676.

Qiu, Jin, Dongming Cai, Haining Dai, Marietta McAttee, Paul N. Hoffman, Barbara S. Bregman, and Marie T. Filbin. Jun. 13, 2002. "Spinal Axon Regeneration Induced by Elevation of Cyclic AMP." *Neuron*. vol. 34, pp. 895-903.

Catledge, Shane A., Marc D. Fries, Yogesh K. Vohra, William R Lacefield, Jack E. Lemons, Shanna Woodard, and Ramakrishna Venugopalan. Jun.-Aug. 2002. "Nanostructured Ceramics for Biomedical Implants." *Journal of Nanoscience and Nanotechnology*. vol. 2, No. 3/4, pp. 293-312.

Alsberg, Eben, Kenneth W. Anderson, Amru Albeiruti, Jon A. Rowley, and David J. Mooney. Sep. 17, 2002. "Engineering Growing Tissues." *Proceedings of the National Academy of Sciences of the United States of America*. vol. 99, No. 19, pp. 12025-12030.

Kay, Sarina, Anil Thapa, Karen M. Haberstroh, and Thomas J. Webster. Oct. 2002. "Nanostructured Polymer/Nanophase Ceramic Composites Enhance Osteoblast and Chondrocyte Adhesion." *Tissue Engineering*. vol. 8, No. 5, pp. 753-761.

Blight, Andrew R. Nov. 2002. "Miracles and Molecules—Progress in Spinal Cord Repair." Nature Neuroscience Supplement. vol. 5, pp. 1051-1054.

Silva, G. A., C. Czeisler, K. L. Niece, E. Beniash, J. D. Hartgerink, J. A. Kessler, and S. I. Stupp. Nov. 2-7, 2002. "Development of Neural Progenitor Cells Encapsulated in a Peptide Amphiphile Substrate That Is Induced to Self-Assemble Under Physiological Conditions." *Biosis*. Society for Neuroscience Abstract Viewer and Itinerary Planner—2002. Abstract No. 825.4. 32nd Annual Meeting of the Society for Neuroscience; Orlando, Florida.

Chang, Hua, Chester W. Brown, and Martin M. Matzuk. Dec. 2002. "Genetic Analysis of the Mammalian Transforming Growth Factor-β Superfamily." *Endocrine Reviews*. vol. 23, No. 6, pp. 787-823.

Avrahami, Dorit and Yechiel Shai. 2002. "Conjugation of a Magainin Analogue with Lipophilic Acids Controls Hydrophobicity, Solution Assembly, and Cell Selectivity." *Biochemistry*. vol. 41, No. 7, pp. 2254-2263.

Busqué, Félix, Stephanie A. Hopkins, and Joseph P. Konopelski. 2002. "Progress Toward a Peptidomimetic of Laminin-Derived Pentapeptide YIGSR: Synthesis of the Unique Tricyclic Core Structure." *J. Org. Chem*. vol. 67, No. 17, pp. 6097-6103.

Canaple, Laurence, Annemie Rehor, and David Hunkeler. 2002. "Improving Cell Encapsulation Through Size Control." *J. Biomater. Sci. Polymer Edn*. vol. 13, No. 7, pp. 783-796.

Caplan, Michael R., Elissa M. Schwartzfarb, Shuguang Zhang, Roger D. Kamm, and Douglas A. Lauffenburger. 2002. "Control of Self-Assembling Oligopeptide Matrix Formation Through Systematic Variation of Amino Acid Sequence." *Biomaterials*. vol. 23, pp. 219-227.

Chen, Zhi Jiang, Yvonne Ughrin, and Joel M. Levine. 2002. "Inhibition of Axon Growth by Oligodendrocyte Precursor Cells." *Molecular and Cellular Neuroscience*. vol. 20, pp. 125-139.

Cornish, Toby, Darren W. Branch, Bruce C. Wheeler, and James T. Campanelli. 2002. "Microcontact Printing: A Versatile Technique for the Study of Synaptogenic Molecules." *Molecular and Cellular Neuroscience*. vol. 20, pp. 140-153.

Costa, Silvia, Thierry Planchenault, Cecile Charriere-Bertrand, Yann Mouchel, Christiane Fages, Sharon Juliano, Thierry Lefrançois, Georgia Barlovatz-Meimon, and Marcienne Tardy. 2002. "Astroglial Permissivity for Neuritic Outgrowth in Neuron-Astrocyte Cocultures Depends on Regulation of Laminin Bioavailability." *GLIA*. vol. 37, pp. 105-113.

Gariépy, Jean, Sandrine Rémy, Xiuguo Zhang, James R. Ballinger, Eleonora Bolewska-Pedyczak, Michael Rauth, and Stuart K. Bisland. 2002. "A Simple Two-Step Approach for Introducing a Protected Diaminedithiol Chelator During Solid-Phase Assembly of Peptides." *Bioconjugate Chem*. vol. 13, No. 3, pp. 679-684.

Glättli, Alice, Xavier Daum, Dieter Seebach, and Wilfred F. van Gunsteren. 2002. "Can One Derive the Confrontational Preference of a β-Peptide from Its CD Spectrum?" *Journal of the American Chemical Society*. vol. 124, No. 44, pp. 12972-12978.

Gutwein, Luke G. and Thomas J. Webster. 2002. "Osteoblast and Chondrocyte Proliferation in the Presence of Alumina and Titania Nanoparticles." *Journal of Nanoparticle Research*. vol. 4, pp. 231-238.

Huang, Ning-Ping, Gabor Csucs, Kazunori Emoto, Yukio Nagasaki, Kazunori Kataoka, Marcus Textor, and Nicholas D. Spencer. 2002. "Covalent Attachment of Novel Poly(ethylene glycol)—Poly(DL-lactic acid) Copolymeric Micelles to $TiO_2$ Surfaces." *Langmuir*. vol. 18, No. 1, pp. 252-258.

Issac, Roy and Jean Chmielewski. 2002. "Approaching Exponential Growth with a Self-Replicating Peptide." *Journal of the American Chemical Society*. vol. 124, No. 24, pp. 6808-6809.

Joshi, Mital and Michael G. Fehlings. 2002. "Development and Characterization of a Novel, Graded Model of Clip Compressive Spinal Cord Injury in the Mouse: Part 1. Clip Design, Behavioral Outcomes, and Histopathology." *Journal of Neurotrauma*. vol. 19, No. 2, pp. 175-190.

Joshi, Mital and Michael G. Fehlings. 2002. "Development and Characterization of a Novel, Graded Model of Clip Compressive Spinal Cord Injury in the Mouse: Part 2. Quantitative Neuroanatomical Assessment and Analysis of the Relationships Between Axonal Tracts, Residual Tissue, and Locomotor Recovery." *Journal of Neurotrauma*. vol. 19, No. 2, pp. 191-203.

Kruger, Ryan G., Patrick Dostal, and Dewey G. McCafferty. 2002. "An Economical and Preparative Orthogonal Solid Phase Synthesis of Fluorescein and Rhodamine Derivatized Peptides: FRET Substrates for the *Staphylococcus aureus* Sortase SrtA Transpeptidase Reaction." *Chem. Commun*. pp. 2092-2093.

Lauer, L., A. Vogt, C. K. Yeung, W. Knoll, and A. Offenhäusser. 2002. "Electrophysiological Recordings of Patterned Rat Brain Stem Slice Neurons." *Biomaterials*. vol. 23, pp. 3123-3130.

Lavik, Erin, Yang D. Teng, Evan Snyder, and Robert Langer. 2002. "Speeding Neural Stem Cells on Scaffolds of PGA, PLA, and Their Copolymers." *Methods in Molecular Biology: Neural Stem Cells: Methods and Protocols*. vol. 198, pp. 89-97.

Marini, Davide M., Wonmuk Hwang, Douglas A. Lauffenburger, Shuguang Zhang, and Roger D. Kamm. 2002. "Left-Handed Helical Ribbon Intermediates in the Self-Assembly of a β-Sheet Peptide." *Nano Letters*. vol. 2, No. 4, pp. 295-299.

Ohsaki, Mio, Tatsuya Okuda, Akihiro Wada, Toshiya Hirayama, Takuro Niidome, and Haruhiko Aoyagi. 2002. "In Vitro Gene Transfection Using Dendritic Poly(L-lysine)." *Bioconjugate Chem*. vol. 13, No. 3, pp. 510-517.

Okano, Hideyuki. 2002. "Stem Cell Biology of the Central Nervous System." *Journal of Neuroscience Research*. vol. 69, pp. 698-707.

Parmar, Malin, Charlotta Skogh, Anders Björklund, and Kenneth Campbell. 2002. "Regional Specification of Neurosphere Cultures Derived from Subregions of the Embryonic Telencephalon." *Molecular and Cellular Neuroscience*. vol. 21, pp. 645-656.

Porter, A. E., L. W. Hobbs, V. Benezra Rosen, and M. Spector. 2002. "The Ultrastructure of the Plasma-Sprayed Hydroxyapatite-bone Interface Predisposing to Bone Bonding." *Biomaterials*. vol. 23, pp. 725-733.

Rodger, Alison, Jascindra Rajendra, Rachel Marrington, Malin Ardhammar, Bengt Norden, Jonathan D. Hirst, Andrew T. B. Gilbert, Timothy R. Dafforn, David J. Halsall, Cheryl A. Woolhead, Colin Robinson, Teresa J. T. Pinheiro, Jurate Kazlauskaite, Mark Seymour, Niuvis Perez, and Michael J. Hannon. 2002. "Flow Oriented Linear Dichroism to Probe Protein Orientation in Membrane Environments." *Phys. Chem. Chem. Phys*. vol. 4, pp. 4051-4057.

Rowley, Jon A. and David J. Mooney. 2002. "Alginate Type and RGD Density Control Myoblast Phenotype." *Journal of Biomedical Materials Research*. vol. 60, pp. 217-223.

Santoso, Steve S., Sylvain Vauthey, and Shuguang Zhang. 2002. "Structures, Function and Applications of Amphiphilic Peptides." *Current Opinion in Colloid & Interface Science*. vol. 7, pp. 262-266.

Shih, Sheng-Ming, Wei-Fang Su, Yuh-Jivan Lin, Cen-Shawn Wu, and Chii-Dong Chen. 2002. "Two-Dimensional Arrays of Self-Assembled Gold and Sulfur-Containing Fullerene Nanoparticles." *Langmuir*. vol. 18, No. 8, pp. 3332-3335.

Thiébaud, Pierre, Lars Lauer, Wolfgang Knoll, and Andreas Offenhäuser. 2002. "PDMS Device for Patterned Application of Microfluids to Neuronal Cells Arranged by Microcontact Printing." *Biosensors & Bioelectronics*. vol. 17, pp. 87-93.

Tryoen-Tóth, Petra, Dominique Vautier, Youssef Haikel, Jean-Claude Voegel, Pierre Schaaf, Johanna Chluba, and Joëlle Ogier. 2002. "Viability, Adhesion, and Bone Phenotype of Osteoblast-like Cells on Polyelectrolyte Multilayer Films." *Journal of Biomedical Materials Research*. vol. 60, pp. 657-667.

Wong, Michael S., Jennifer N. Cha, Kyoung-Shin Choi, Timothy J. Deming, and Galen D. Stucky. 2002. "Assembly of Nanoparticles into Hollow Spheres Using Block Copolypeptides." *Nano Letters*. vol. 2, No. 6, pp. 583-587.

Yamada, Masanori, Yuichi Kadoya, Shingo Kasai, Kozue Kato, Mayumi Mochizuki, Norio Nishi, Nobuhisa Watanabe, Hynda K. Kleinman, Yoshihiko Yamada, and Motoyoshi Nomizu. 2002. "Ile-Lys-Val-Ala-Val (IKVAV)-Containing Laminin α1 Chain Peptides Form Amyloid-like Fibrils." *FEBS Letters*. vol. 530, pp. 48-52.

Young, Wise. 2002. "Spinal Cord Contusion Models." *Progress in Brain Research*. vol. 137, pp. 231-255.

Bruggeman, Holger, Sebastian Baumer, Wolfgang Florian Fricke, Arnim Wiezer, Heiko Liesegang, Iwona Decker, Christina Herzberg, Rosa Martinez-Arias, Rainer Merkl, Anke Benne, and Gerhard Gottschalk. Feb. 4, 2003. "The Genome Sequence of *Clostridium tetani*, the Causative Agent of Tetanus Disease." *PNAS*. vol. 100, No. 3, pp. 1316-1321.

McGregor, Clare-Louise, Lu Chen, Neil C. Pomroy, Peter Hwang, Sandy Go, Avijit Chakrabartty, and Gilbert G. Privé. Feb. 2003. "Lipopeptide Detergents Designed for the Structural Study of Membrane Proteins." *Nature Biotechnology*. vol. 21, pp. 171-176.

Lutolf, Matthias P., Franz E. Weber, Hugo G. Schmoekel, Jason C. Schense, Thomas Kohler, Ralph Müller, and Jeffrey A. Hubbell. May 2003. "Repair of Bone Defects Using Synthetic Mimetics of Collagenous Extracellular Matrices." *Nature Biotechnology*. vol. 21, pp. 513-518.

Shaw, Derek and Molly S. Shoichet. May 2003. "Toward Spinal Cord Injury Repair Strategies: Peptide Surface Modification of Expanded Poly(Tetrafluoroethylene) Fibers for Guided Neurite Outgrowth in Vitro." *The Journal of Craniofacial Surgery*. vol. 14, No. 3, pp. 308-316.

Silva, G. A., K. L. Kehl, K. L. Niece, and S. I. Stupp. May 4, 2003. "Nanoengineered Peptide Amphiphile Network for Photoreceptor Replacement in Degenerative Retinal Disorders." Investigative Ophthalmology & Visual Science. Abstract No. 492 from Annual Meeting of the Association for Research in Vision and Opthalmology.

Cheng, Hongwei, Wei Jiang, Frank M. Phillips, Rex C. Haydon, Ying Peng, Lan Zhou, Hue H. Luu, Naili An, Benjamin Breyer, Pantila Vanichakarn, Jan Paul Szatkowski, Jae Yoon Park, and Tong-Chuan He. Aug. 2003. "Osteogenic Activity of the Fourteen Types of Human Bone Morphogenetic Proteins (BMPS)." *The Journal of Bone & Joint Surgery*. vol. 85-A, No. 8, pp. 1544-1552, 141.

Leng, J., S. U. Egelhaaf, and M. E. Cates. Sep. 2003. "Kinetics of the Micelle-to-Vesicle Transition: Aqueous Lecithin-Bile Salt Mixtures." *Biophysical Journal*. vol. 85, No. 3, pp. 1624-1646.

Arinzeh, Treena Livingston, Susan J. Peter, Michael P. Archambault, Christian van den Bos, Steve Gordon, Karl Kraus, Alan Smith, and Sudha Kadiyala. Oct. 2003. "Allogeneic Mesenchymal Stem Cells Regenerate Bone in a Critical-Sized Canine Segmental Defect." *The Journal of Bone & Joint Surgery*. vol. 85-A, No. 10, pp. 1927-1935.

Zhang, Shuguang. Oct. 2003. "Fabrication of Novel Biomaterials Through Molecular Self-Assembly." *Nature Biotechnology*. vol. 21, No. 10, pp. 1171-1178.

Aggeli, Amalia, Mark Bell, Lisa M. Carrick, Colin W. G. Fishwick, Richard Harding, Peter J. Mawer, Sheena E. Radford, Andrew E. Strong, and Neville Boden. 2003. "pH as a Trigger of Peptide β-Sheet Self-Assembly and Reversible Switching Between Nematic and Isotropic Phases." *Journal of the American Chemical Society*. vol. 125, No. 32, pp. 9619-9628.

Alsina, Jordi and Fernando Albericio. 2003. "Solid-Phase Synthesis of C-Terminal Modified Peptides." *Biopolymers (Peptide Science)*. vol. 71, pp. 454-477.

Anthony, Shawn G. 2003. "Injectable Biomaterials for Bone Tissue Engineering."

Boontheekul, Tanyarut and David J. Mooney. 2003. "Protein-Based Signaling Systems in Tissue Engineering." *Current Opinion in Biotechnology*. vol. 14, pp. 559-565.

Brandenburg, Klaus, Frauke Wagner, Mareike Muller, Holger Heine, Jorg Andra, Michel H. J. Koch, Ulrich Zahringer, and Ulrich Seydel. 2003. "Physicochemical Characterization and Biological Activity of a Glycoglycerolipid from Mycoplasma fermentans." *Eur. J. Biochem*. vol. 270, pp. 3271-3279.

Czeisler, C., V. M. Tysseling-Mattiace, G. A. Silva, S. I. Shipp, and J. A. Kessler. 2003. "Behavoral Improvement and Increased Survival Rate after Treatment with a Self Assembling Gel in a Rat Model of Spinal Cord Injury." 2003 Abstract Viewer/Itinerary Planner. Program No. 245.22. Washington, DC: Society for Neuroscience. Printed Feb. 5, 2007. p. 1. http://sfn.scholarone.com/itin2003/main.html?new_page_id=126&abstract_id=1554 . . . .

Dupin, Elisabeth, and Nicole M. Le Douarin. 2003. "Development of Melanocyte Precursors from the Vertebrate Neural Crest" Oncogene. vol. 22, pp. 3016-3023.

Fauza, Dario O. 2003. "Tissue Engineering: Current State of Clinical Application." *Current Opinion in Pediatrics*. vol. 15, pp. 267-271.

Ganesh, S. and R. Jayakumar. 2003. "Structural Transitions Involved in a Novel Amyloid-Like β-Sheet Assemblage of Tripeptide Derivatives." *Biopolymers*. vol. 70, pp. 336-345.

Ganesh, S., S. Prakash, and R. Jayakumar. 2003. "Spectroscopic Investigation on Gel-Forming β-Sheet Assemblage of Peptide Derivatives." *Biopolymers*. vol. 70, pp. 346-354.

Gergely, C. S., P. Bar Yosef, R. Govrin-Lippman, F. Cuisinier, and H. Fiiredi-Milhofer. 2003. "The Deposition of Calcium Phosphates Within Polyelectrolyte Multilayer Films." *Key Engineering Materials*. vols. 240-242 (Bioceramics), pp. 287-290.

Goeden-Wood, Nichole L., Jay D. Keasling, and Susan J. Muller. 2003. "Self-Assembly of a Designed Protein Polymer into β-Sheet Fibrils and Responsive Gels." *Macromolecules*. vol. 36, No. 8, pp. 2932-2938.

Ishihara, Masayuki, Kiyohaya Obara, Toshiaki Ishizuka, Masanori Fujita, Masato Sato, Kazunori Masuoka, Yoshio Saito, Hirofumi Yura, Takemi Matsui, Hidemi Hattori, Makoto Kikuchi, and Akira Kurita. 2003. "Controlled Release of Fibroblast Growth Factors and Heparin from Photocrosslinked Chitosan Hydrogels and Subsequent Effect on in Vivo Vascularization." *Journal of Biomedical Materials Research*. vol. 64A, pp. 551-559.

Malkar, Navdeep B., Janette L. Lauer-Fields, Darius Juska, and Gregg B. Fields. 2003. "Characterization of Peptide-Amphiphiles Possessing Cellular Activation Sequences." *Biomacromolecules*. vol. 4, No. 3, pp. 518-528.

Niece, Krista L., Jeffrey D. Hartgerink, Jack J. J. M. Donners, and Samuel I. Stupp. 2003. "Self-Assembly Combining Two Bioactive Peptide-Amphiphile Molecules into Nanofibers by Electrostatic Attraction." *Journal of the American Chemical Society*. vol. 125, No. 24, pp. 7146-7147.

Pavlov, Georges, Stéphanie Finet, Karine Tatarenko, Evgueniya Komeeva, and Christine Ebel. 2003. "Conformation of Heparin Studied with Macromolecular Hydrodynamic Methods and X-ray Scattering." *Eur. Biophys. J*. vol. 32, pp. 437-449.

Schmidt, Christine E. and Jennie Baier Leach. 2003. "Neural Tissue Engineering: Strategies for Repair and Regeneration." *Annu. Rev. Biomed. Eng*. vol. 5, pp. 293-347.

Steward, Oswald, Binhai Zheng, and Marc Tessier-Lavigne. 2003. "False Resurrections: Distinguishing Regenerated from Spared Axons in the Injured Central Nervous System." *The Journal of Comparative Neurology*. vol. 459, pp. 1-8.

t' Hart, Bert A. and Sandra Amor. 2003. "The Use of Animal Models to Investigate the Pathogenesis of Neuroinflammatory Disorders of the Central Nervous System." Current Opinion in Neurology. vol. 16, pp. 375-383.

Wu, Sufan, Yoshihisa Suzuki, Yoko Ejiri, Toru Noda, Hongliang Bai, Masaaki Kitada, Kazuya Kataoka, Masayoshi Ohta, Hirotomi Chou, and Chizuka Ide. 2003. "Bone Marrow Stromal Cells Enhance Differentiation of Cocultured Neurosphere Cells and Promote Regeneration of Injured Spinal Cord." *Journal of Neuroscience Research*. vol. 72, pp. 343-351.

Yamada, Norihiro, Tsukasa Komatsu, Hirotsugu Yoshinaga, Kayo Yoshizawa, Susumu Edo, and Masashi Kunitake. 2003. "Self-Supporting Elastic Film without Covalent Linkages as a Hierarchically Integrated β-Sheet Assembly." *Angew. Chem. Int. Ed*. vol. 42, pp. 5496-5499.

Zhang, Yan, Hongwei Gu, Zhimou Yang, and Bing Xu. 2003. "Supramolecular Hydrogels Respond to Ligand-Receptor Interaction." *Journal of the American Chemical Society*. vol. 125, No. 45, pp. 13680-13681.

Hirano, Yoshiaki and David J. Mooney. Jan. 5, 2004. "Peptide and Protein Presenting Materials for Tissue Engineering." *Advanced Materials*. vol. 16, No. 1, pp. 17-25.

Silva, Gabriel A., Catherine Czeisler, Krista L. Niece, Elia Beniash, Daniel A. Harrington, John A. Kessler, and Samuel I. Shipp. Feb. 27, 2004. "Selective Differentiation of Neural Progenitor Cells by High-Epitope Density Nanofibers." *Science*. vol. 303, pp. 1352-1355.

Faulkner, Jill R., Julia E. Herrmann, Michael J. Woo, Keith E. Tansey, Ngan B. Doan, and Michael V. Sofroniew. Mar. 3, 2004. "Reactive Astrocytes Protect Tissue and Preserve Function after Spinal Cord Injury." *The Journal of Neuroscience*. vol. 24, No. 9, pp. 2143-2155.

Cao, Renhai, Anna Eriksson, Hajime Kubo, Kari Alitalo, Yihai Cao, Johan Thyberg. Mar. 19, 2004. "Comparative Evaluation of FGF-2-, VEGF-A-, and VEGF-C-Induced Angiogenesis, Lymphangiogenesis, Vascular Fenestrations, and Permeability." *Circulation Research*. vol. 94, pp. 664-670.

Anthony, Shawn G. Mar. 28-Apr. 1, 2004. "Self-Assembling Nanofiber Matrix for Bone Regeneration." *The 227th ACS National Meeting*. Anaheim, CA.

Donners, Jack J. J. M. Mar. 28-Apr. 1, 2004. "Growth Factor Binding Self-Assembling Nanofiber Networks for Tissue Regeneration." *The 227th ACS National Meeting*. Anaheim, CA.

Hui, Michael. May 24, 2004. "Heparin Binding Peptide Amphiphile and Transforming Growth Factor: A Novel Approach to Anti-Angiogenic Drug Delivery." The Second Annual Undergraduate Research Symposium. Retrieved from http://www.northwestern.edu/provost/students/research_symposium/program2004.pdf on Oct. 14, 2009. 45 pages.

Nikulina Elena, J. Lille Tidwell, Hai Ning Dai, Barbara S. Bregman, and Marie T. Filbin. Jun. 8, 2004. "The Phosphodiesterase Inhibitor Rolipram Delivered after a Spinal Cord Lesion Promotes Axonal Regeneration and Functional Recovery." *Proceedings of the National Academy of Sciences of the United States of America*. vol. 101, No. 23, pp. 8786-8790.

Pearse, Damien D., Francisco C. Pereira, Alexander E. Marcillo, Margaret L. Bates, Yerko A. Berrocal, Marie T. Filbin, and Mary Bartlett Bunge. Jun. 2004. "cAMP and Schwann Cells Promote Axonal Growth and Functional Recovery After Spinal Cord Injury." *Nature Medicine*. vol. 10, No. 6, pp. 610-616.

Lu, Paul, Hong Yang, Leonard L. Jones, Marie T. Filbin, and Mark H. Tuszynski. Jul. 14, 2004. "Combinatorial Therapy with Neurotrophins and cAMP Promotes Axonal Regeneration beyond Sites of Spinal Cord Injury." *The Journal of Neuroscience*. vol. 24, No. 28, pp. 6402-6409.

Lee, K. W., J. J. Yoon, J. H. Lee, S. Y. Kim, H. J. Jung, S. J. Kim, J. W. Joh, H. H. Lee, D. S. Lee, and S. K. Lee. 2004. "Sustained Release of Vascular Endothelial Growth Factor From Calcium-Induced Alginate Hydrogels Reinforced by Heparin and Chitosan." *Transplantation Proceedings*. vol. 36, pp. 2464-2465.

Mardilovich, Anastasia, and Efrosini Kokkoli. 2004. "Biomimetic Peptide—Amphiphiles for Functional Biomaterials: The Role of GRGDSP and PHSRN." Biomacromolecules. vol. 5, No. 3, pp. 950-957.

Matsumura, Sachiko, Shinobu Uemura, and Hisakazu Mihara. 2004. "Fabrication of Nanofibers with Uniform Morphology by Self-Assembly of Designed Peptides." *Chem. Eur. J.* vol. 10, pp. 2789-2794.

Ohmori, Hideya, Yasumitsu Sato, and Akiyoshi Namiki. 2004. "The Anticonvulsant Action of Propofol on Epileptiform Activity in Rat Hippocampal Slices." *Anesth. Analg.* vol. 99, pp. 1095-1101.

Shahraki, Ali and Trevor W. Stone. 2004. "Blockade of Presynaptic Adenosine A1 Receptor Responses by Nitric Oxide and Superoxide in Rat Hippocampus." *European Journal of Neuroscience.* vol. 20, pp. 719-728.

Sieminski, A. L., R. P. Hebbel, and K. J. Gooch. 2004. "The Relative Magnitudes of Endothelial Force Generation and Matrix Stiffness Modulate Capillary Morphogenesis in Vitro." *Experimental Cell Research.* vol. 297, pp. 574-584.

Sone, Eli D. and Samuel I. Stupp. 2004. "Semiconductor-Encapsulated Peptide-Amphiphile Nanofibers." *Journal of the American Chemical Society.* vol. 126, No. 40, pp. 12756-12757.

Smith, L. A. and P. X. Ma. 2004. "Nano-Fibrous Scaffolds for Tissue Engineering." *Colloids and Surfaces. B: Biointerfaces.* vol. 39, pp. 125-131.

Tsonchev, Stefan, George C. Schatz, and Mark A. Ratner. 2004. "Electrostatically-Directed Self-Assembly of Cylindrical Peptide Amphiphile Nanostructures." *J. Phys. Chem. B.* vol. 108, No. 26, pp. 8817-8822.

Tsonchev, Stefan, Alessandro Troisi, George C. Schatz, and Mark A. Ratner. 2004. "All-Atom Numerical Studies of Self-Assembly of Zwitterionic Peptide Amphiphiles." *J. Phys. Chem. B.* vol. 108, No. 39, pp. 15278-15284.

Tsonchev, Stefan, Alessandro Troisi, George C. Schatz, and Mark A. Ratner. 2004. "On the Structure and Stability of Self-Assembled Zwitterionic Peptide Amphiphiles: A Theoretical Study." *Nano Letters.* vol. 4, No. 3, pp. 427-431.

Vandermeulen, Guido W. M. and Harm-Anton Klok. 2004. "Peptide/Protein Hybrid Materials: Enhanced Control of Structure and Improved Performance through Conjugation of Biological and Synthetic Polymers." *Macromolecular Bioscience.* vol. 4, pp. 383-398.

Wang, Lin-Fa and Meng Yu. 2004. "Epitope Identification and Discovery Using Phage Display Libraries: Applications in Vaccine Development and Diagnostics." *Current Drug Targets.* vol. 5, No. 1, pp. 1-15.

Sayle, Roger. Printed Nov. 9, 2005. "Physiological Ionization and pKa Prediction." http://www.daylight.com/meetings/emug00/Sayle/pkapredict.html. pp. 1-13.

Arnold, Michael S., Mustafa O. Guler, Mark C. Hersam, and Samuel I. Stupp. 2005. "Encapsulation of Carbon Nanotubes by Self-Assembling Peptide Amphiphiles." *Langmuir.* vol. 21, No. 10, pp. 4705-4709.

Behanna, Heather A., Jack J. J. M. Donners, Alex C. Gordon, and Samuel I. Stupp. 2005. "Coassembly of Amphiphiles with Opposite Peptide Polarities into Nanofibers." *Journal of the American Chemical Society.* vol. 127, No. 4, pp. 1193-1200.

Beniash, Elia, Jeffery D. Hartgerink, Hannah Storrie, John C. Stendahl, and Samuel I. Stupp. 2005. "Self-Assembling Peptide Amphiphile Nanofiber Matrices for Cell Entrapment." *Acta Biomaterialia.* vol. 1, pp. 387-397.

Bitton, Ronit, Judith Schmidt, Markus Biesalski, Raymond Tu, Matthew Tirrell, and Havazelet Bianco-Peled. 2005. "Self-Assembly of Model DNA-Binding Peptide Amphiphiles." *Langmuir.* vol. 21, No. 25, pp. 11888-11895.

Bull, Steve R., Mustafa O. Guler, Rafael E. Bras, Thomas J. Meade, and Samuel I. Stupp. 2005. "Self-Assembled Peptide Amphiphile Nanofibers Conjugated to MRI Contrast Agents." *Nano Letters.* vol. 5, No. 1, pp. 1-4.

Bull, Steve R., Mustafa O. Guler, Rafael E. Bras, Palamadai N. Venkatasubramanian, Samuel I. Stupp, and Thomas J. Meade. 2005. "Magnetic Resonance Imaging of Self-Assembled Biomaterial Scaffolds." *Bioconjugate Chem.* vol. 16, No. 6, pp. 1343-1348.

de Loos, Maaike, Ben L. Feringa, and Jan H. van Esch. 2005. "Design and Application of Self-Assembled Low Molecular Weight Hydrogels." *Eur. J. Org. Chem.* pp. 3615-3631.

Guler, Mustafa O., Randal C. Claussen, and Samuel I. Stupp. 2005. "Encapsulation of Pyrene Within Self-Assembled Peptide Amphiphile Nanofibers." *Journal of Materials Chemistry.* vol. 15, pp. 4507-4512.

Guler, Mustafa O., Jonathan K. Pokorski, Daniel H. Appella, and Samuel I. Supp. 2005 "Enhanced Oligonucleotide Binding to Self-Assembled Nanofibers." *Bioconjugate Chem.* vol. 16, No. 3, pp. 501-503.

Guler, Mustafa O., Stephen Soukasene, James F. Hulvat, and Samuel I. Stupp. 2005. "Presentation and Recognition of Biotin on Nanofibers Formed by Branched Peptide Amphiphiles." *Nano Letters.* vol. 5, No. 2, pp. 249-252.

Jun, Ho-Wook, Virany Yuwono, Sergey E. Paramonov, and Jeffrey D. Hartgerink. 2005. "Enzyme-Mediated Degradation of Peptide-Amphiphile Nanofiber Networks." *Adv. Mater.* vol. 17, pp. 2612-2617.

Knake, Rene, Amir W. Fahmi, Syed A. M. Tofail, Jason Clohessy, Miroslav Mihov, and Vincent J. Cunnane. 2005. "Electrochemical Nucleation of Gold Nanoparticles in a Polymer Film at a Liquid-Liquid Interface." *Langmuir.* vol. 21, No. 3, pp. 1001-1008.

Silva, Gabriel A. 2005. "Nanotechnology Approaches for the Regeneration and Neuroprotection of the Central Nervous System." *Surgical Neurology.* vol. 63, pp. 301-306.

Silva, Gabriel A. 2005. "Small Neuroscience: The Nanostructure of the Central Nervous System and Emerging Nanotechnology Applications." *Current Nanoscience.* vol. 1, No. 3, pp. 225-236.

Solis., F. J., S. I. Stupp, and M. Olvera de la Cruz. 2005. "Charge Induced Pattern Formation on Surfaces: Segregation in Cylindrical Micelles of Cationic-Anionic Peptide-Amphiphiles." *The Journal of Chemical Physics.* vol. 122, No. 5, 054905-1-054905-9.

Tovar, John D., Randal C. Claussen, and Samuel I. Stupp. 2005. "Probing the Interior of Peptide Amphiphile Supramolecular Aggregates." *Journal of the American Chemical Society.* vol. 127, No. 20, pp. 7337-7345.

Loudon, M. "Amino Acid Structures at Physiological pH." Printed Jun. 5, 2006. www.brynmawr.edu/Acads/Chem/mnerzsto/amino_acids.htm, amino_acids_2.gif, and amino_acids3.htm.

Hosseinkhani, Hossein, Mohsen Hosseinkhani, and Hisatoshi Kobayashi. Jul. 2006. "Design of Tissue-Engineered Nano scaffold Through Self-Assembly of Peptide Amphiphile." *Journal of Bioactive and Compatible Polymers.* vol. 21, No. 4, pp. 277-296.

Engler, Adam J., Shamik Sen, H. Lee Sweeney, and Dennis E. Discher. Aug. 25, 2006. "Matrix Elasticity Directs Stem Cell Lineage Specification." *Cell.* vol. 126, pp. 677-689.

Hoke, Ahmet. Aug. 2006. "Mechanisms of Disease: What Factors Limit the Success of Peripheral Nerve Regeneration in Humans?" *Nature Clinical Practice Neurology.* vol. 2, No. 8, pp. 448-454.

Brunsveld, L., J. Kuhlmann, and H. Waldmann. 2006. "Synthesis of Palmitoylated Ras-Peptides and—Proteins." *Methods.* vol. 40, pp. 151-165.

Elgersma, Ronald C., Tania Meijneke, Remco de Jong, Arwin J. Brouwer, George Posthuma, Dirk T. S. Rijkers, and Rob M. J. Liskamp. 2006. "Synthesis and Structural Investigations of N-alkylated β-peptidosulfonamide-peptide Hybrids of the Amyloidogenic Amylin(20-29) Sequence: Implications of Supramolecular Folding for the Design of Peptide-Based Bionanomaterials." *Organic & Biomolecular Chemistry.* vol. 4, pp. 3587-3597.

Guler, Mustafa O., Lorraine Hsu, Stephen Soukasene, Daniel A. Harrington, James F. Hulvat, and Samuel I. Stupp. 2006. "Presentation of RGDS Epitopes on Self-Assembled Nanofibers of Branched Peptide Amphiphiles." *Biomacromolecules.* vol. 7, No. 6, pp. 1855-1863.

Harrington, Daniel A., Earl Y. Cheng, Mustafa O. Guler, Leslie K. Lee, Jena L. Donovan, Randal C. Claussen, and Samuel I. Stupp. 2006. "Branched Peptide-Amphiphiles as Self-Assembling Coatings for Tissue Engineering Scaffolds." *Journal of Biomedical Materials Research Part A.* pp. 157-167.

Hosseinkhani, Hossein, Mohsen Hosseinkhani, Ali Khademhosseini, Hisatoshi Kobayashi, and Yasuhiko Tabata. 2006 "Enhanced Angiogenesis Through Controlled Release of Basic Fibroblast Growth Factor from Peptide Amphiphile for Tissue Regeneration." *Biomaterials.* vol. 27, pp. 5836-5844.

Kokkoli, Efrosini, Anastasia Mardilovich, Alison Wedekind, Emilie L. Rexeisen, Ashish Garg, and Jennifer A. Craig. 2006. "Self-Assembly and Applications of Biomimetic and Bioactive Peptide-Amphiphiles." Soft Matter. vol. 2, pp. 1015-1024.

Mardilovich, Anastasia, Jennifer A. Craig, Matthew Q. McCammon, Ashish Garg, and Efrosini Kokkoli. 2006. "Design of a Novel Fibronectin-Mimetic Peptide-Amphiphile for Functionalized Biomaterials." *Langmuir*. vol. 22, No. 7, pp. 3259-3264.

Paramonov, Sergey E., Ho-Wook Jun, and Jeffrey D. Hartgerink. 2006. "Self-Assembly of Peptide-Amphiphile Nanofibers: The Roles of Hydrogen Bonding and Amphiphilic Packing." *Journal of the American Chemical Society*. vol. 128, No. 22, pp. 7291-7298.

Rajangam, Kanya, Heather A. Behanna, Michael J. Hui, Xiaoqiang Han, James F. Hulvat, Jon W. Lomasney, and Samuel I. Stupp. 2006. "Heparin Binding Nanostructures to Promote Growth of Blood Vessels." *Nano Letters*. vol. 6, No. 9, pp. 2086-2090.

Reches, Meital and Ehud Gazit. 2006. "Molecular Self-Assembly of Peptide Nanostructures: Mechanism of Association and Potential Uses." *Current Nanoscience*. vol. 2, No. 2, pp. 105-111.

Stendahl, John C., Mukti S. Rao, Mustafa O. Guler, and Samuel I. Stupp. 2006. "Intermolecular Forces in the Self-Assembly of Peptide Amphiphile Nanofibers." *Advanced Functional Materials*. vol. 16, pp. 499-508.

"AccessScience Search Results. Amphiphile." Accessed online May 7, 2007. http://www.accessscience.com/search/asearch? location=titlestext&newSearch=1&pubpriv=private&categories= dictionary& categval=dictionary&text=amphiphile. McGraw-Hill Encyclopedia of Science & Technology Online.

Behanna, Heather A., Kanya Rajangam, and Samuel I. Stupp. 2007. "Modulation of Fluorescence Through Coassembly of Molecules in Organic Nanostructures." *Journal of the American Chemical Society*. vol. 129, No. 2, pp. 321-327.

Meijer, Joris T., Marjolijn Roeters, Valentina Viola, Dennis W. P. M. Löwik, Gert Vriend, and Jan C. M. van Hest. 2007. "Stabilization of Peptide Fibrils by Hydrophobic Interaction." *Langmuir*. vol. 23, No. 4, pp. 2058-2063.

The LabRatcom. 2007, updated. Hank's Buffered Salt Solution (HBSS) Recipe. http://www.thelabrat.com/protocolsHanks.shtml. Printed Jan. 19, 2007. pp. 1-2.

Invitrogen. Printed Jan. 22, 2008. "Dulbecco's Modified Eagle Medium (D-MEM) (1X) Liquid (High Glucose)." http://www.invitrogen.com/content.cfm?pageId=95&fuseaction=MediaForm. dsp_mediaForm&productId . . . .

Uniprot entry for Q899Z6. Printed Mar. 14, 2008. http://www.pir.uniprot.org/cgi-bin/upEntry?id=Q899Z6_CLOTE. 3 pages.

Niece, Krista L., Catherine Czeisler, Vibhu Sahni, Vicki Tysseling-Mattiace, Eugene T. Pashuck, John A. Kessler, and Samuel I. Stupp. 2008. "Modification of Gelation Kinetics in Bioactive Peptide Amphiphiles." Biomaterials. vol. 29, pp. 4501-4509.

Wayback Machine. http://www.archive.org/web/ entry, 1 page for http://www.northwestern.edu/provost/students/research_symposium/program2004.pdf retrieved on Oct. 14, 2009.

Cui, Honggang, Takahiro Muraoka, Andrew G. Cheetham, and Samuel I. Stupp. 2009. "Self-Assembly of Giant Peptide Nanobelts." Nano Letters. vol. 9, No. 3, pp. 945-951.

Martin, Ivan, R. Suetterlin, W. Baschong, M. Heberer, G. Vunjak-Novakovic, and L. E. Freed. 2001. "Enhanced Cartilage Tissue Engineering by Sequential Exposure of Chondrocytes to GF-2 During 2D Expansion and BMP-2 During 3D Cultivation." Journal of Cellular Biochemistry. vol. 83, pp. 121-128.

Oteiza, Patricia I., Gerardo G. Mackenzie, and Sandra V. Verstraeten. 2004. "Metals in Neurodegeneration: Involvement of Oxidants and Oxidant-Sensitive Transcription Factors." Molecular Aspects of Medicine. vol. 25, pp. 103-115.

Shen, Qin, Susan K. Goderie, Li Jin, Nithin Karanth, Yu Sun, Natalia Abramova, Peter Vincent, Kevin Pumiglia, and Sally Temple. May 28, 2004. Science. vol. 304, pp. 1338-1340.

Yang, Zhengqin, Sufen Yang, Steven Y. Qian, Jau-Shyong Hong, Maria B. Kadiiska, Raymond W. Tennant, Michael P. Waalkes, and Jie Liu. 2007. "Cadmium-Induced Toxicity in Rat Primary Mid-brain Neuroglia Cultures: Role of Oxidative Stress from Microglia." Toxicological Sciences. vol. 98, No. 2, pp. 488-494J.

Xia, Qing, Xudong Feng, Haifeng Huang, Lingyan Du, Xiaoda Yang, and Kui Wang. Dec. 20, 2010 (Accepted date). "Gadolinium-Induced Oxidative Stress Triggers Endoplasmic Reticulum Stress in Rat Cortical Neurons." Accepted Article for Journal of Neurochemistry. 23 pages.

Löwik, Dennis W. P. M., Jeffrey G. Linhardt, P. J. Hans M. Adams, and Jan C. M. van Hest. 2003. "Non-Covalent Stabilization of a β-Hairpin Peptide into Liposomes." Org. Biomol. Chem. vol. 1, pp. 1827-1829.

PCT International Search Report and Written Opinion mailed Sep. 21, 2010 for corresponding PCT Application No. PCT/US2010/030955.

Sampson, Wayne R., Heather Patsiouras, and Nicholas J. Ede. 1999. "The Synthesis of 'Difficult' Peptides Using 2-Hydroxy-4-Methoxybenzyl or Pseudoproline Amino Acid Building Blocks: a Comparative Study." Journal of Peptide Science. vol. 5, pp. 403-409.

Jun, Ho-Wook, Virany Yuwono, Sergey E. Paramonov, and Jeffrey D. Hartgerink. 2005. "Enzyme-Mediated Degradation of Peptide-Amphiphile Nanofiber Networks." Advanced Materials. vol. 17, pp. 2612-2617.

Kirkham, J., A. Firth, D. Vernals, N. Boden, C. Robinson, R. C. Shore, S. J. Brookes, and A. Aggeli. 2007. "Self-Assembling Peptide Scaffolds Promote Enamel Remineralization." J. Dent. Res. vol. 86, No. 5, pp. 426-430.

Stryker, Lori. 2008. "Titanium Dioxide: Toxic or Safe?" The Organic Make-up Company Inc. www.organicmakeup.ca/ca/titaniumdioxide.asp. 4 pages. Printed Aug. 25, 2010.

"Artificial Nerves for Regeneration of Motor Nerves." 2000. Clinical Neuroscience, vol. 18, No. 11, pp. 50-53.

Cheng, Hu et al. "Solid-Phase Synthesis of Thymosin α1." 2004. Journal of Nanjing University of Technology, vol. 26, No. 2, pp. 78-80. (no translation available.).

Elkstrom, Per A.R. et al. "Involvement of α7β1 Integrin in the Conditioning-Lesion Effect on Sensory Axon Regeneration." 2003. Molecular and Cellular Neuroscience, vol. 22, pp. 383-395.

Igaku, Jikken. "Regeneration of Peripheral Nerves." 2002. Experimental Medicine, vol. 20, No. 5, pp. 178-184.

Nouha, Rinsho. "Spinal Regeneration." 2001. Clinical Electroencephalography, vol. 43, No. 12, pp. 809-814.

Orthopale.com. "Debridement, Abrasion and Microfracture for Osteoarthritis of the Knee." Last updated Sep. 12, 2007. Accessed online Aug. 16, 2012. 2 pages.

Silva, Gabriel A. et al. "Selective Differentiation of Neural Progenitor Cells by High-Epitope Density Nanofibers." Feb. 27, 2004. Science, vol. 303, pp. 1352-1355 + Supplemental Online Material (6 pages).

Temenoff, Johnna S. and Antonios G. Mikos. "Review: Tissue Engineering for Regeneration of Articular Cartilage." 2000. vol. 21, pp. 431-440.

Toba, Toshinari, Tatsuo Nakamura, and Yasuhiko Shimizu. "Peripheral Nerve Regeneration Using a Polyglycolic Acid (PGA)—Collagen Nerve Conduit Filled with Collagen Sponge: Experimental Research and Human Application." 2003. Connective Tissue, vol. 35, pp. 45-52.

Webber, Matthew J. et al. "Supramolecular Nanostructures that Mimic VEGF as a Strategy for Ischemic Tissue Repair." Aug. 16, 2011. PNAS, vol. 108, No. 33, pp. 13438-13443.

Notification Concerning Transmittal of International Preliminary Report on Patentability from corresponding PCT Application No. PCT/US2010/030955, including the International Preliminary Report on Patentability dated Oct. 27, 2011, 5 pages.

* cited by examiner

SEQ ID NO:4

His-Ser-Asn-Gly-Leu-Pro-Leu-Gly-Gly-Gly-Ser-Glu-Glu-Glu-Ala-Ala-Ala-Val-Val-Val-(Lys)-dodecanoyl Molecular Weight = 2202.5 g/mol

SEQ ID NO:8 palmitoyl-Val-Val-Val-Ala-Ala-Ala-Glu-Glu-Glu-OH

Molecular Weight: 1154.39 g/mol

PEPTIDE-BASED SCAFFOLDS FOR CARTILAGE REGENERATION AND METHODS FOR THEIR USE

RELATED APPLICATIONS

This application claims priority from U.S. Provisional Application No. 61/168,894, filed Apr. 13, 2009, which is incorporated herein by reference in its entirety.

FIELD OF THE INVENTION

The present invention relates generally to new peptide-based gels and their therapeutic use to enhance articular cartilage regeneration. More particularly, the present invention relates to a mixture of self-assembling peptide amphiphiles (PA) having a peptide epitope sequence capable of non-covalently binding to transforming growth factor beta (TGF-$\beta$1). Hydrogel scaffolds composed of this peptide amphiphile and autologous cells are shown to enhance the regeneration of articular cartilage in an in vivo rabbit model. This is the first example of a self-assembling peptide amphiphile gel that can be used alone or as a therapy to augment current orthopedic strategies used clinically for cartilage defect repair, as in the context of microfracture or autologous chondrocyte transplantation.

BACKGROUND OF THE INVENTION

Techniques of tissue engineering employing biocompatible scaffolds provide viable alternatives to materials currently used in prosthetic and reconstructive surgery. These materials also hold promise in the formation of tissue or organ equivalents to replace diseased, defective, or injured tissues. In addition, biocompatible scaffolds can be used to form biodegradable materials that may be used for controlled release of therapeutic materials (e.g. genetic material, cells, hormones, drugs, or pro-drugs) into a predetermined area. However, most polymers used today to create these scaffolds, such as polylactic acid, polyorthoesters, and polyanhydrides, are difficult to control and result in, among other things, poor cell attachment and poor integration into the site where the tissue engineered material is utilized. Accordingly, focus has shifted to scaffolds formed from synthetic biomolecules, more particularly biomimetic scaffolds capable of in situ self-assembly.

The preparation of any synthetic material with structure on the nanoscale that mimics natural tissue is a challenging problem. One approach has been to prepare molecules that spontaneously assemble into fibrils similar in morphology to the proteins and proteoglycans that compose the natural extracellular matrix. In contrast to most synthetic biopolymers, the use of small, self-assembling molecules facilitates control of chemical and structural properties of these macromolecular assemblies.[1-12] To that end, peptide amphiphiles have been shown to self-assemble under suitable conditions to form fibril-like micelles (referred to in the art as "nanofibers"), such nanofibers having particular utility as biocompatible scaffolds, more particularly in the area of tissue engineering.[13-26] Previously disclosed peptide amphiphiles have been described as having peptide sequences identified through phage display methodology that are capable of non-covalently binding growth factors.[27] [U.S. patent application Ser. No. 11/005,552, "Self-assembling peptide amphiphiles and related methods for growth factor delivery", the entirety of which is included herein by reference] It is an object of the present invention to provide novel peptide amphiphiles that are superior to previously reported compounds, including modifications that elicit lower cytotoxicity and greater biocompatibility with chondrogenic cell types, more homogenous peptide blending and gelation under physiological conditions, while retaining the previously identified capability to bind the chondrogenic growth factor TGF-$\beta$1.[27] It is a further object of the present invention to provide a method of using said improved TGF-$\beta$1 binding peptide amphiphiles to repair or regenerate defects in articular cartilage in vivo.[49] This method represents a novel and potentially beneficial therapeutic treatment for patients with cartilage lesions (defects) on their joint surfaces resulting from acute injury or chronic degeneration.

Untreated articular cartilage lesions lead to pain, dysfunction, and accelerated osteoarthritis. Full thickness focal chondral lesions may progress to osteoarthritis, a disorder having an estimated economic impact approaching $65 billion in the U.S., when considering healthcare costs, loss of wages, and societal impact costs.[28] Chondral lesions are found in a wide range of the population, including both the athletic cohort and older active patients. In a retrospective review of 31,516 knee arthroscopies, Curl et. al. found 53,569 cartilage lesions in 19,827 patients undergoing arthroscopy (2.7 lesions per knee, prevalence=63%).[29] In a prospective study of 993 consecutive knee arthroscopies, Aroen et al. found an 11% incidence of focal chondral injuries.[30] In knees that had any articular cartilage lesions, 20% were full thickness focal chondral lesions.

Focal articular cartilage lesions have limited regenerative potential. Several treatment modalities are currently in clinical use. The regenerative potential of untreated articular cartilage is limited to the formation of a fibrocartilage scar. Surgical strategies to regenerate hyaline or hyaline-like articular cartilage include abrasion arthroplasty; microfracture; implantation of cells, tissue, synthetics; and osteochondral plugs. Clinical and histological outcome studies of these techniques have demonstrated varying, and often confounding clinical results. Long term histological studies have demonstrated that the majority of the tissue regenerated in all of these techniques is fibrous with partial at best, often with no hyaline cartilage produced.[31]

The limited self-healing capability of articular cartilage is largely due to the nature of the tissue. First, the avascularity of articular cartilage cannot support the formation of a fibrin clot. In vascularized tissues, this clot serves as a temporary matrix and a source of growth factors to stimulate natural healing, as seen in tissues such as in skin and bone. Second, the dense extracellular matrix (ECM) of articular cartilage restricts chondrocyte migration to the defect space. Third, chondrocytes have low mitotic activity, which results in insufficient cell proliferation and matrix synthesis for complete regeneration. With this limited natural healing capability, clinical intervention is necessary to prevent further articular cartilage degradation and early progression of degenerative osteoarthritis.

Microfracture is a common clinical procedure used for the repair of cartilage defects. The proposed benefits of microfracture are that it is a single-surgery procedure, relatively simple and cost-effective with low patient morbidity, and involves the patients' own mesenchymal stem cells (MSCs) as a cell source to facilitate cartilage regeneration. Its current clinical indications are in non-obese patients with a small, full-thickness contained focal defect. Another proposed benefit of microfracture is that it does not preclude the use of other cartilage restoration techniques at a later time. The regenerative process in microfracture involves a clot of multipotent MSCs that adhere to the subchondral bone. Histological assessment of microfracture in animal models and clinical testing have shown that over time most lesions substantiate into fibrous cartilage with predominant Type I collagen and limited Type II collagen. Additionally, clinically there is a significant decrease in functional outcome 18 months post-surgery, as well as in patients that are more than 40 years old.[32] This suggests that there is deficient bioactivity, quantity, quality, and retention of chondrocyte cell phenotype within the defect. Additionally, there may be a paucity in the quantity of the extracellular matrix and availability of endogenous growth factors to induce chondrocyte differentiation.

Osteochondral transplantation (allograft and autograft) is another method whereby osteochondral graft plugs are used to recreate the chondral surface. While hyaline-like cartilage has been seen in a few reports, there is a high rate of failed integration of the graft with the surrounding cartilage.[33] Donor site morbidity for autografts as well as other issues inherent with allograft (immunogenicity, strength of subchondral bone, chondrocyte viability, healing potential, bone integration, cost) have affected clinical and histological outcomes.[34-36]

Other techniques for cartilage regeneration include cell implantation, with or without tissue engineered constructs. Clinical investigations have involved cell harvesting, expansion into monolayer and combination with a matrix or scaffold, followed by implantation. These techniques require a two-stage surgery, with a significantly higher cost and increased morbidity from the harvest site. Recently, clinical trials have retrospectively and prospectively evaluated these more advanced techniques with microfracture and shown equivocal results. In a long-term prospective randomized control trial, Knutsen et. al. found a 23% failure rate in each group at 5 years and more failures in the ACI group than microfracture at two years.[37] 33% of patients at 5 years had radiographic evidence of arthritis. In a recent systematic review of treatment of focal knee articular cartilage defects Magnussen et al. conclude that there is not one technique that is superior to another in clinical or histological evaluation.[38] Clearly no clinical solution has been found that can provide a large percentage of patients with excellent outcomes at long term follow-up.

A proposed solution to the above challenges is a one-stage procedure that has limited morbidity, technical simplicity, and promotes retention of the chondrocyte phenotype in an articular defect by providing both a three-dimensional scaffold and appropriate chondrogenic growth factors with a high degree of bioactivity. The scaffold would ideally maximize chondrocyte and growth factor integration, viability, and function.

SUMMARY OF THE INVENTION

Accordingly, it is an object of the present invention to provide compositions and methods of using self-assembling peptide amphiphiles (PA) as scaffolds or matrices to promote the regeneration of tissue more closely resembling the histological, biochemical, and architectural properties of hyaline cartilage. PAs having a peptide sequence with a propensity for strong, specific binding to transforming growth factor (TGF)-β1 were examined in combination with microfracture for the repair of articular cartilage defects in a rabbit model. Among all possible 7-mer peptide sequences, the peptide HSNGLPL (SEQ ID NO:1) was identified using phage display methodology as a strong, specific binding sequence for recombinant TGF-β1.[27, 39, 40] In the phage display technique, the peptide is displayed on the bacteriophage with the His at the free N-terminus and the C-terminal Leu is coupled to the protein coat of the phage through a GGGS (SEQ ID NO:2) spacer peptide. In a preferred embodiment of the present invention, the "TGF-binding" peptide and the spacer peptide are further attached to a beta-sheet forming peptide, which is conjugated to a fatty acid that promotes aggregation and beta-sheet self-assembly of the peptide, thereby resulting in a fibrillar nanostructure matrix. Though not intending to be bound by theory, this structure may serve to mimic the presentation of the TGF-binding peptide on the bacteriophage, but using a wholly synthetic peptide structure. This synthetic, self-assembling scaffold can be used as a delivery vehicle for exogenous, recombinant-human TGF-β1 (rhTGF-β1), localizing and prolonging it bioavailability; or it can be used as an in vivo gel matrix to concentrate and protect endogenous TGF-β1 released by cells into a cartilage defect during microfracture or ACI procedures. The peptide amphiphile nanofibers themselves can also serve as a scaffold to promote clot formation, retention, survival and differentiation of cells, be they mesenchymal stem cells (MSCs) or autologous chondrocytes.

TGF-β1 has a significant role in the regulatory network of growth factors that maintains articular cartilage in the differentiated phenotype.[41] Additionally, TGF-β1 is a necessary and critical factor for inducing chondrogenesis in marrow-derived MSCs.[42] In articular cartilage tissue engineering, TGF-β1 has been shown to increase collagen and proteoglycan production and inhibit matrix breakdown.[43] Though not intending to be bound by theory, the addition of a TGF-binding peptide to a peptide-amphiphile nanofiber scaffold can enhance the chondrogenic influence of the scaffold in vivo. As demonstrated herein, when a self-assembled peptide scaffold is applied to an articular cartilage defect after microfracture, which allows bone marrow containing MSCs to infiltrate the defect, the scaffold successfully promotes cartilage matrix production and the regeneration of hyaline-like cartilage.

Accordingly, it is an objective of the present invention to provide self-assembling scaffolds for cartilage regeneration, such scaffolds taking the form of a nanofibrous matrix or gel composed of an aqueous mixture of "TGF-binding" peptide-amphiphile (PA) molecules and other, non-specific peptide amphiphile molecules (here termed 'filler' PAs). The TGF-β1 binding peptide amphiphiles of the present invention include, at a minimum, the following segments: (1) a growth factor binding peptide segment selected from one or more related peptides identified through phage display methodology; (2) a spacer segment that confers both solubility and flexibility to the peptide; (3) a structural peptide segment that confers the molecule with the ability to form a beta-sheet secondary structure, and (4) a lipophilic segment, composed generally of a single alkyl chain.

It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

While it is an object of the present invention to provide a peptide amphiphile composition that binds the growth factor TGF-β1, it will be understood by those skilled in the art that, due to the varying sequence homology among extracellular signaling proteins in the TGF superfamily, a peptide amphiphile that binds TGF-β1 may also bind more or less strongly other TGF-βisoforms, as well as a range of other proteins, including bone morphogenic proteins (BMPs), growth differentiation factors (GDFs), activins, inhibins, glial derived neurotrophic factor (GDNF), Nodal and Lefty.[44]

It is anticipated that one or more of these proteins may find use in the system described, be they exogenously delivered, recombinant proteins or endogenous factors whose biological activity is influenced or altered by the presence of the peptide amphiphile. Therefore, references herein to "TGF-binding" should not be construed to limit the scope of the described invention to a single protein or growth factor.

It is, furthermore, an object of the present invention to provide a peptide-amphiphile (PA) molecule as described above, wherein the spacer segment includes the amino acid sequence "$(Gly)_m Xaa(Xbb)_n$,", wherein m and n are integers that independently range between 0 and 5, more preferably between 1 and 3, wherein Xaa is any amino acid (serine in a preferred embodiment), and wherein Xbb is an amino acid residue selected from those with acidic side-chains, including, for example, glutamic acid (E) and aspartic acid (D). The use of this spacer peptide segment facilitates homogenous blending with other peptide amphiphiles containing amino acid residues with acidic side-chains, and provides adequate gelation strength under physiological conditions.

In an alternative embodiment, the spacer segment may contain a non-peptide component, such as an alkyl segment (e.g. 6-aminohexanoic acid) or a polyethylene glycol segment (PEG). Such a non-peptide spacer may modify the solubility or degradation rate of the compound in vivo.

It is a further object of the present invention to provide peptide-amphiphile molecules as described above, wherein the structural peptide segment includes the amino acid sequence "$(Ala)_p(Val)_q$", wherein p and q are integers that range independently between 0 and 6, more preferably between 2 and 4. It is yet another object of the present invention to provide peptide amphiphile molecules as described above wherein the lipophilic segment is a saturated alkane ranging from six to twenty-two carbons in length, and is more preferably twelve or sixteen carbons in length.

One particularly preferred compound that is well suited for use as a scaffold for cartilage regeneration has the following peptide sequence:

```
HSNGLPLGGGSEEEAAAVVVK    (SEQ ID NO: 3)
```

When conjugated to a preferred lipophilic component, the peptide amphiphile containing this sequence has the following structure:

```
HSNGLPLGGGSEEEAAAVVV(K)-CO(CH2)10CH3   (SEQ ID NO: 4)
```

In this embodiment, the TGF-binding peptide (HSNGLPL) (SEQ ID NO:1) is presented at the N-terminus of the peptide sequence, with the histidine residue as a free amine; the spacer segment is GGGSEEE (SEQ ID NO:5); the beta-sheet forming segment is AAAVVVK (SEQ ID NO:6), and the lipophilic segment is a dodecyl (twelve-carbon) saturated fatty acid conjugated to the epsilon amine on the side-chain of the C-terminal lysine (K). This structure is shown schematically in FIG. 1a.

It is also an object of the present invention to provide mixtures of the TGF-binding peptide amphiphile and a non-specific 'filler' peptide amphiphile. Mixing in this fashion enables the concentration of the TGF-binding peptides to be varied independently and in a controlled manner from the overall concentration of peptide amphiphile nanofibers. While not intending to be bound by theory, mixing or 'diluting' the TGF-binding peptide with a filler PA may facilitate nanofiber assembly and growth factor binding to the self-assembled structure. Furthermore, appropriate selection of the 'filler' PA may lead to improved biocompatibility with chondrogenic cell types, more homogenous blending with the TGF-binding PA and improved gelation under physiological conditions; however, determining the optimum combination involves only routine experimentation and thus is well within ordinary skill. In a preferred embodiment, the filler PA has the following structure:

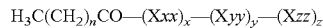

where Xxx and Xyy are amino acids with non-polar side-chains, Xzz is an amino acid with an acidic side-chain, n is an integer ranging from 4 to 20, and x, y, and z are integers that can range independently from 2 to 6. In a more preferred embodiment, Xxx is valine, Xyy is alanine, Xzz is glutamic acid and n=14. An even more preferred embodiment of the filler PA has the peptide sequence VVVAAAEEE (SEQ ID NO:7). When conjugated to a preferred lipophilic segment this peptide amphiphile has the following structure:

```
H3C(CH2)14CO-VVVAAAEEE    (SEQ ID NO: 8)
```

In this embodiment, the lipophilic segment is palmitic acid, which is conjugated to the N-terminus of the peptide. The C-terminus of the peptide is a free acid. The structure of this compound is illustrated schematically shown in FIG. 1b.

It is a further object of the present invention to provide a composition composed of one or more peptide amphiphiles self-assembled to form one or more non-spherical micelles, for example cylindrical micelles, examples of which include, but are not limited to, nanofibers. The composition may include a mixture of TGF-binding peptide amphiphiles and 'filler' peptide amphiphiles, as described above. These amphiphiles may in principle be mixed in any ratio, though in a preferred embodiment they are mixed in a molar ratio of 1:9 (i.e. one TGF-binding PA molecule per nine filler molecules). The composition may also take the form of a substrate provided with self-assembled non-spherical micelles over at least a portion of the substrate, for example as a coating of nanofibers disposed thereon. This substrate may consist of an orthopedic implant, scaffold, or other device intended for use in the repair or replacement of musculoskeletal tissues.

It is a further object of the present invention to provide biocompatible, biodegradable gels composed of peptide amphiphiles and/or peptide-amphiphile compositions, such gels being useful in the creation of scaffolds or matrices, which may or may not include isolated cells, into a human patient to create or induce the body to create a tissue equivalent. Such gels can promote cell engraftment and provide three-dimensional templates for cartilage regeneration. The resulting tissue is expected to be similar in composition and histology to naturally occurring cartilage tissue, in contrast to fibrocartilage or scar tissue that generally results in the absence of intervention, during the body's natural healing process following creation of a full-thickness articular cartilage defect.

To that end, the present invention provides in one embodiment a self-assembling peptide-amphiphile solution than can be directly injected into a target site within a human patient, wherein the self-assembled peptide-amphiphile gel organizes into a fibrillar scaffold or matrix. In one embodiment, the self-assembling peptide solution may be mixed with bone marrow derived MSCs in situ to form a gel-clot. In another embodiment, cells such as autologous chondrocytes may be suspended in a self-assembled peptide-amphiphile gel that is pre-formed into a matrix outside the body, which then can be implanted into a human patient. Ultimately, the self-assembled peptide-amphiphile gel degrades, leaving only the resulting tissue. In yet another embodiment of the present invention, the peptide-amphiphiles of the present invention are used in conjunction with other tissue engineering materials, either as a gel, solid, or liquid and are used to template cartilage tissue growth on one or more of the articular surfaces of a joint in a human patient.

One of skill in the art will readily recognize that a gel or solid composed of these nanofibers under physiological conditions of pH, temperature and tonicity affords the opportunity to utilize this material for a wide range of purposes and in a number of different potential biomedical and tissue engineering applications.

Accordingly, in one embodiment, the present invention provides a method of treating a patient with tissue engineered material that includes the step of administering a peptide amphiphile composition to a target site on the patient in need of a tissue engineered material.

It is a further object of the present invention to provide methods and compositions for altering (e.g., augmenting or stimulating) differentiation and growth of cells (e.g., mesenchymal stem cells and chondrocytes). In particular, the present invention relates to compositions composed of one or more self-assembling peptide amphiphiles (e.g., in solution) that generate (e.g., self-assemble into) nanofibers that are able to encapsulate cells and promote chondrogenesis and subsequent cartilage matrix expression (e.g., cartilage regeneration) and methods of using the same. Compositions and methods of the present invention find use in research and clinical (e.g., therapeutic) settings. It is a further object of the present invention to provide pharmaceutical compositions composed of one or more peptide amphiphiles, such as those described in FIG. 1.

These and other objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art having knowledge of various amphiphilic compounds, self-assembly techniques and peptide synthesis. Such objects, features, benefits and advantages will be apparent from the above as taken into conjunction with the accompanying examples, data, figures and all reasonable inferences to be drawn there from, alone or with consideration of the references incorporated herein.

BRIEF DESCRIPTION OF THE DRAWINGS

Various aspects and applications of the present invention will become apparent to the skilled artisan upon consideration of the brief description of the figures and the detailed description of the present invention and its preferred embodiments which follows.

DETAILED DESCRIPTION OF THE PREFERRED EMBODIMENTS

Figure 1:
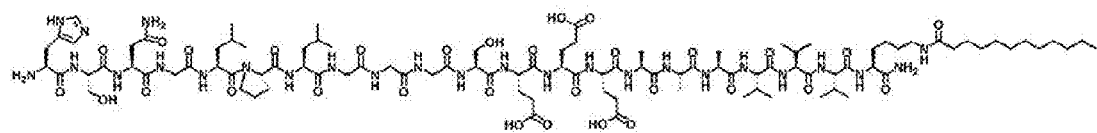
FIG. 1 depicts the chemical structures of peptide amphiphiles (PA) referred to herein as the "TGF-binding PA" (SEQ ID NO:4) and the "filler PA" (SEQ ID NO:8).
Figure 1:
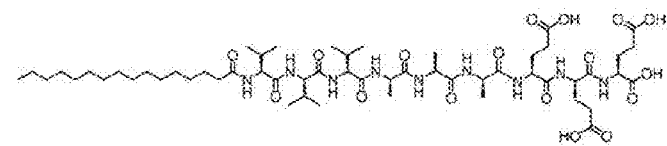

Although any methods and materials similar or equivalent to those described herein can be used in the practice or testing of embodiments of the present invention, the preferred methods, devices, and materials are now described. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the present invention, the following definitions apply:

As used herein and in the appended claims, the singular forms "a", "an" and "the" include plural reference unless the context clearly dictates otherwise. Thus, for example, reference to a "cell" is a reference to one or more cells and equivalents thereof known to those skilled in the art, and so forth.

As used herein, the term "nanofiber" refers to an elongated or threadlike filament having a diameter of equal to or less than 100 nanometers.

As used herein, the term "cylindrical micelle" refers to a colloidal aggregate with a non-spherical, high-aspect-ratio shape (length/diameter>10), composed of amphiphilic molecules in which the hydrophobic (or lipophilic) part of the amphiphiles forming the micelle tends to locate away from the polar phase (e.g. water) while the polar parts of the molecule (head groups) tend to locate at the micelle-solvent interface.

As used herein, the term "physiological conditions" refers to the range of conditions of temperature, pH and tonicity (or osmolality) normally encountered within tissues in the body of a living human.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties of those components.

As used herein, the terms "scaffold" and "matrix" refer interchangeably to a natural or synthetic structure or meshwork of structures with open porosity that is extended in space and provides mechanical or other support for the growth of living tissue, either in the body or in vitro.

As used herein, the term "gel" refers to a semi-solid, viscoelastic material (capable of resisting some mechanical stress without deformation), which is formed by the coagulation of a colloidal liquid, composed of a fibrous matrix and fluid-filled interstices.

As used herein, the term "peptide amphiphile" refers to a molecule that, at a minimum, includes a non-peptide lipophilic segment, and a peptide segment having at least six amino acid residues. The peptide amphiphile may express a net charge at physiological pH, either a net positive or negative net charge, or may be zwitterionic (i.e., carrying both positive and negative charges).

As used herein and in the appended claims, the term "lipophilic segment" refers to the hydrocarbon moiety disposed on or about the terminus of the peptide amphiphile. This lipophilic segment may be herein and elsewhere referred to as the hydrophobic component or hydrophobic segment. The lipophilic segment should be of a sufficient length to provide amphiphilic behavior and micelle formation in water or another polar solvent system.

Accordingly, in the context of the present invention, the lipophilic segment is preferably composed of a single, saturated, linear alkyl chain of the formula: $C_nH_{2n-1}O$—, where n=6–22. In a preferred embodiment, this lipophilic segment may be covalently linked via a peptide bond to N-terminal amine of the peptide, or to the epsilon amine of a C-terminal lysine residue.

As used herein and in the appended claims, the term "spacer segment" refers to an intermediate amino acid sequence of the peptide amphiphile molecule that confers both solubility and flexibility to the peptide. In a preferred embodiment, the spacer segment includes the amino acid sequence "$(Gly)_m Xaa(Xbb)_n$", wherein m and n are integers that range between 0 and 5, more preferably between 1 and 3, wherein Xaa is any amino acid (serine in a more preferred embodiment), and wherein Xbb is an amino acid residue selected from those with acidic side-chains, including, for example, glutamic acid (E) and aspartic acid (D). In the context of the present invention, one particularly preferred spacer segment has the amino acid sequence GGGSEEE (SEQ ID NO:5). This spacer segment is utilized in the exemplary peptide amphiphile SEQ ID NO:4, which has the following structure:

HSNGLPL

Increasing or decreasing the length of the acidic amino acid residue's side-chain can also modify the solubility of peptide amphiphiles containing that residue, as can changing the number of carboxylic acid groups on the side-chain. Accordingly, the present invention contemplates a peptide-amphiphile molecule wherein Xbb (as described above) is an alpha-substituted amino acid with 1 to 5, more preferably 1 to 3 carbon atoms between the alpha carbon and one or more carboxylic acid residues. In a preferred embodiment, X is selected from aminomalonic acid (Ama), aspartic acid (Asp), glutamic acid (Glu), aminoadipic acid (Aib), aminoheptanedioic acid (Apm) or gammacarboxyglutamic acid (Gla).

As used herein and in the appended claims, the term "structural peptide segment" refers to the intermediate amino acid sequence of the peptide amphiphile molecule generally composed of three to ten amino acid residues with non-polar, uncharged side chains, selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), Gly (G), (listed in order of their propensity to form beta sheets). However, non-naturally occurring amino acids of similar beta-sheet forming propensity may also be used. In a more preferred embodiment, a strong and a weak beta sheet former are used in combination, for example taking the form $(X_A)_{Na} (X_B)_{Nb} (X_C)_{Nc}$, where $X_A$ and $X_B$ are selected from A, L, V and G, Xc is any amino acid, Na and Nb are 2, 3 or 4 and Nc ranges from 0 to 3. Illustrative examples include (SEQ ID NOs:9-20)

| VVVAAA | AAAVVV | LLLAAA | VVVVVV |
| VVVLLL | LLLVVV | AAAAAA | AAAAGGG |
| LLLLLL | AAAGGG | LLLGGG | AAALLL |

In a preferred embodiment, $X_C$ is an amino acid residue with an amine-terminated side-chain, including but not limited to lysine or ornithine, wherein the amine functionality of said side-chain facilitates attachment of the lipophilic segment to the peptide. In the context of the present invention, one particularly preferred structural peptide segment has the amino acid sequence AAAVVVK (SEQ ID NO:6). This structural segment is utilized in the exemplary peptide amphiphile SEQ ID NO:4, which has the following structure: HSNGLPLGGGSEEEAAAVVV(K)—CO(CH$_2$)$_{10}$CH$_3$ As used herein, the term "growth factor" refers to the broad class of bioactive polypeptides that control and regulate a variety of endogenous biological and cellular processes, such as cell-cycle progression, cell differentiation, reproductive function, development, motility, adhesion, neuronal growth, bone morphogenesis, wound healing, immune surveillance and cell apoptosis. Growth factors typically operate by binding to specific receptor sites on the surface of target cells. Growth factors include, but are not limited to, cytokines, chemokines, polypeptide hormones and the receptor-binding antagonists thereof. Examples of well known growth factors include but are not limited to:

Transforming growth factor beta (TGF-β);
Bone Morphogenic Protein (BMP);
Interleukin-17;
Transforming growth factor alpha (TGF-α);
Cartilage oligomeric matrix protein (COMP);
Cell Density Signaling Factor (CDS);
Connective tissue growth factor (CTGF);
Epidermal growth factor (EGF);
Erythropoietin (EPO);
Fibroblast growth factor (FGF);
Glial Derived Neurotrophic Factors (GDNF);
Granulocyte-colony stimulating factor (G-CSF);
Granulocyte-macrophage colony stimulating factor (GM-CSF);
Growth differentiation factor (GDF);
Myostatin (GDF-8);
Hepatocyte growth factor (HGF);
Insulin-like growth factor (IGF);
Macrophage inhibitory cytokine-1 (MIC-1);
Placenta growth factor (PlGF);
Platelet-derived growth factor (PDGF);
Thrombocyte concentrate (PRP);
Thrombopoietin (TPO);
Vascular endothelial growth factor (VEGF);
Activin and Inhibin;
Coagulogen;
Follitropin;
Gonadotropin and Lutropin;
Mullerian Inhibiting Substance (MIS) also called: Anti-Müllerian hormone (AMH) Müllerian inhibiting factor (MIF) and Mullerian inhibiting hormone (MIH);
Nodal and Lefty; and
Noggin Therapeutic molecules that regulate, induce or participate in useful biological processes in the body, including those listed above, are often categorized or classified according to their particular structure or function. For example, immunoregulatory proteins secreted by cells of the immune system, such as interleukin and interferon, are often referred to as cytokines. Other categories of regulatory molecules include, but are not limited to:

morphogens (e.g., molecules that regulate or control the formation and differentiation of tissues and organs);
chemokines (e.g., any of a group of cytokines produced by various cells, as at sites of inflammation, that stimulate chemotaxis in white blood cells such as neutrophils and T cells);
hormones (e.g., a product of living cells that circulates in body fluids such as blood and produces a specific, often stimulatory effect on the activity of cells, usually remote from its point of origin);
receptors (e.g., a molecule present on a cell surface or in the cell interior that has an affinity for a specific chemical entity, including both endogenous substances such as hormones and ligands as well as foreign materials, such as viral particles, that serves as an intermediary between the stimulating agent and the downstream physiological or pharmacological response thereto);
receptor-binding agonists (e.g., a chemical substance capable of combining with a specific receptor on a cell and initiating the same reaction or activity typically produced by the endogenous binding substance (such as a hormone)); and
receptor-binding antagonists (e.g., a chemical substance that reduces the physiological activity of another chemical substance (such as a hormone) by combining with and blocking one or more receptors associated therewith).

While the present invention finds particular use in connection with the growth factor TGF-β1, those skilled in the art that the principles of the present invention may be readily applied to the binding of other growth factors.

As used herein and in the appended claims, the term "growth factor binding peptide" refers to an N-terminally disposed peptide sequence composed of 7 amino acid residues, wherein the peptide is identified as a strong and specific binding sequence for a particular growth factor using phage display methodology. Upon self-assembly, the growth factor binding peptide is exposed at the surface of the nanofiber, thereby serving as a bioactive signal presented to the environment.

Examples of growth factor binding peptide sequences suitable for use in the context of the peptide amphiphile of present invention include, but are not limited to those described in U.S. Patent Application 2005-0209145, "Self-assembling peptide amphiphiles and related methods for growth factor delivery" as binding sequences for TGF-β1 derived using phage display (SEQ ID NOs:21-29):

| HSNGLPL | SHSYNRL | TPLHRYV | TDWTSVR |
| HIWRPAP | ATPSTTR | STPPYKG | ATVSKWA |
| KQIPSPL |         |         |         |

In principle, sequences derived from phage display may be capable of binding a growth factor in either C-terminal or N-terminal orientation. Reversing the polarity of the above sequences generates a second set of growth factor binding peptides (SEQ ID NOs:30-38):

| LPLGNSH | LRNYSHS | VYRHLPT | RVSTWDT |
| PAPRWIH | RTTSPTA | GKYPPTS | AWKSVTA |
| LPSPIQK |         |         |         |

As will be understood by one skilled in the art of peptide chemistry, other variations on the growth factor binding sequence are possible and may lead to peptide amphiphiles with increased or decreased strength and selectivity of binding to the growth factor TGF-β1. These include substituting one or more of the non-polar amino acid residues (L, I, V, G or A), with another, similarly non-polar residue, or substituting a positively charged R residue with a K residue (or vice versa).

In addition, cyclic peptides, formed through cross-linking of two or more amino acid residues in the above described peptides, may be useful for the applications described above. In a preferred embodiment, an amine functional group of the HSNGLPL peptide (SEQ ID NO: 1), for example the N-terminal amine, the histadine side-chain, or asparagine, may be cross-linked with a hydroxyl functional group elsewhere in the peptide, for example to any one of the serine or glutamic acid residues in SEQ ID NO: 4. While not intending to be bound by theory, such cross-linking results in cyclic presentation of the TGF-β1 binding domain, which may in turn protect the N-terminal residue from enzymatic degradation by aminopeptidases, and thus result in enhanced biological signalling or protein binding by the peptide.

Peptide sequences of the present invention include amino acid residues that may be subject to post-synthesis modification. For example, the deamidation of asparagine, Asn (N), via a succinimide intermediate is a common post-translational protein modification resulting in the transformation of the Asn side-chain to that of aspartic acid, Asp (D), or isoaspartic acid, isoAsp (D*). This modification is associated in some instances with an altered (enhanced or reduced) effect on biological activity of the substrate protein. Moreover, synthetic peptides containing Asn residues can undergo deamidation during manufacturing, particularly when exposed to alkaline pH and elevated temperatures. In the case of therapeutic peptides, this process may lead to altered (enhanced or reduced) efficacy. Thus an embodiment of the present invention is to modify the above TGF-β1 binding sequences such that Asn residues are replaced with Asp or isoAsp, such as HSDGLPL (SEQ ID NO. 39) or HSD*GLPL (SEQ ID NO.40), where D* is isoaspartic acid. In a preferred embodiment, these modified sequences are incorporated into a peptide amphiphile as described previously, such as HS DGLPLGGGSEEEAAAVVV(K)—$CO(CH_2)_{10}CH_3$. (SEQ ID NO. 41)

Amino acids useful in the peptide amphiphiles of the present invention include, but are not limited to, naturally occurring amino acids and artificial amino acids. Incorporation of artificial amino acids such as beta or gamma amino acids and those containing non-natural side chains, and/or other similar monomers such as hydroxyacids are also contemplated, with the effect that the corresponding component is peptide-like in this respect.

The peptide amphiphile molecules and compositions of the present invention can be synthesized using preparatory techniques well-known to those skilled in the art, preferably, by standard solid-phase peptide synthesis, with the addition of a fatty acid in place of a standard amino acid at the N-terminus of the peptide, or at the epsilon amine of a lysine side-chain, utilizing orthogonal protecting groups, as would be known to one skilled in the art. The fatty acid is typically covalently linked to the amine through a peptidyl bond. Synthesis typically starts from the C-terminus, to which amino acids are sequentially added using either a Rink amide resin (resulting in an —$NH_2$ group at the C-terminus of the peptide after cleavage from the resin), or a Wang resin (resulting in an —OH group at the C-terminus). Accordingly, the present invention encompasses peptide amphiphiles having a C-terminal moiety that may be selected from the group consisting of —H, —OH, —COOH, —$CONH_2$, and —$NH_2$.

In aqueous solutions, PA molecules self-assemble into cylindrical micelles that bury the lipophilic segment in their core and display the growth factor binding peptide on the surface. The structural peptide undergoes intermolecular hydrogen bonding to form beta sheets that orient parallel to the long axis of the micelle. The cylindrical micelles (also referred to as nanofibers) can form gels in water or various aqueous media under physiological conditions at concentrations ranging typically from 0.5 to 4 wt %.

To induce self-assembly of an aqueous solution of peptide amphiphiles, the pH of the solution may be changed (raised or lowered) or multivalent ions or charged polymers or other macromolecules may be added to the solution. Though not intending to be bound by theory, self-assembly is facilitated in the instant case by the neutralization or screening (reduction) of electrostatic repulsion between ionized side chains on the functional peptide segment. These cylindrical micelles formed by self-assembly can be viewed as fibrils or high-aspect-ratio nanostructures in which the functional peptide segment is repetitively displayed on the surface of the micelle.

In one embodiment, the present invention provides a method of treating a patient with a tissue engineered material that includes the step of administering a peptide amphiphile composition to a target site, particularly a full thickness defect in the cartilaginous component of one or more articular surfaces of a joint in a human patient being treated for symptoms of such a cartilage lesion. It is a further object of the present invention to provide methods and compositions for altering (e.g., augmenting or stimulating) differentiation and growth of cells (e.g., mesenchymal stem cells and chondrocytes). In particular, the present invention relates to compositions composed of one or more self-assembling peptide amphiphiles (e.g., in solution) that generate (e.g., self-assemble into) nanofibers that are able to encapsulate cells and promote chondrogenesis and subsequent cartilage matrix expression (e.g., cartilage regeneration) and methods of using the same. Compositions and methods of the present invention find use in research and clinical (e.g., therapeutic) settings. It is a further object of the present invention to provide pharmaceutical compositions composed of one or more peptide amphiphiles.

In an alternative embodiment, the peptide amphiphile composition may be administered to treat a cartilage defect or deficiency in a non-human animal. For example, this method envisions veterinary use in treating cartilage defects in the knee joints of horses, however other large mammals (dogs, sheep, goats, cows) may benefit from this treatment.

The composition may be administered in any manner suitable to direct the peptide amphiphile composition to the site of a cartilage defect or deficiency, including by direct placement of a pre-formed gel during an open arthrotomy or during an arthroscopic procedure by injection of an aqueous solution containing said peptide amphiphiles. Said cartilage defect or deficiency may be due to acute injury of the articular joint surface, a degenerative condition such as osteoarthritis, or a combination of both. Said gel may be formed in situ in a human patient or non-human animal, or may be pre-formed outside the body by combining one or more liquid components. These liquid components are used to dissolve the peptide amphiphiles and to induce self-assembly, and may include components to change the pH of the solution or include multivalent ions (including but not limited to calcium chloride), charged polymers or other charged macromolecules. The liquid components may also be combined outside the body (in vitro) with cells. These cells may be obtained from blood, bone marrow aspirate, or other autologous tissue from the intended patient. Once formed, said gel may be placed into a cartilage defect or otherwise applied to the articular surface of said patient. In one preferred embodiment, the composition is administered by direct injection or arthroscopically.

The peptide amphiphile composition may be administered alone or in conjunction with another orthopedic surgical procedure, such as one intended to repair, restore or regenerate damaged or missing cartilage. For example, the composition may be used to augment another clinical strategy for cartilage defect repair, particularly following debridement of a lesion on the articular surface of a joint in a patient.

In one preferred embodiment, the peptide amphiphile composition is suitably administered as an adjuvant to a microfracture procedure that releases blood and marrow-derived cells from the subchondral bone into the cartilage defect site. In this context, the composition mixes with the autologous blood and cells released from the osteochondral bone or marrow during the microfracture procedure to form a gel-clot suited to cartilage regeneration.

In an alternate embodiment, the peptide amphiphile composition is suitably administered as an adjuvant to chondrocyte implantation (ACI). In this context, the composition may be combined with autologous chondrocytes to form a gel scaffold that retains the beneficial cells in the lesion site.

In yet a further embodiment, the peptide amphiphile composition is suitably administered as an adjuvant to an open osteochondral allograft transplantation (OATS). In this context, the composition may be used to form a gel in the lesion site.

In another embodiment, the invention is directed to kits comprising a peptide amphiphile of the present invention. The kit may allow for either the in vivo formation of self-assembled micelles or the in vitro self-assembly of micelles formed from the peptide amphiphile for insertion into the patient. A kit directed to the in vivo formation of micelles will suitably be compiled to allow the practitioner to assemble the components into an injectable formulation for administration to the patient. This kit may comprise a syringe, a container of the peptide amphiphile, and optionally a container of a growth factor, such as TGF-β1, or other reagent to induce gelation, such as calcium chloride. Optionally, the peptide amphiphile is contained in a pre-filled syringe to which the TGF-β1 is subsequently added. In addition, the in vivo kit may further comprise a syringe to extract cells from the patient, which cells may be combined with the peptide amphiphile, growth factors or other components to form the injectable formulation. A kit directed to the in vitro administration of the peptide amphiphile may comprise the peptide amphiphile, a container comprising one or more aqueous components used to dissolve and subsequently to induce self-assembly of the peptide amphiphile (such as through changing the pH of the solution or through the presence of multivalent ions, charged polymers or other charged macromolecules), and optionally the growth factor, TGF-β1. Optionally, the kit may contain a substrate upon which to coat with the self-assembled micelles prior to insertion into the patient. Optionally, the in vitro kit may further comprise a syringe to extract cells from the patient, which cells may be combined with the peptide amphiphile, aqueous component, and TGF-β1. Each of the components in the kits may suitably be kept in separate containers until the practitioner is ready to prepare the formulation for administration into the patient.

Accordingly, the present invention provides the first example of a self-assembling peptide amphiphile gel that can be used alone or in the context of microfracture or autologous chondrocyte transplantation.

Hereinafter, the present invention is described in more detail by reference to the Examples. However, the following materials, methods and examples only illustrate aspects of the invention and in no way are intended to limit the scope of the present invention. As such, methods and materials similar or equivalent to those described herein can be used in the practice or testing of the present invention.

EXAMPLES

Example 1

Automated Synthesis and Purification of Peptide Amphiphiles Containing the TGF-Binding Segment HSNGLPL (SEQ ID NO:1), Including SEQ ID NO:4

1.1 Reagents:

The following reagents, or equivalents, were used as received: HBTU (2-(1H-Benzotriazol-1-yl)-1,1,3,3-tetramethyluronium hexafluorophosphate), piperidine, DIEA (n,n,-diisopropylethlamine), DMF (n,n-dimethylformamide), DCM (dichloromethane), TFA (trifluoroacetic acid), TIS (triisopropylsilane). All water was purified by reverse osmosis and filtered using a Millipore™ system to a resistivity of 18.2 Mohm-cm. 9-Fluorenylmethoxycarbonyl (Fmoc) protected amino acids and orthogonally protected Fmoc-Lys(Mtt)-OH were purchased from EMD Biosciences (La Jolla, Calif.). Peptides were synthesized on Rink amide resin (loading 0.6-0.75 mmole/g).

1.2 Peptide Synthesis:

Peptides were synthesized via solid-phase methodology on an automated peptide synthesizer (CS Bio Co. model 136XT), using a 250 mL glass reaction vessel which was inverted 180° every two seconds for the duration of each reaction step, in order to fully expose the resin to each reagent. The resin was first swelled in DCM and DMF, and then Fmoc deprotection was performed with 30 vol % piperidine in DMF solution for 10 min, repeated twice. Amino acid couplings were done with 4.0 equivalents of the Fmoc-protected amino acid (0.5 M in DMF), 3.8 equivalents HBTU (0.475 M in DMF) and 6.0 equivalents of DIEA (0.75 M in DMF) for 1 hr per coupling. Each solution was combined and pre-activated by bubbling with high purity nitrogen gas for 3 minutes prior to being added to the resin-containing reaction vessel. Each coupling was performed once. For a 1 mmole reaction scale, 30 mL of solution was used for each deprotection and washing step. All reagents were stored and reactions performed under high purity nitrogen gas. Multiple DCM and DMF washing steps were done between each reaction step. The first amino acid coupled to the Rink amide resin was an orthogonally protected Fmoc-Lys(Mtt)-OH. After coupling, the Mtt protecting group was selectively removed with 1% TFA in DCM. The fatty acid lipophilic component of the peptide amphiphile was coupled to the epsilon amine of the Lys as described above, except 2.0 equivalents of the dodecanoic acid was dissolved in a 50/50 mixture of DMF/DCM and combined with 1.9 equivalents of HBTU and 3.0 equivalents of DIEA in DMF. This coupling was repeated three times, after which the product was checked for free amines by the ninhydrin reaction (also known as the 'Kaiser test') and the reaction repeated if necessary to obtain a negative result for free amines. After the fatty acid was attached, the remaining peptide sequence was synthesized as described, progressing from C- to N-terminus. After the peptide portion of the molecule was synthesized as described, the N-terminus of the peptide was deprotected and left as a free amine.

1.3 Resin Cleavage:

Peptide-loaded resin was transferred to a 200 mL glass shaker vessel, where cleavage and deprotection from the resin was carried out with ca. 50 mL of a mixture of TFA:TIS:water in ratio of 95.0:2.5:2.5 for 3 hours. The peptide amphiphile solution was then decanted into a round-bottom flask and the TFA removed by rotary evaporation while heating the solution to 40° C., using a collector at −78° C. (dry ice/isopropanol) and an ultimate pressure of ca. 20 mtorr. Rotary evaporation was halted prior to complete dryness, and the remaining viscous peptide solution (typically <1 mL) triturated with ca. 200 mL of cold (−20° C.) diethyl ether. The solution was agitated to ensure good mixing of then re-cooled to −20° C. overnight to allow complete precipitation. The resulting precipitated peptide amphiphile was collected in a medium fritted glass funnel, washed three times with cold ether (ca. 200 mL) and dried under vacuum (<20 in. Hg).

1.4 Purification:

Peptide amphiphiles were dissolved at 20 mg/mL in an aqueous solution with sufficient ammonium hydroxide to obtain a pH of 9. This solution was purified in 5 mL aliquots using an Agilent, Inc. model 1100 preparative HPLC equipped with a Phenomenex, Inc. Gemini® 5 μm C18 column (100×30 mm). An elution gradient of water and acetonitrile (each containing 0.1 vol % ammonium hydroxide buffer) was used. The flow rate was 15 mL/min, and the mobile phase was pre-heated to ca. 45° C. using a Timberline Instruments TL-105 column heater. UV-absorption was monitored at 220 nm wavelength, and the eluent of the primary peak collected.

1.5 Lyophilization:

To remove the water and acetonitrile following preparative HPLC, peptide amphiphile solutions were transferred to a glass lyophilization flask, shell frozen in a dry ice/isopropanol bath at −78° C., and lyophilized for at least 48 hrs on a freeze-dryer operating at a collector temperature of −80° C. and a pressure of <0.100 mbar. Typical yields of purified peptide amphiphile were 60-75% of theoretical yield, with a typical 1 mmole reaction scale yielding circa 1.0-1.5 g of material with a peptide purity of approximately 90%.

1.6 pH Adjustment:

The lyophilized peptide amphiphile powder was weighed and re-dissolved in USP pharmaceutical grade water at a concentration of 10 mg/mL. A solution of 1 M sodium hydroxide (NaOH), prepared from USP pharmaceutical grade NaOH and water, was filtered through a sterile 0.2 micron PTFE syringe filter. pH of the suspension was adjusted by the addition of small aliquots of the NaOH solution to a range of pH 7.0-8.0, causing the peptide to go readily into solution.

Example 2

Synthesis of Filler Peptide Amphiphile $C_{16}H_{31}O$-VVVAAAEEE (SEQ. ID NO:8)

The filler PA was synthesized via automated solid phase peptide synthesis as described above, except a pre-loaded glutamic acid Wang resin was used. Additional amino acids were coupled as described, proceeding from C- to N-terminus. After coupling of the N-terminal valine, the peptide was capped with a palmitoyl moiety, which was accomplished as described in Example 1.2 by substituting palmitic acid for dodecanoic acid. Peptide cleavage from the resin, HPLC purification, aseptic filtration and lyophilization were performed as described in Examples 1.3-1.6.

Example 3

Chemical Characterization of Peptide Amphiphiles

Peptide amphiphiles were characterized as to identity and purity using mass spectroscopy (MS), high performance liquid chromatography (HPLC), and amino acid analysis (AAA), as described below.

3.1 Mass Spectroscopy

Figure 2A:
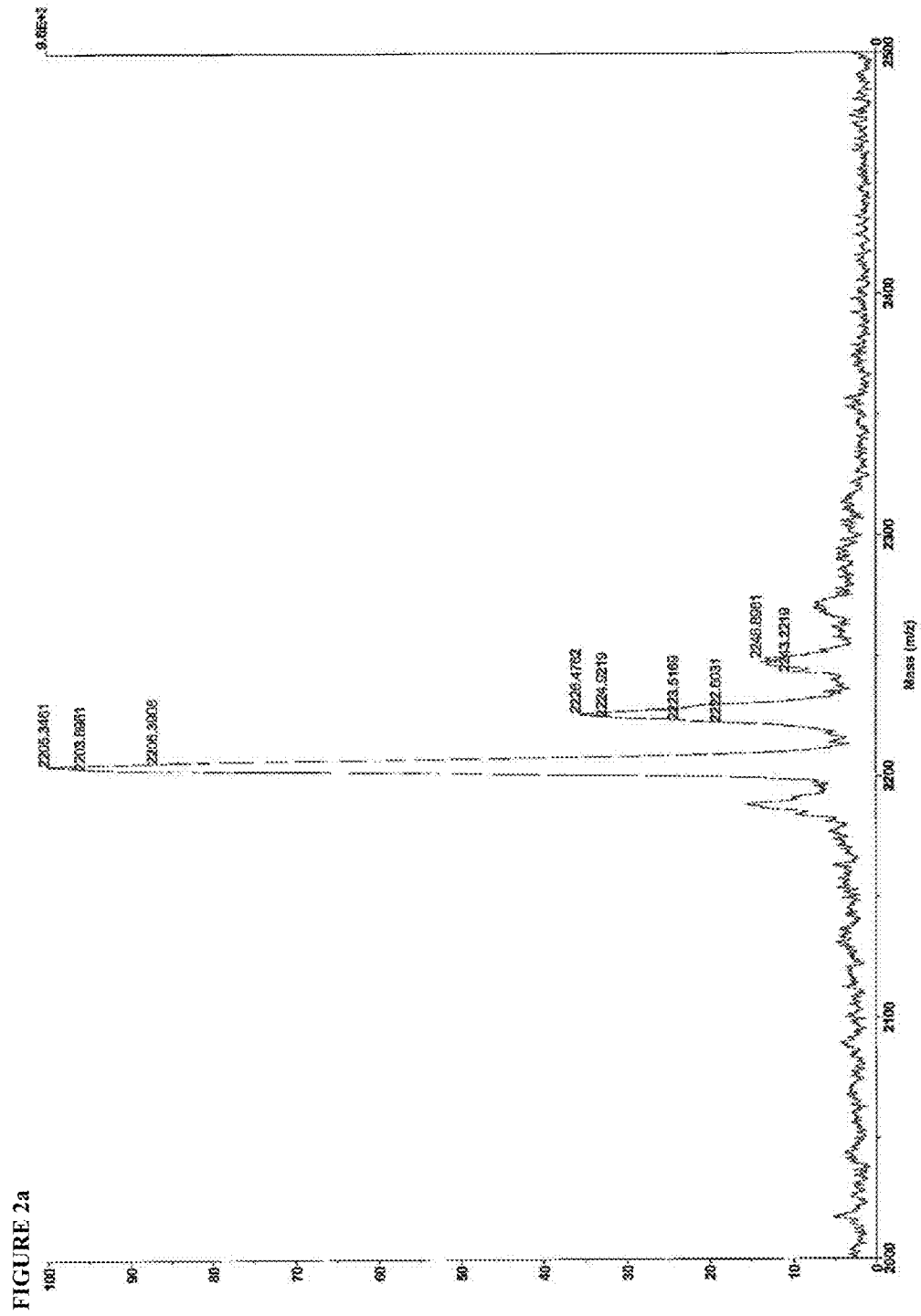
FIG. 2 depicts the results of MALDI-TOF mass spectroscopy of a TGF-binding PA (SEQ ID NO:4) and filler PA (SEQ ID NO:8). The expected mass is observed for each compound, as described in Example 3.
Figure 2B:
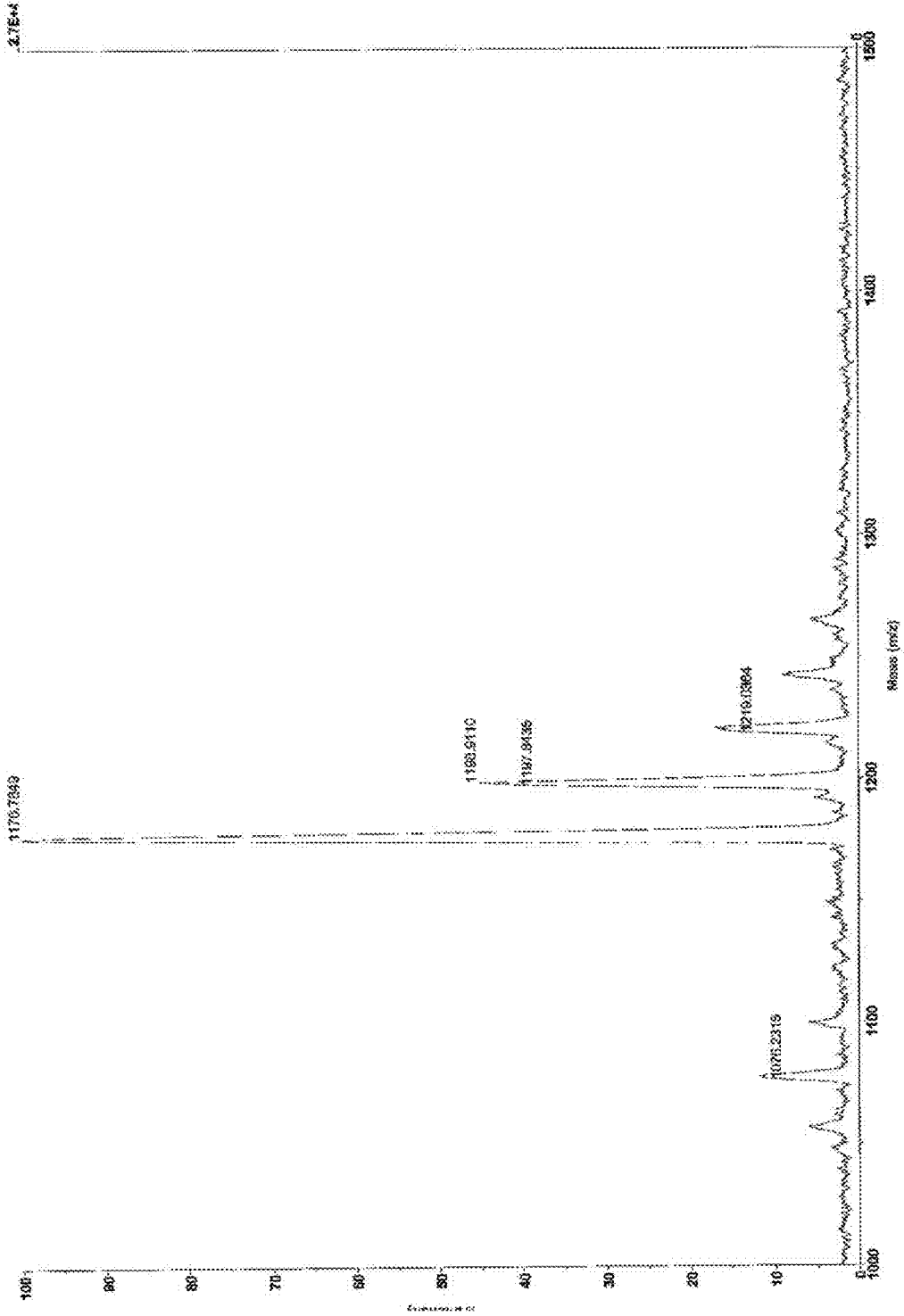

Identity of SEQ ID NO:4 and SEQ ID NO:8 were confirmed by matrix-assisted laser desorption-ionization time-of-flight mass spectroscopy (MALDI-TOF MS), using a Voyager DE-PRO instrument operating in positive ion mode, with CHCA matrix. 1 uL of a 1 mg/mL solution was spotted onto the MALDI plate. The mass spectra are shown in FIG. 2.

| SEQ ID. NO: 4 | | | |
|---|---|---|---|
| Expected m/z = 2201.22 | Found m/z = | 2203.90 | $[M + H^+]$ |
| | | 2226.48 | $[M - H + Na^+]$ |
| | | 2243.22 | $[M - H + K^+]$ |
| | | 2248.90 | $[M - H + 2Na^+]$ |
| SEQ ID. NO: 8 | | | |
| Expected m/z = 1153.68 | Found m/z = | 1176.78 | $[M - H + Na^+]$ |
| | | 1198.91 | $[M - H + 2Na^+]$ |
| | | 1198.92 | $[M - H + 3Na^+]$ |
| | | 1076.23 | Valine deletion |

3.2 Analytical HPLC

Figure 3A:
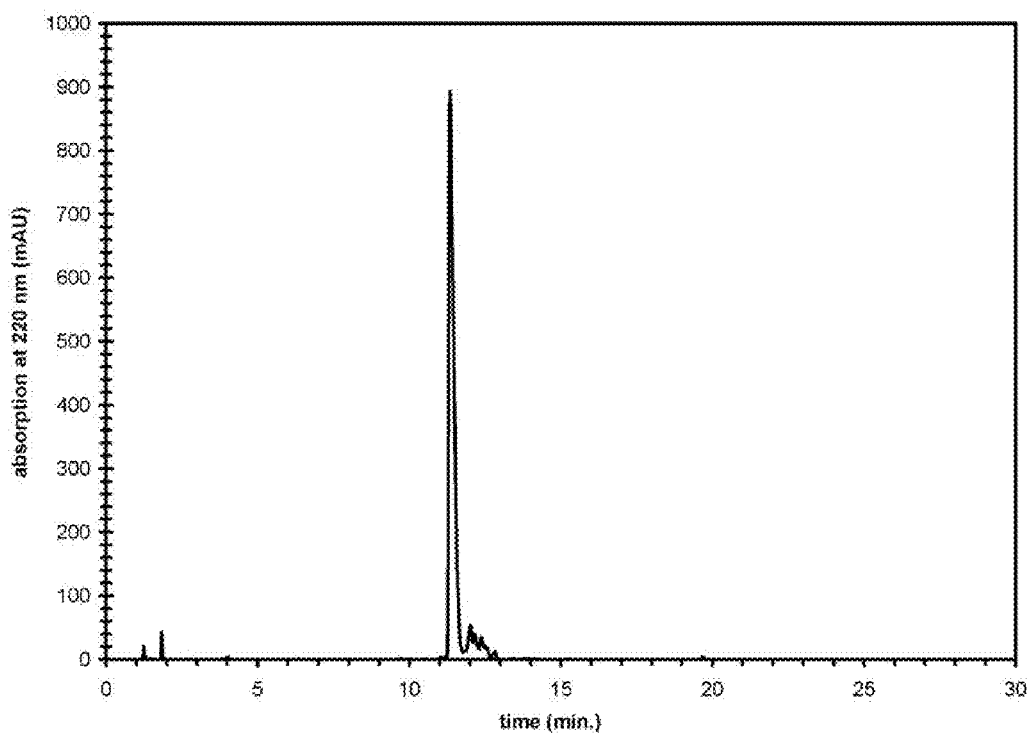
FIG. 3 shows analytical HPLC chromatographs of a TGF-binding PA (SEQ ID NO:4) and filler PA (SEQ ID NO:8), demonstrating the peptide purity of the two compounds, and discussed in Example 3.
Figure 3B:
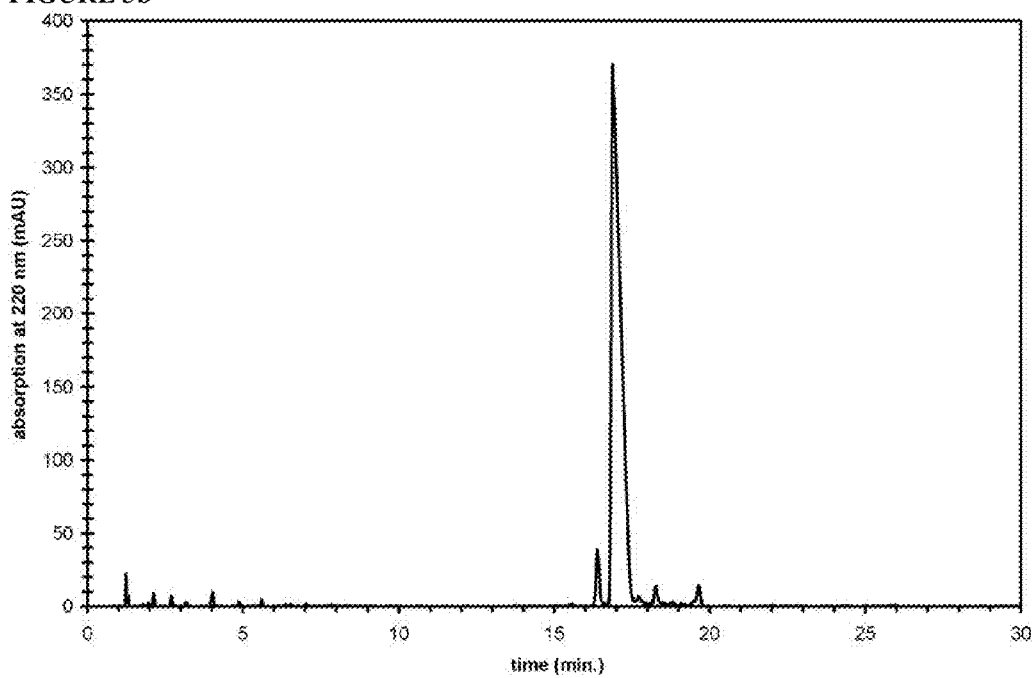

Analytical, reverse-phase HPLC was performed to determine the peptide purity of the molecules synthesized. HPLC was done using an Agilent 1100 analytical HPLC system equipped with a Phenomenex Inc. Gemini 5 um 110A reverse-phase C18 column (150×4.6 mm) heated to 60° C. A gradient elution was performed using a binary mobile phase of (A) $H_2O$ containing 2% v/v $CH_3CN$; 0.10% v/v $NH_4OH$; 20 mM $NH_4HCO_2$ and (B) $CH_3CN$ containing 2% v/v $H_2O$; 0.07% v/v $NH_4OH$. The gradient was run from 10-100% B over 30 min at a 1.25 mL/min flow rate. UV absorption was monitored at 220 nm wavelength following the injection of a 50 uL of a 1 mg/mL solution of the peptide amphiphile PA in water. Under these elution conditions, SEQ ID NO:4 exhibited a retention time of 11.34 min. and SEQ ID NO:8 exhibited a retention time of 16.88 min. Peptide purity of both compounds was approximately 90% as determined based on the integrated area-under-curve of the main elution peak. Chromatographs for both peptide amphiphiles are shown in FIG. 3.

3.3 Amino Acid Analysis

Peptide content and amino acid composition were determined by amino acid analysis. An aliquot of each peptide amphiphile was hydrolyzed in gas phase 6N HCl at 110° C. for 65 hr. Following hydrolysis, the aliquot was dried and redissolved in a borate loading buffer, and subjected to chromatographic analysis to determine the picomoles of each amino acid present, using a bovine serum albumin (BSA) protein standard for comparison.

The peptide content of SEQ ID NO:4 was found to be 77% by weight, with the amino acid composition given in Table 1. The results were consistent with the expected sequence within the resolution of the instrument used.

TABLE 1

| AAA of TGF-binding PA | | |
|---|---|---|
| Amino Acid Residue | Expected residues/mole | Found residues/mole |
| His | 1.0 | 0.77 |
| Ser | 2.0 | 1.48 |
| As(x) | 1.0 | 0.95 |
| Gly | 4.0 | 4.10 |
| Leu | 2.0 | 2.02 |
| Pro | 1.0 | 1.00 |
| Glu | 3.0 | 3.26 |
| Ala | 3.0 | 3.37 |
| Val | 3.0 | 3.22 |
| Lys | 1.0 | 1.09 |

The peptide content of SEQ ID NO:8 was found to be 73% by weight, with the amino acid composition listed in Table 2. The results were consistent with the expected sequence within the resolution of the instrument used.

TABLE 2

AAA of filler PA

| Amino Acid Residue | Expected residues/mole | Found residues/mole |
|---|---|---|
| Glu | 3.0 | 3.21 |
| Ala | 3.0 | 3.17 |
| Val | 3.0 | 2.80 |

Example 4

Figure 4:
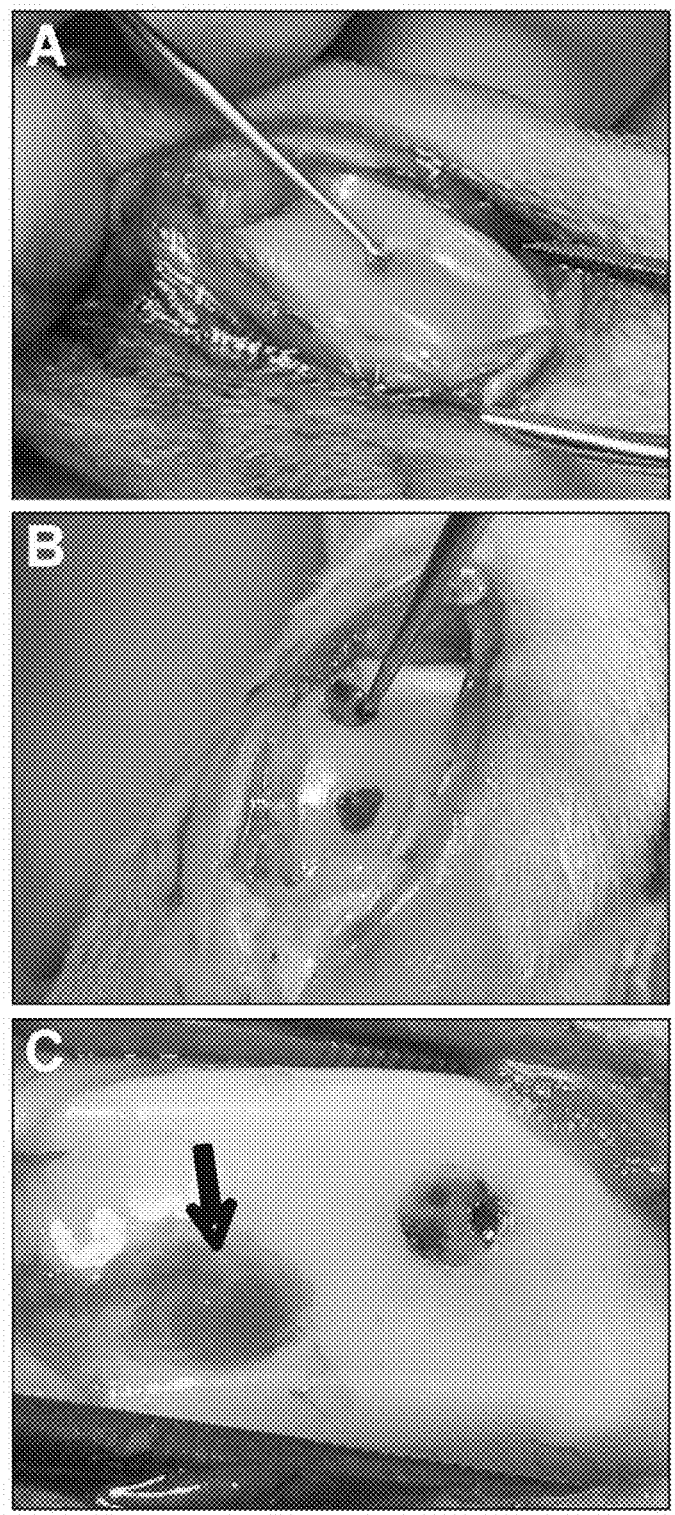
FIG. 4 shows photographs documenting: (a) the surgical creation of an articular cartilage defect in the knee of a rabbit; (b) the microfracture procedure and resulting marrow-blood released from the osteochondral bone into the defect site; and (c) the filling of one of the two defects (indicated by arrow) with a self-assembling peptide amphiphile gel composed of the TGF-binding PA and filler PA.

In Vivo Characterization of Peptide Amphiphiles as an Adjuvant to Microfracture to Enhance Cartilage Regeneration 4.1 Creation of Articular Cartilage Defect in Rabbit Model Animal study was conducted at Northwestern University (Chicago, Ill.) in accordance with a protocol approved by the University's Animal Care and Usage Committee (ACUC). Ten (10) male New Zealand White Rabbits (weighing 3-3.5 kg) were anesthetized by intramuscular injection of ketamine at 30-40 mg/kg and xylazine 5-7 mg/kg. Isoflourane (1-3%) and oxygen were supplied by face mask until the animal was induced to sedation and general anesthesia for the entire procedure. Life support monitoring was supervised by veterinarians at Northwestern University's Center for Comparative Medicine (CCM, Chicago, Ill.). Under sterile aseptic technique, a midline 2-cm incision was made with the knee flexed at 20 degrees and subsequently a medial parapatellar capsulotomy was performed and the patella was translated laterally to expose the articular surface of the trochlea. Two full thickness chondral defects 2-mm in diameter were created in the trochlea (proximal-medial and distal-lateral) using curettes. The articular cartilage, including the calcified cartilage layer, was completely removed and subchondral bone was exposed using a micro-curette as shown in FIG. 4a. Care was taken to not disrupt the subchondral bone, and sharp edges were created at the transition zone with the surrounding intact cartilage. Microfracture was performed within the defects by creating 3 holes spaced equally apart, and 2-mm deep to subchondral bone with a micro-awl. Marrow blood was seen emerging out of each microfracture hole and was allowed to infiltrate the cartilage defect (see FIG. 4b), which was then treated as described in Example 4.2 by application of the TGF-binding peptide amphiphile gel, or a control gel, with or without the addition of exogenous recombinant TGF-β1.

Post-operatively each rabbit was given intramuscular (IM) antibiotics (Baytril 72 hours duration) and IM pain medicine (Buprenex 24 hours duration). Signs of local or systemic infection were recorded as well as the general health and recovery of the rabbits. Rabbits were also evaluated for ability to weight bear and mobility within cages. At 12-weeks post-surgery rabbits were euthanized by injection of pentobarbital intravenously with a secondary measure of bilateral thoracotomy. Subsequently, the distal femur was harvested and processed for histological analysis.

4.2 Application of Peptide Amphiphile Gel to Cartilage Defect

Two full-thickness defects were created in each knee, resulting in 4 defects per rabbit (or 40 defects total for the 10 rabbits studied). Rabbit knees were divided into 4 groups, with both defects in each knee receiving the same treatment, and the contralateral knee serving as a control to account for any systemic effects. A total volume of 10 microliters (uL) of the test solutions were administered directly to each cartilage defect by micropipette, using sterile, disposable plastic tips. The treatment received by each group is summarized as follows:

Group 1: 10 uL of PBS with 1 ng of rhTGF-β1

Group 2: 8 uL of PBS with 1 ng of rhTGF-β1 and 0.10 mg of filler PA
   +2 uL of 0.5M $CaCl_2$ Group 3: 8 uL of PBS with 1 ng rhTGF-β1, 0.0175 mg of TGF-binding PA, and 0.0825 mg filler PA
   +2 uL of 0.5M $CaCl_2$ Group 4: 8 uL of PBS with 0.0175 mg of TGF-binding PA, and 0.0825 mg filler PA (no rhTGF-β1)
   +2 uL of 0.5M $CaCl_2$ In order to induce gelation of the peptide amphiphile solutions in situ in the defect site, 8 uL of a 12.5 mg/mL PA solution in phosphate-buffered saline (PBS) was administered followed immediately by 2 uL of a 0.5 M $CaCl_2$ (in water), resulting in a final concentration of 10 mg/mL of the peptide amphiphile and 100 mM $CaCl_2$. Recombinant human TGF-β1 (rhTGF-β1, Peprotech Inc.) was included in the PA solutions for Group 1, 2 and 3, in a concentration of 100 nm/mL, resulting in a total dose of 1 ng per defect at the treatment dose of 10 uL. For animals receiving the TGF-binding peptide amphiphile (SEQ ID NO:4) this molecule was mixed at 10 mol % with the filler peptide amphiphile (SEQ ID NO:8) (a 1:9 molecular ratio). Each defect received 0.1 mg total peptide amphiphile (10 mg/mL in a 10 uL dose), either filler PA alone (Group 2) or filler PA plus TGF-binding PA (Group 3 and 4).

4.3 Histological Analysis of Rabbit Joints

After the animals were sacrificed and tissue harvested at 12 weeks, extracted femur specimens were fixed in 10% neutral buffered formalin, decalcified for 24 hours, and the tissue processed for paraffin embedding. 4-μm thick sections were obtained from the center cross-sections of the defects (1 mm from the defect edge) and histochemically stained for hemotoxylin and eosin (H&E), Safranin-O/Fast Green; and immunohistochemically stained type II collagen. Histological grading of cartilage repair was performed by 3 independent, blinded observers, using a 24-point scale by O'Driscoll et al.[45]

4.4 Statistical Analysis and Determination of Sample Size

Sample size determination was based on an a priori power analysis of related in vivo cartilage regeneration studies utilizing similar control and experimental groups with similar histological and visual grading criteria. Minimal sample size per experimental group was determined with the following parameters: alpha<0.05 (CI≧95%); 1-β≧0.8. For the stated minimally accepted Type II error, a minimal sample size of five (defects) was required per group.

The significance of difference between the treatment groups was evaluated with one-way Analysis of Variance (ANOVA, F<0.05) testing with a Least Significance Difference (LSD) post-hoc test (p<0.05). Multivariate ANOVA testing was performed as well testing two or more variables (growth factor, PA type) among groups (p<0.05). Each defect was considered an independent sample. This method of sampling is supported by prior studies on the correlation of tissue type within each defect based on the location within the joint.[46]

4.5 Animal Observation and Gross Pathology

On gross examination, under sedation prior to sacrifice, each rabbit had full range of motion of the knee. One rabbit knee was noted to have dislocation of the patella that was not recognized until the day of sacrifice. That knee was not included in the analysis. All rabbits survived to the end point of the study. None of the rabbits in any of the groups developed grossly apparent degeneration or synovial hypertrophy of the joint.

Figure 5:
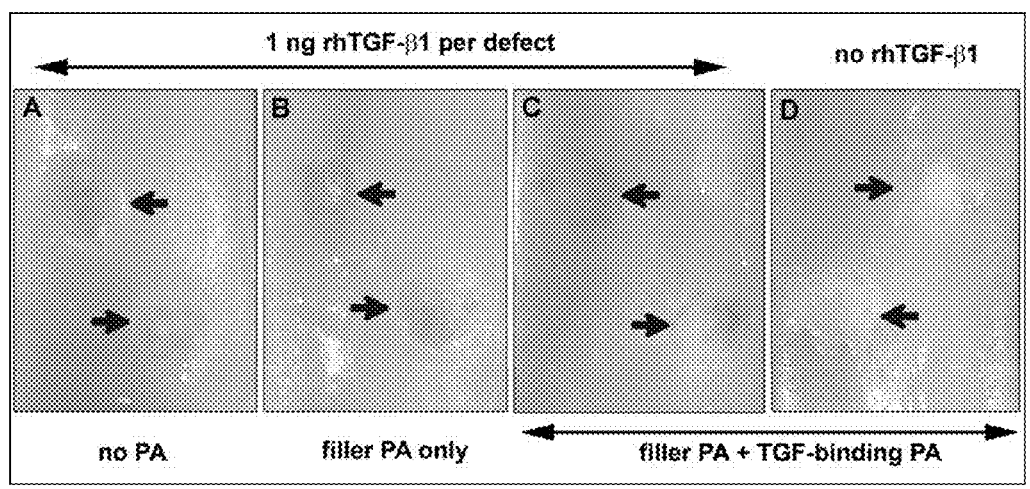
FIG. 5(a)-(d) are representative photographs from animals in treatment Group 1 through 4 (from left to right), showing the articular surface of the rabbit trochlea after sacrifice at the twelve week end-point of the study. The surgically created, circular cartilage defects are indicated by the small arrows. Images (c) and (d) show significantly more hyaline-like tissue filling the defects in animals treated with the TGF-binding PA.

There was no obvious macroscopic differences at 12 weeks between Group 1 and 2 (rhTGF-β1 alone or with filler PA) with regard to tissue fill or appearance of repair tissue. There was, however, observable improvement in animals receiving the TGF-binding PA, with or without exogenous rhTGF-β1 (Group 3 and 4). As show in FIG. 5, these groups exhibited greater defect fill with hyaline-like tissue, and a reduced appearance of the defect boundary, indicative of better integration with the surrounding tissue.

4.6 Histological Evaluation of Cartilage Regeneration

Figure 6:
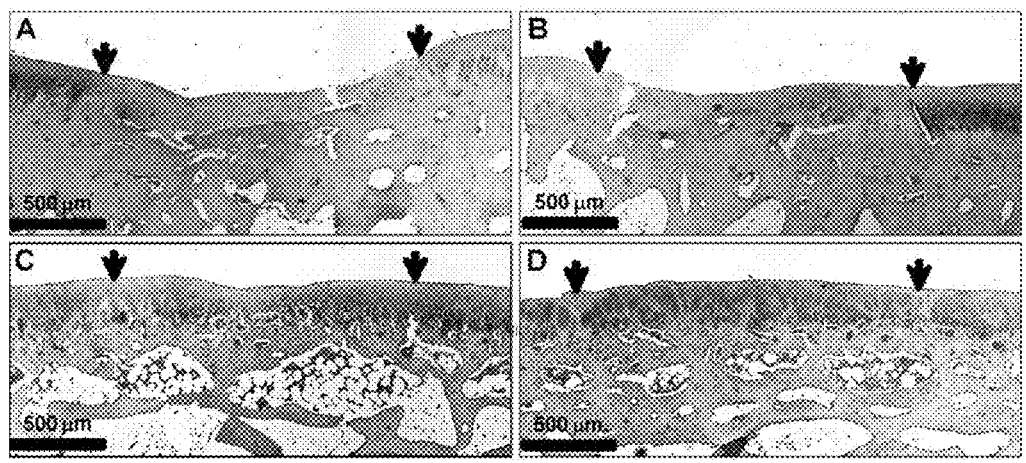
FIG. 6(a)-(d) are representative micrographs showing Safranin-O histological staining of tissue sections from animals in treatment Group 1 (upper left), Group 2 (upper right), Group 3 (lower left) and Group 4 (lower right). Each section is through the center of one cartilage defect, harvested at 12 weeks. Small arrows indicate the approximate edges of the original defect in each image. Red staining indicates the presence of glycosoaminoglycans (GAG), primarily hyaluronan, which is indicative of hyaline-like cartilage.
Figure 7:
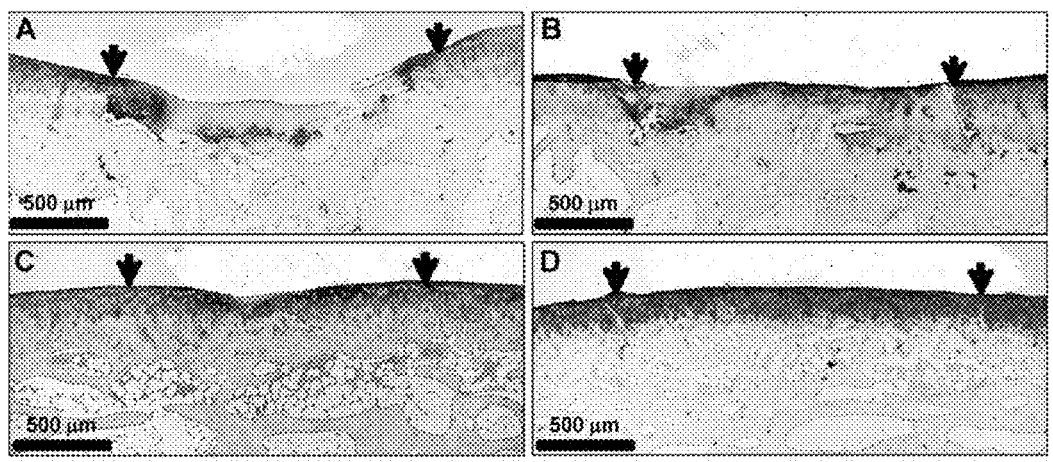
FIG. 7(a)-(d) are representative micrographs showing collagen type-II immunohistochemical staining of tissue sections from animals in treatment Group 1 (upper left), Group 2 (upper right), Group 3 (lower left) and Group 4 (lower right). Each section is through the center of one cartilage defect, harvested at 12 weeks. Small arrows indicate the approximate edges of the original defect in each image. Brown staining indicates the presence of type-II collagen, a marker for mature hyaline-like cartilage, as distinct from fibrocartilage, which expressed primarily type-I collagen.

Qualitative assessment of histological sections showed an obvious improvement in tissue morphology in animals treated with the TGF-binding PA (Group 3 and 4) compared to controls (Groups 1 and 2). There was greater tissue fill, Safranin-O staining and Type II collagen staining in the defects treated with a 9:1 mixture of the filler PA and TGF-binding PA, with or without the addition of exogenous growth factor (rhTGF-β1) (see FIGS. 6 and 7). A majority of the defects in Groups 3 and 4 had nearly complete filling of the defect area and contained tissue closely resembling that of hyaline-like cartilage. In some cases, the boundaries of the defect could not even be identified due to the close similarity in morphology to the surrounding cartilage. Although most of the defects in Group 1 and 2 did show evidence of tissue formation within the defects, few had complete filling of the defect area, and Safranin-O and collagen type II staining was typically not uniform or not present at all throughout the repair tissue.

A semi-quantitative histological assessment based on the well-established O'Driscoll scoring method[45] was performed by treatment-blinded observers. The results are summarized for each treatment group in Table 3. In this method, the tissue nature, structure, cellular density and adjacent tissue condition are evaluated and rated with defined criteria determining the assignment of each score. Scores in each category generally range from 0 (severely compromised tissue) to 3 (normal tissue), though some categories are scored 0-2 or 0-4 (see Table 3). The assessment revealed no significant difference between Group 1 and 2, with O'Driscoll scores of 15.5±4.7 and 15.1±3.7, respectively. These values are consistent with literature outcomes examining the microfracture treatment alone in the rabbit model.[47] From this data we conclude that 1 nanogram dose of rhTGF-β1 alone or in combination with the filler PA, does not appear to have a beneficial (or detrimental) effect on cartilage regeneration in this animal model.

Figure 8:
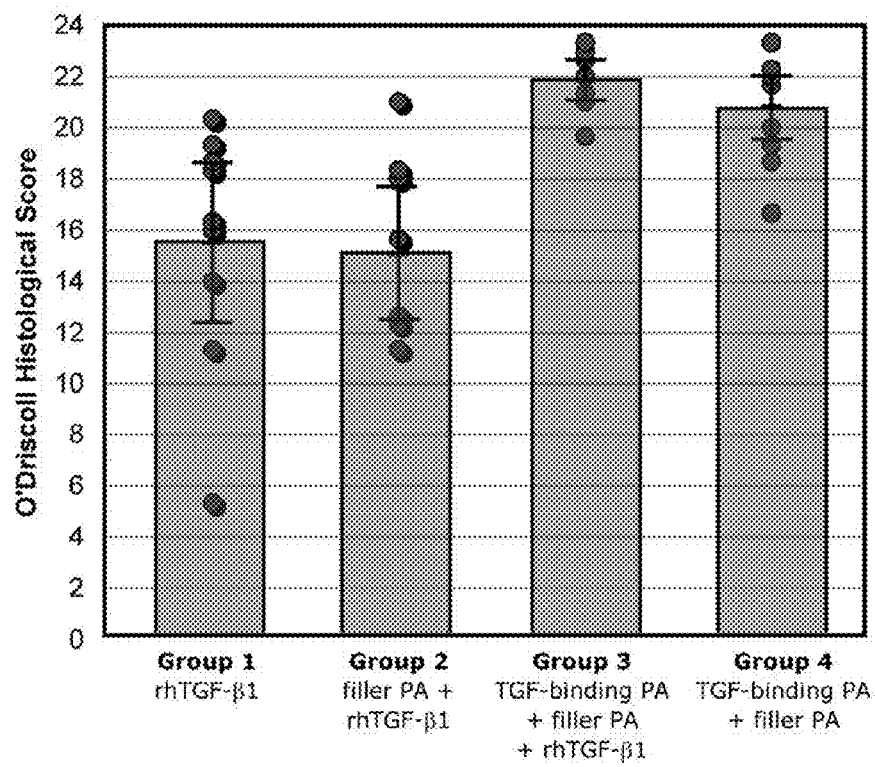
FIG. 8 shows a plot of O'Driscoll histological scores for the four treatment groups examined. Each data point (circles) represents the average score of three treatment-blind evaluators for a particular cartilage defect. Possible scores range from 0 (no hyaline-like repair tissue and extensive degeneration) to 24 (completely normal hyaline-like cartilage). Error bars represent 95% confidence intervals for the mean score in each group.

In contrast, both groups receiving the TGF-binding peptide amphiphile (PA) had a significantly higher O'Driscoll histological score than the group receiving the growth factor alone (Group 1) or the filler PA plus growth factor (Group 2). Group 4, which received the TGF-binding PA plus filler PA, had a histological score of 21.9±1.2, and Group 3, which received the same mix of PAs plus rhTGF-β1, had a histological score of 20.8±2.1, out of a maximum possible score of 24 (which represents normal, healthy and well-integrated hyaline-like cartilage). A univariant analysis of the data showed a significant effect of treatment ($p<0.0001$) on histological scoring. Post-hoc tests revealed significant differences between Group 1 compared to Group 3 ($p<0.0001$) or Group 4 ($p<0.001$), as well as between Group 2 compared to Group 3 ($p<0.0001$) or Group 4 ($p<0.0006$). There was no significant difference between Groups 3 and 4 (see FIG. 8).

TABLE 3

Histological Scores (O'Driscoll method) from Rabbit Full Thickness Articular Cartilage Defects at 12-weeks post-treatment.

| | Group 1 rhTGF-β1 | Group 2 filler PA + rhTGF-β1 | Group 3 filler PA + TGF-binding PA + rhTGF-β1 | Group 4 filler PA + TGF-binding PA |
|---|---|---|---|---|
| Evaluative Criteria (scoring as indicated) | Mean ± SD (n = 9) | Mean ± SD (n = 8) | Mean ± SD (n = 9) | Mean ± SD (n = 10) |
| Cellular morphology (score = 0, 2, or 4) | 2.56 ± 1.43 | 2.67 ± 1.38 | 3.93 ± 0.22 | 3.80 ± 0.45 |
| Safranin-O staining of matrix (score = 0, 1, 2 or 3) | 1.48 ± 0.60 | 1.21 ± 0.67 | 2.44 ± 0.24 | 2.30 ± 0.58 |
| Surface regularity (score = 0, 1, 2 or 3) | 2.00 ± 0.80 | 1.67 ± 0.69 | 2.41 ± 0.49 | 2.37 ± 0.51 |
| Structural integrity (score = 0, 1 or 2) | 1.07 ± 0.62 | 0.88 ± 0.40 | 1.70 ± 0.31 | 1.57 ± 0.32 |
| Thickness (score = 0, 1 or 2) | 1.15 ± 0.60 | 1.29 ± 0.55 | 1.85 ± 0.18 | 1.77 ± 0.32 |
| Bonding to adjacent cartilage (score = 0, 1 or 2) | 1.33 ± 0.53 | 1.13 ± 0.62 | 1.81 ± 0.18 | 1.80 ± 0.23 |
| Hypocellularity (score = 0, 1, 2 or 3) | 1.96 ± 0.72 | 2.08 ± 0.53 | 2.89 ± 0.17 | 2.63 ± 0.40 |
| Chondrocyte clustering (score = 0, 1 or 2) | 1.26 ± 0.40 | 1.46 ± 0.25 | 1.93 ± 0.15 | 1.73 ± 0.31 |
| Degenerative Changes (score = 0, 1, 2 or 3) | 2.70 ± 0.35 | 2.75 ± 0.24 | 2.89 ± 0.33 | 2.83 ± 0.24 |
| Total (max. score = 24) | 15.52 ± 4.74 | 15.13 ± 3.66 | 21.85 ± 1.19 | 20.80 ± 2.06 |

4.6.1 Thickness.

1 of 9 defects in Group 1 (rhTGF-β1) had <50% thickness compared to the surrounding cartilage. The remaining 8 defects had >50% but <100% fill compared to the surrounding normal cartilage. Similarly in Group 2 (filler PA+rhTGF-β1), 1 of 8 defects had <50% thickness and the remaining 7 defects had 50%-100% thickness compared to the surrounding cartilage. In contrast, all of the defects in the Group 3 (TGF-binding PA+filler PA+rhTGF-β1) contained tissue that filled 100% of the thickness relative to the normal adjacent cartilage, and 7 of 10 defects in Group 4 (TGF-binding PA+filler PA) were similarly completely filled.

4.6.2 Bonding to the Adjacent Cartilage.

In Group 1, only 3 of 9 defects showed regenerated tissue that completely bonded to the adjacent cartilage, and similarly in Group 2 only 2 of 8 were completely bonded, with the remaining defects being partially bonded or completely unbonded. In contrast, all of the defects in the Group 3, and 9 of 10 defects in Group 4 were completely were bonded completely to the adjacent cartilage.

4.6.3 Hypocellularity.

Only 2 of 9 defects in Group 1 (and 2 of 8 in Group 2) had normal cellularity in the regenerated tissue, with the remaining exhibiting slight to severe hypocellularity. In contrast, all of the defects in Group 3 (and 8 of 10 in Group 4) exhibited normal cellularity.

4.6.4 Chondrocyte Clustering.

In Group 1, 7 of 9 defects had mild chondrocyte clustering. In Group 2, 1 of 8 defects had moderate clustering, while the majority had minimal to no chondrocyte clustering. No chondrocyte clustering was observed in Group 3, and only 3 of 10 defects had minimal clustering in Group 4.

4.6.5 Freedom from Degenerative Changes in Adjacent Cartilage.

Little to no degenerative changes in adjacent cartilage were observed across all treatment groups, with mild changes observed in only 1 or 2 defects per group.

INDUSTRIAL APPLICABILITY

Full thickness chondral lesions on articular joint surfaces (including the knee, hip, shoulder, elbow, and ankle) lead to pain, dysfunction, mechanical symptoms, swelling, adjacent cartilage degeneration, and osteoarthritis in human patients. Chondral injuries affect ability to return to work, athletic activity as well as activities of daily living. Current treatment options include arthroscopic microfracture, open osteochondral allograft transplantation (OATS), and open two-stage autologous chondrocyte implantation (ACI). A recent meta-analysis has shown that no treatment alternative had consistently superior results in terms of a return to prior function and activity.[38] Additionally, histological analysis has shown no significant long term ability of these treatment options to retain significant chondrocyte viability or type II collagen production, processes that are critical to the promotion of self-healing, the maintenance of joint elasticity and the collective retention of cartilage in situ.[37]

The novel compositions described here can be used in multiple clinical situations. Chondral injuries, although most frequently diagnosed in the knee, are seen in almost every joint in the human body due to traumatic injuries, including but not limited to: dislocations, direct impact, ligamentous instability, sheer stress, athletic injuries, and work-related mechanisms. Microfracture has been shown to work well in the short-term in small (<4 mm) lesions based on clinical outcome scores; but generally fibrocartilage is formed and not articular cartilage.[48] Larger lesions typically perform poorly after microfracture.[38]

In light of the forgoing limitations of current treatments for cartilage lesions, a TGF-binding gel scaffold has been developed that can be used as an adjunct to microfracture. This scaffold may improve the outcomes of smaller chondral lesions by way of promoting differentiation of mesenchymal stem cells into viable chondrocytes that produce and maintain articular cartilage (including predominantly type II collagen expression). Additionally, larger lesions may perform better when a gel scaffold is used as an adjunct to microfracture in any joint.

This novel therapy may be used as a first-line procedure for cartilage restoration/regeneration with microfracture, in either the acute or chronic setting of chondral defects. Additionally, it may be used as a revision procedure in the setting of failed abrasion arthroplasty, microfracture, autologous chondrocyte implantation, or OATS if these methods have failed to show clinical, arthroscopic, or histological improvement.

REFERENCES

1. Avrahami, D.; Y. Shai "Conjugation of a magainin analogue with lipophilic acids controls hydrophobicity, solution assembly, and cell selectivity" *Biochemistry* 2002, 41 (7), 2254-63.
2. de Loos, M.; B. L. Feringa; J. H. van Esch "Design and application of self-assembled low molecular weight hydrogels" *Eur. J. Org. Chem.* 2005, (17), 3615-31.
3. Fields, G. B. "Induction of protein-like molecular architecture by self-assembly processes" *Bioorg. Med. Chem.* 1999, 7 (1), 75-81.
4. Fields, G. B.; J. L. Lauer; Y. Dori; P. Forns; Y. C. Yu; M. Tirrell "Proteinlike molecular architecture: Biomaterial applications for inducing cellular receptor binding and signal transduction" *Biopolymers* 1998, 47 (2), 143-51.
5. Forns, P.; J. L. Lauer-Fields; S. Gao; G. B. Fields "Induction of protein-like molecular architecture by monoalkyl hydrocarbon chains" *Biopolymers* 2000, 54 (7), 531-46.
6. Mardilovich, A.; J. A. Craig; M. Q. McCammon; A. Garg; E. Kokkoli "Design of a novel fibronectin-mimetic peptide-amphiphile for functionalized biomaterials" *Langmuir* 2006, 22 (7), 3259-64.
7. McGregor, C. L.; L. Chen; N. C. Pomroy; P. Hwang; S. Go; A. Chakrabartty; G. G. Prive "Lipopeptide detergents designed for the structural study of membrane proteins" *Nat. Biotechnol.* 2003, 21 (2), 171-76.
8. Paramonov, S. E.; H. W. Jun; J. D. Hartgerink "Self-assembly of peptide-amphiphile nanofibers: The roles of hydrogen bonding and amphiphilic packing" *Journal of the American Chemical Society* 2006, 128 (22), 7291-98.
9. Stendahl, J. C.; M. S. Rao; M. O. Guler; S. I. Stupp "Intermolecular forces in the self-assembly of peptide amphiphile nanofibers" *Adv. Func. Mater.* 2006, 16, 499-508.
10. Tovar, J. D.; R. C. Claussen; S. I. Stupp "Probing the interior of peptide amphiphile supramolecular aggregates" *Journal of the American Chemical Society* 2005, 127 (20), 7337-45.
11. Yu, Y. C.; P. Berndt; M. Tirrell; G. B. Fields "Self-assembling amphiphiles for construction of protein molecular architecture" *Journal of the American Chemical Society* 1996, 118 (50), 12515-20.
12. Yu, Y. C.; M. Tirrell; G. B. Fields "Minimal lipidation stabilizes protein-like molecular architecture" *Journal of the American Chemical Society* 1998, 120 (39), 9979-87.
13. Beniash, E.; J. D. Hartgerink; H. Storrie; S. I. Stupp "Self-assembling peptide amphiphile nanofiber matrices for cell entrapment" *Acta Biomaterialia* 2005, 1 (4), 387-97.
14. Bitton, R.; J. Schmidt; M. Biesalski; R. Tu; M. Tirrell; H. Bianco-Peled "Self-assembly of model DNA-binding peptide amphiphiles" *Langmuir* 2005, 21 (25), 11888-95.

15. Brunsveld, L.; J. Kuhlmann; H. Waldmann "Synthesis of palmitoylated Ras-peptides and -proteins" *Methods* 2006, 40 (2), 151-65.
16. Bull, S. R.; M. O. Guler; R. E. Bras; T. J. Meade; S. I. Stupp "Self-assembled peptide amphiphile nanofibers conjugated to MRI contrast agents" *Nano Lett.* 2005, 5 (1), 1-4.
17. Bull, S. R.; M. O. Guler; R. E. Bras; P. N. Venkatasubramanian; S. I. Stupp; T. J. Meade "Magnetic resonance imaging of self-assembled biomaterial scaffolds" *Bioconjugate Chem.* 2005, 16 (6), 1343-48.
18. Guler, M. O.; R. C. Claussen; S. I. Stupp "Encapsulation of pyrene within self-assembled peptide amphiphile nanofibers" *J. Mater. Chem.* 2005, 15 (42), 4507-12.
19. Guler, M. O.; L. Hsu; S. Soukasene; D. A. Harrington; J. F. Hulvat; S. I. Stupp "Presentation of RGDS epitopes on self-assembled nanofibers of branched peptide amphiphiles" *Biomacromolecules* 2006, 7 (6), 1855-63.
20. Guler, M. O.; J. K. Pokorski; D. H. Appella; S. I. Stupp "Enhanced oligonucleotide binding to self-assembled nanofibers" *Bioconjugate Chem.* 2005, 16 (3), 501-03.
21. Guler, M. O.; S. Soukasene; J. F. Hulvat; S. I. Stupp "Presentation and recognition of biotin on nanofibers formed by branched peptide amphiphiles" *Nano Lett.* 2005, 5 (2), 249-52.
22. Harrington, D. A.; E. Y. Cheng; M. O. Guler; L. K. Lee; J. L. Donovan; R. C. Claussen; S. I. Stupp "Branched peptide-amphiphiles as self-assembling coatings for tissue engineering scaffolds" *J. Biomed. Mater. Res. Part A* 2006, 78A (1), 157-67.
23. Hosseinkhani, H.; M. Hosseinkhani; A. Khademhosseini; H. Kobayashi; Y. Tabata "Enhanced angiogenesis through controlled release of basic fibroblast growth factor from peptide amphiphile for tissue regeneration" *Biomaterials* 2006, 27 (34), 5836-44.
24. Hosseinkhani, H.; M. Hosseinkhani; H. Kobayashi "Design of tissue-engineered nanoscaffold through self-assembly of peptide amphiphile" *J. Bioact. Compat. Polym.* 2006, 21 (4), 277-96.
25. Rajangam, K.; H. A. Behanna; M. J. Hui; X. Q. Han; J. F. Hulvat; J. W. Lomasney; S. I. Stupp "Heparin binding nanostructures to promote growth of blood vessels" *Nano Lett.* 2006, 6 (9), 2086-90.
26. Smith, L. A.; P. X. Ma "Nano-fibrous scaffolds for tissue engineering" *Colloid Surf. B-Biointerfaces* 2004, 39 (3), 125-31.
27. Behanna, H. A.; J. J. J. M. Donners; A. C. Gordon; S. I. Stupp "Coassembly of amphiphiles with opposite peptide polarities into nanofibers" *Journal of the American Chemical Society* 2005, 127 (4), 1193-200.
28. Jackson, D. W.; T. M. Simon; H. M. Aberman "Symptomatic articular cartilage degeneration: The impact in the new millennium" *Clin Orthop Relat Res* 2001, (391 Suppl), S14-25.
29. Curl, W. W.; J. Krome; E. S. Gordon; J. Rushing; B. P. Smith; G. G. Poehling "Cartilage injuries: A review of 31,516 knee arthroscopies" *Arthroscopy* 1997, 13 (4), 456-60.
30. Aroen, A.; S. Loken; S. Heir; E. Alvik; A. Ekeland; O. G. Granlund; L. Engebretsen "Articular cartilage lesions in 993 consecutive knee arthroscopies" *Am Sports Med* 2004, 32 (1), 211-5.
31. Gunes, T.; C. Sen; M. Erdem; R. D. Koseoglu; N, O. Filiz "Combination of microfracture and periosteal transplantation techniques for the treatment of full-thickness cartilage defects" *Acta Orthop Traumatol Turc* 2006, 40 (4), 315-23.
32. Kreuz, P. C.; M. R. Steinwachs; C. Erggelet; S. J. Krause; G. Konrad; M. Uhl; N. Sudkamp "Results after microfracture of full-thickness chondral defects in different compartments in the knee" *Osteoarthritis and Cartilage* 2006, 14 (11), 1119-25.
33. Horas, U.; D. Pelinkovic; G. Herr; T. Aigner; R. Schnettler "Autologous chondrocyte implantation and osteochondral cylinder transplantation in cartilage repair of the knee joint. A prospective, comparative trial" *Bone Joint Surg Am* 2003, 85-A (2), 185-92.
34. Gross, A. E. "Repair of cartilage defects in the knee" *Knee Surg* 2002, 15 (3), 167-9.
35. Huntley, J. S.; P. G. Bush; J. M. McBirnie; A. H. Simpson; A. C. Hall "Chondrocyte death associated with human femoral osteochondral harvest as performed for mosaicplasty" *J Bone Joint Surg Am* 2005, 87 (2), 351-60.
36. Sgaglione, N. A.; A. Miniaci; S. D. Gillogly; T. R. Carter "Update on advanced surgical techniques in the treatment of traumatic focal articular cartilage lesions in the knee" *Arthroscopy* 2002, 18 (2 Suppl 1), 9-32.
37. Knutsen, G.; J. O. Drogset; L. Engebretsen; T. Grontvedt; V. Isaksen; T. C. Ludvigsen; S. Roberts; E. Solheim; T. Strand; 0. Johansen "A randomized trial comparing autologous chondrocyte implantation with microfracture. Findings at five years" *Bone Joint Surg Am* 2007, 89 (10), 2105-12.
38. Magnussen, R. A.; W. R. Dunn; J. L. Carey; K. P. Spindler "Treatment of focal articular cartilage defects in the knee: A systematic review" *Clin Orthop Relat Res* 2008, 466 (4), 952-62.
39. Smith, G. P. "Phage display" *Chem. Rev.* 1997, 97, 391.
40. Hoess, R. H. "Protein design and phage display" *Chem. Rev.* 2001, 101, 3205.
41. Dounchis, J. S.; R. S. Goomer; F. L. Harwood; M. Khatod; R. D. Coutts; D. Amiel "Chondrogenic phenotype of perichondrium-derived chondroprogenitor cells is influenced by transforming growth factor-beta 1" *Orthop Res* 1997, 15 (6), 803-7.
42. Johnstone, B.; T. M. Hering; A. I. Caplan; V. M. Goldberg; J. U. Yoo "In vitro chondrogenesis of bone marrow-derived mesenchymal progenitor cells" *Experimental cell research* 1998, 238 (1), 265-72.
43. O'Connor, W. J.; T. Botti; S, N. Khan; J. M. Lane "The use of growth factors in cartilage repair" *The Orthopedic clinics of North America* 2000, 31 (3), 399-410.
44. Chang, H.; C. W. Brown; M. M. Matzuk "Genetic analysis of the mammalian transforming growth factor-beta superfamily" *Endocr. Rev.* 2002, 23 (6), 787-823.
45. O'Driscoll, S. W.; R. G. Marx; D. E. Beaton; Y. Miura; S. H. Gallay; J. S. Fitzsimmons "Validation of a simple histological-histochemical cartilage scoring system" *Tissue Eng* 2001, 7 (3), 313-20.
46. Nehrer, S.; H. A. Breinan; A. Ramappa; S. Shortkroff; G. Young; T. Minas; C. B. Sledge; I. V. Yannas; M. Spector "Canine chondrocytes seeded in type I and type II collagen implants investigated in vitro" *Biomed Mater Res* 1997, 38 (2), 95-104.
47. Hoemann, C. D.; J. Sun; M. D. McKee; A. Chevrier; E. Rossomacha; G.-E. Rivard; M. Hurtig; M. D. Buschmann "Chitosan-glycerol phosphate/blood implants elicit hyaline cartilage repair integrated with porous subchondral bone in microdrilled rabbit defects" *Osteoarthritis and Cartilage* 2007, 15, 78-89.
48. Mithoefer, K.; R. J. Williams, III; R. F. Warren; H. G. Potter; C. R. Spock; E. C. Jones; T. L. Wickiewicz; R. G. Marx "The microfracture technique for the treatment of articular cartilage lesions in the knee. A prospective cohort study" *Bone Joint Surg Am* 2005, 87 (9), 1911-20.
49. Shah, R. N.; N. A. Shah; M. M. Del Rosario Lim; C. Hsieh; G. Nuber; S. I. Stupp "Supramolecular design of self-assembling nanofibers for cartilage regeneration" *Proc Nat Acad Sci USA,* 2010, 107(8) 3293-8.

All patents and publications mentioned herein are incorporated by reference in their entirety. Nothing herein is to be construed as an admission that the invention is not entitled to antedate such disclosure by virtue of prior invention.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. For instance, various peptide amphiphiles have been described in conjunction with specific amino acid residues; however, other residues can be used herewith to promote a particular tissue growth and regeneration on the nanostructures prepared therefrom. Likewise, while the present invention has been described as applicable to biomedical or tissue engineering use, other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

What is claimed:

1. A synthetic peptide comprising the sequence HSNGLPLGGGSEEEAAAVVVK (SEQ ID NO:3).

2. A peptide amphiphile consisting of the following segments: (1) a growth-factor-binding peptide segment selected from among SEQ ID NOs:21-40; (2) a spacer segment comprising GGGSEEE (SEQ ID NO:5); (3) a beta-sheet forming, structural peptide segment, and (4) a non-peptide lipophilic segment.

3. The peptide amphiphile of claim 2 wherein the structural peptide segment is AAAVVVK (SEQ ID NO:10).

4. The peptide amphiphile of claim 2 wherein the lipophilic segment is comprised of a single, saturated, linear alkyl chain of the formula: CnH2n-1O-, where n 6-22, and wherein the lipophilic segment is covalently linked to the epsilon amine of a C-terminal lysine residue.

5. A peptide amphiphile consisting of the following structure (SEQ ID NO:4).

6. A composition comprising one or more peptide amphiphiles selected from the compounds of claim 2, mixed with one or more filler peptide amphiphiles and dispersed in an aqueous medium, wherein said filler peptide amphiphile comprises the sequence VVVAAAEEE (SEQ ID NO:7).

7. The composition of claim 6 wherein said peptide amphiphile composition further comprises one or more recombinant human proteins of the transforming growth factor (TGF) superfamily.

8. The composition of claim 7 wherein said recombinant human protein is rhTGF-β1.

9. A method of treating an articular cartilage defect or lesion in a patient in need thereof said method comprising debridement of a cartilage defect or lesion on articular surface of a joint in a patient in need thereof, and contacting the debrided surface of the joint with the composition claim 6 to said patient.

10. The method of claim 9 wherein said composition is administered as an adjuvant to an orthopedic surgical procedure intended to repair, restore or regenerate damaged or missing cartilage.

11. The method of claim 9 wherein said surgical procedure is microfracture, and said composition forms a gel-clot with autologous blood and cells released from the osteochondral bone or marrow during the microfracture procedure.

12. The method of claim 9 wherein the surgical procedure is an open two-stage autologous chondrocyte implantation (ACI), wherein said composition is combined with the autologous chondrocytes and forms a gel scaffold containing the cells in the lesion site.

13. The method of claim 9 wherein the surgical procedure is an open osteochondral allograft transplantation (OATS), wherein said composition forms a gel in the lesion site.

14. The method of claim 9 wherein said composition is administered arthroscopically.

15. The method of claim 9, wherein the patient is human.

16. The method of claim 9, wherein the patient is an animal.

17. The method of claim 9, wherein the patient is a horse, dog, sheep, goat, or cow.

18. A method of treating an articular cartilage defect or lesion in a patient in need thereof, comprising debridement of a cartilage defect or lesion on the articular surface of a joint in a patient in need thereof, and contacting the debrided surface of the joint with the composition of claim 1.

19. The method of claim 18, wherein the composition is administered as an adjuvant to an orthopedic surgical procedure intended to repair, restore or regenerate damaged or missing cartilage and wherein said orthopedic surgical procedure is an open two-state autologous chondrocyte implantation (ACI), wherein said composition is combined with the autologous chondrocytes and forms a gel scaffold containing the cells in lesion site.

20. The method of claim 18, wherein the composition is administered as an adjuvant to an orthopedic surgical procedure intended to repair, restore or regenerate damaged or missing cartilage and wherein said orthopedic surgical procedure is an open osteochondral allograft transplantation (OATS), wherein said composition forms a gel in the lesion site.

21. A substrate coated with self-assembled micelles formed by the peptide amphiphile composition of claim 2.

22. A kit for the in vitro formation of self-assembled micelles for administration into a patient comprising a peptide amphiphile of claim 1 and one or more aqueous components, wherein said one or more aqueous components are used to dissolve said peptide amphiphiles sufficient to induce self-assembly or gel formation, said self-assembly resulting from changes in the pH of the solution or the presence of multivalent ions, charged polymers or other charged macromolecules in said components.

23. The kit of claim 22, optionally comprising components suitable to remove cells in the patient for incorporation into the formulation for administration to the patient.

24. A kit for making an injectable formulation for the in vivo formation of cylindrical micelles in a patient in need thereof comprising a peptide amphiphile composition of claim 2.

25. The kit of claim 24, optionally comprising components suitable to remove cells in the patient for incorporation into the formulation for administration to the patient.

26. A method of concentrating and protecting endogenous TGF-β1 released by cells in an area of articular cartilage deficiency comprising the step of administering to a patient in need thereof a composition of claim 6, wherein the administration step is performed during a microfracture procedure.

27. A method of concentrating and protecting endogenous TGF-β1 released by cells in an area of articular cartilage deficiency comprising the step of administering to a patient in need thereof a composition of claim 6, wherein the administration step is performed during an ACI procedure.

* * * * *

```
                        SEQUENCE LISTING

<160> NUMBER OF SEQ ID NOS: 43

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

His Ser Asn Gly Leu Pro Leu
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Gly Ser
1

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Ser Asn Gly Leu Pro Leu Gly Gly Gly Ser Glu Glu Glu Ala Ala
1               5                   10                  15

Ala Val Val Val Lys
            20

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 4

His Ser Asn Gly Leu Pro Leu Gly Gly Gly Ser Glu Glu Glu Ala Ala
1               5                   10                  15

Ala Val Val Val Lys
            20

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Ser Glu Glu Glu
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ala Ala Val Val Val Lys
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Val Val Ala Ala Ala Glu Glu Glu
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Val Val Ala Ala Ala Glu Glu Glu
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Val Val Ala Ala Ala
1               5

```
<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Ala Ala Val Val Val
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Leu Leu Ala Ala Ala
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Val Val Val Val Val
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Val Val Leu Leu Leu
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Leu Leu Val Val Val
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15
```

```
Ala Ala Ala Ala Ala Ala
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Ala Ala Ala Gly Gly Gly
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Leu Leu Leu Leu Leu
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ala Ala Gly Gly Gly
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Leu Leu Gly Gly Gly
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ala Ala Leu Leu Leu
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 21

His Ser Asn Gly Leu Pro Leu
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser His Ser Tyr Asn Arg Leu
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Pro Leu His Arg Tyr Val
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Asp Trp Thr Ser Val Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

His Ile Trp Arg Pro Ala Pro
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Thr Pro Ser Thr Thr Arg
1               5

<210> SEQ ID NO 27
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Thr Pro Pro Tyr Lys Gly
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Thr Val Ser Lys Trp Ala
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Gln Ile Pro Ser Pro Leu
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Pro Leu Gly Asn Ser His
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Arg Asn Tyr Ser His Ser
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Tyr Arg His Leu Pro Thr
1               5
```

```
<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Val Ser Thr Trp Asp Thr
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Pro Ala Pro Arg Trp Ile His
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Thr Thr Ser Pro Thr Ala
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Lys Tyr Pro Pro Thr Ser
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Trp Lys Ser Val Thr Ala
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 38

Leu Pro Ser Pro Ile Gln Lys
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

His Ser Asp Gly Leu Pro Leu
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Isoaspartic acid

<400> SEQUENCE: 40

His Ser Asp Gly Leu Pro Leu
1               5

<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

His Ser Asp Gly Leu Pro Leu Gly Gly Gly Ser Glu Glu Glu Ala Ala
1               5                   10                  15

Ala Val Val Val Lys
            20

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: This region may encompass 0-5 residues
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(11)
<223> OTHER INFORMATION: Any amino acid with an acidic side chain
<220> FEATURE:
<221> NAME/KEY: misc_feature
<222> LOCATION: (7)..(11)
<223> OTHER INFORMATION: This region may encompass 0-5 residues
<220> FEATURE:
<223> OTHER INFORMATION: See specification as filed for detailed
```

```
                            -continued
     description of substitutions and preferred embodiments

<400> SEQUENCE: 42

Gly Gly Gly Gly Gly Xaa Xaa Xaa Xaa Xaa Xaa
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: This region may encompass 0-6 residues
<220> FEATURE:
<221> NAME/KEY: misc_feature
<222> LOCATION: (7)..(12)
<223> OTHER INFORMATION: This region may encompass 0-6 residues
<220> FEATURE:
<223> OTHER INFORMATION: See specification as filed for detailed
      description of substitutions and preferred embodiments

<400> SEQUENCE: 43

Ala Ala Ala Ala Ala Ala Val Val Val Val Val Val
1               5                   10
```